US007645572B2

United States Patent
(12)

Yamada et al.

(10) Patent No.: US 7,645,572 B2

(45) Date of Patent: Jan. 12, 2010

(54) METHOD OF DIAGNOSING RISK OF RESTENOSIS AFTER CORONARY ANGIOPLASTY

(75) Inventors: Yoshiji Yamada, Nagoya (JP); Mitsuhiro Yokota, Nagoya (JP)

(73) Assignee: Nagoya Industrial Science Research Institute, Nagoya-shi (JP)

( * ) Notice: Subject to any disclaimer, the term of this patent is extended or adjusted under 35 U.S.C. 154(b) by 208 days.

(21) Appl. No.: 10/524,021

(22) PCT Filed: Mar. 20, 2003

(86) PCT No.: PCT/JP03/03478

§ 371 (c)(1), (2), (4) Date: Feb. 9, 2005

(87) PCT Pub. No.: WO2004/015104

PCT Pub. Date: Feb. 19, 2004

(65) Prior Publication Data

US 2006/0099590 A1 May 11, 2006

(30) Foreign Application Priority Data

Aug. 9, 2002 (JP) ............................ 2002-233041

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.1

(58) Field of Classification Search ....................... None
See application file for complete search history.

(56) References Cited

U.S. PATENT DOCUMENTS 5,474,796 A * 12/1995 Brennan .................... 427/2.13

OTHER PUBLICATIONS

TNF gene information. Mouse Genome Informatics[online]. URL:http://www.informatics.jax.org/searches/snp_report.cgi?_Marker_key=25061.*

Hirschhorn et al. Genetics in Medicine. vol. 4, No. 2, pp. 45-61, Mar. 2002.*

Ioannidis. Nature Genetics, vol. 29, pp. 306-309, Nov. 2001.*

Lucentini (The Scientist, 2004, 18(24):20.*

Watanabe, et al. Thromb Haemost. Dec. 2001;86(6):1594-5.*

Samani N.J. et al 'Apolipoprotein E polymorphism does not predict risk of restenosis after coronary angioplasty' Atherosclerosis (1996) vol. 125 p. 209-216.* von Beckerath N. et al 'G Protein B3 subunit polymorphism and risk of thrombosis and restenosis following coronary stent placement' Atherosclerosis (2000) vol. 149 p. 151-155.*

Koch W. et al 'Tumor necrosis factor-a, lymphotoxin-a, and interleukin-10 gene polymorphisms and restenosis after coronary artery stenting' Cytokine (2003) vol. 24 p. 161-171.*

Nassar Bassam A et al: "Relation of genetic polymorphism of apolipoprotein E, angiotensin converging enzyme, apolipoprotein B-100, and glycoprotein IIIa and early-onset coronary heart disease", Clinical Biochemistry, vol. 32, No. 4, Jun. 1999, pp. 275-282.

Brscic Elvis et al: "Acute myocardial infarction in young adults: Prognostic role of angiotensin-converting enzyme, angiotensin II type I receptor, apolipoprotein E, endothelial constitutive nitric oxide synthase, and glycoprotein IIIa genetic polymorphism at medium-term follow-up", American Heart Journal, vol. 139, No. 6., Jun. 2000, pp. 979-984.

Reiner A P et al: "Platelet glycoprotein gene polymorphism and risk of thrombosis: facts and fancies.", Reviews in Clinical and Experimental Hematology, Sep. 2001, vol. 5, No. 3, pp. 262-287.

Daley G Q et al: "The heart SNPs a beat: polymorphism in candidate genes for cardiovascular disease.", Trends in Cardiovascular Medicine, Feb. 2001, vol. 11, No. 2, pp. 60-66.

Yamada Yoshiji et al: "Prediction of the risk of myocardial infarction from polymorphism in candidate genes.", New England Journal of Medicine, Dec. 2002, vol. 347, No. 24, pp. 1916-1923.

Izawa Hideo et al: "Prediction of genetic risk for hypertension", Hypertension (Baltimore), May 2003, vol. 41, No. 5, pp. 1035-1040.

McBride, W., et al. "Restenosis After Successful Coronary Angioplasty;" *The New England Journal of Medicine*, vol. 318, No. 26, pp. 1734-1737 (Jun. 1988).

Hirshfeld, J. W., Jr., et al. "Restenosis After Coronary Angioplasty: A Multivariate Statistical Model to Relate Lesion and Procedure Variables to Restenosis;" *JACC*, vol. 18, No. 3, pp. 647-656 (Sep. 1991).

Weintraub, W. S., et al. "Can Restenosis After Coronary Angioplasty Be Predicted From Clinical Variables?;" *JACC*, vol. 21, No. 1, pp. 6-14 (Jan. 1993).

van Bockxmeer, F. M., et al. "Apolipoprotein ∈4 homozygosity—a determinant of restenosis after coronary angioplasty;" *Atherosclerosis* 110, pp. 195-202 (1994).

Yamada, Y., et al. "Prediction of the Risk of Myocardial Infarction From Polymorphisms in Candidate Genes;" *The New England Journal of Medicine*, vol. 347, No. 24, pp. 1916-1923 (Dec. 2002) and Supplementary Appendix 1.

Ortlepp, J. R., et al. "The 4G/5G Promotor Polymorphism of the Plasminogen Activator Inhibitor-1 Gene and Late Lumen Loss after Coronary Stent Placement in Smoking and Nonsmoking Patients;" *Clin. Cardiol*. vol. 24, pp. 585-591 ( Sep. 2001).

Clausell, N., et al. "Expression of tumour necrosis factor $\alpha$ and accumulation of fibronectin in coronary artery restenotic lesions retrieved by atherectomy;" *Br Heart*, 73, pp. 534-539 (1995).

(Continued)

*Primary Examiner*—Stephen Kapushoc

(74) *Attorney, Agent, or Firm*—Edwards Angell Palmer & Dodge LLP

(57) ABSTRACT

It is intended to provide a means of diagnosing genetic risk of restenosis after coronary angioplasty which shows a high accuracy and a high estimation ratio. The risk of restenosis after coronary angioplasty is diagnosed by a method comprising the following steps: (i) the step of analyzing 2 or more polymorphisms among 6 gene polymorphisms proved as relating to restenosis after balloon expansion or 5 gene polymorphisms proved as relating to restenosis after stent insertion; (ii) the step of determining the genotype of a nucleic acid sample based on the polymorphism data obtained in the above step; and (iii) the step of determining the genetic risk of restenosis after coronary angioplasty form the genotype thus determined.

1 Claim, 16 Drawing Sheets

OTHER PUBLICATIONS

Gawaz, M., et al. "Changes in membrane glycoproteins of circulating platelets after coronary stent implantation;" *Heart*, 76, pp. 166-172 (1996).

C. Amant, et al.; "D Allele of the Angiotensin I-Converting Enzyme Is a Major Risk Factor for Restenosis After Coronary Stenting;" *Circulation*; vol. 96; No. 1; Jul. 1, 1997; pp. 56-60. (11 Sheets).

F. Ribichini, et al; "Plasma Activity and Insertion/Deletion Polymorphism of Angiotensin I-Converting Enzyme;" *Circulation*; vol. 97; 1998; pp. 147-154.

H. Völzke, et al.; "The angiotensinogen gene 235T variant is associated with an increased risk of restenosis after percutaneous transluminal coronary angioplasty;" *Clinical Science*; vol. 99; 2000; pp. 19-25.

D. H. Walter, et al; "Platelet Glycoprotein IIIA Polymorphisms and Risk of Coronary Stent Thrombosis;" *Lancet*; vol. 350; 1997; pp. 1217-1219. (7 Sheets).

S. Humphries, et al.; "The 5A6A polymorphism in the promoter of the stromelysin-1 (MMP3) gene as a risk factor for restenosis;" *European Heart Journal*; vol. 23; 2002; pp. 721-725.

M. Rauchhaus, et al.; "The E-selectin SER128ARG gene polymorphism and restenosis after successful coronary angioplasty;" *International Journal of Cardiology*; vol. 83; 2002; pp. 249-257.

N. von Beckerath, et al.; "Glycoprotein Ia C807T polymorphism and risk of restenosis following coronary stenting;" *Atherosclerosis*; vol. 156; 2001; pp. 463-468.

N. von Beckerath; "G Protein β3 subunit polymorphism and risk of thrombosis and restenosis following coronary stent placement;" *Atherosclerosis*; vol. 149; 2000; pp. 151-155.

H. Matsuno, et al; "Inhibition of von Willebrand Factor Binding to Platelet GP Ib by a Fractionated Aurintricarboxylic Acid Prevents Restenosis After Vascular Injury in Hamster Carotid Artery;" *Circulation*; vol. 96; No. 4; Aug. 19, 1997; pp. 1299-1304. (15 Sheets).

G. Iaccarino, et al; "Targeting $G_{\beta\gamma}$ signaling in arterial vascular smooth muscle proliferation: A novel strategy to limit restenosis;" *Proc. Natl. Acad. Sci. USA*; vol. 96; Mar. 1999; pp. 3945-3950.

N. Clausell, et al.; "Expression of tumour necrosis factor alpha and accumulation of fibronectin in coronary artery restenotic lesions retrieved by atherectomy;" *British Heart Journal*; vol. 76; No. 6; Jun. 1995; pp. 534-539 (1 Sheet-Abstract only).

M. Gawaz, et al.; "Changes in membrane glycoproteins of circulating platelets after coronary stent implantation;" *Heart*; vol. 76; 1996; pp. 166-172 (1 Sheet-Abstract only).

Ryl Zee, et al.; "Multi-locus interactions predict risk for post-PTCA restenosis: an approach to the genetic analysis of common complex disease;" *The Pharmacogenomics Journal*; vol. 2; 2002; pp. 197-201./Cited in the International Search Report.

N. von Beckerath, et al.; "Glycoprotein Ia gene C807T polymorphism and risk for major adverse cardiac events within the first 30 days after coronary artery stenting;" *Blood*; vol. 96, No. 11; Jun. 2000; pp. 3297-3301./Cited in the International Search Report.

I. Taniguchi, et al.; "The DD genotype of angiotensin converting enzyme polymorphism is a risk factor for coronary artery disease and coronary stent restenosis in Japanese patients;" *Jpn. Circ. J.*; vol. 65; No. 10; Oct. 2001; pp. 897-900./Cited in the International Search Report.

M. Hamon, et al.; "Dual determination of angotensin-converting enzyme and angiotensin-II type 1 receptor genotypes as predictors of restenosis after coronary angioplasty;" *Am. J. Cardiol*; vol. 81; No. 1; Jan. 1998; pp. 79-81./Cited in the International Search Report.

P.W. Serruys, et al; "A Comparison of Balloon-Expandable-Stent Implantation with Balloon Angioplasty in Patients with Coronary Artery Disease;" *Benestent Study Group. New England Journal of Medicine*; vol. 331; Aug. 25, 1994; pp. 489-495. (18 Sheets).

B. Stein, et al; "Coronary Heart Disease/Myocardial Infarction: Influence of Diabetes Mellitus on Early and Late Outcome After Percutaneous Transluminal Coronary Angioplasty;" *Circulation*; vol. 91; No. 4; Feb. 15, 1995; pp. 979-989. (22 Sheets).

A.G. Violaris; "Interventional Cardiology: Long-Term Luminal Renarrowing After Successful Elective Coronary Angioplasty of Total Occlusions: A Quantitative Angiographic Analysis;" *Circulation*; vol. 91; No. 8; Apr. 15, 1995; pp. 2140-2150. (24 Sheets).

G.S. Mintz, et al.; "Arterial Remodeling After Coronary Angioplasty: A Serial Intravascular Ultrasound Study;" *Circulation*; vol. 94; No. 1; Jul. 1, 1996; pp. 35-43. (20 Sheets).

R. Hoffman, et al.; "Coronary Heart Disease/Myocardial Infarction/ Bypass Grafts/Endothelial Function: Patterns and Mechanisms of In-Stent Restenosis: A Serial Intravascular Ultrasound Study;" *Circulation*; vol. 94; No. 6; Sep. 15, 1996; pp. 1247-1254. (18 Sheets).

Hartmut Kroll et al., "The Impact of the Glycoprotein la Collagen Receptor Subunit $A_{1648}G$ Gene Polymorphism on Coronary Artery Disease and Acute Myocardial Infarction," Thrombosis and Haemostasis, vol. 83, 2000, pp. 392-396 and a cover page.

Molecular Medicine, 2001, 38 extra, pp. 242-246.

S. Santoso et al., "Association of the Platelet Glycoprotein la $C_{807}T$ Gene Polymorphism with Nonfatal Myocardial Infarction in Younger Patients," Blood, vol: 93, No. 8, 1999, pp. 2449- 2453.

Office Action mailed on Jan. 22, 2008, issued in the proceeding of a corresponding Japanese patent application No. 2002-233041 and Its partial translation.

* cited by examiner

Fig.1

| gene | polymorphism | gene | polymorphism |
|---|---|---|---|
| Angiotensin converting enzyme | I/D in intron 16 | Insulin receptor substrate-1 | 3494G→A (Gly972Arg) |
| Angiotensin II type I receptor | -535C→T | Interleukin-10 | -1082G→A |
| Angiotensinogen | -6G→A | | -819T→C |
| Apolipoprotein A1 | -75G→A | | -592A→C |
| | 83C→T | Interleukin-1α | -889C→T |
| Apolipoprotein B | I/D in signal peptide | Interleukin-1β | -511C→T |
| Apolipoprotein C-III | -482C→T | | 3953C→T |
| | 1100C→T | Interleukin-6 | -634C→G |
| Apolipoprotein E | -491A→T | | -174G→C |
| | -219G→T | LDL receptor related protein | 766C→T |
| | 3932T→C (Cys112Arg) | Leptin | -1887C→A |
| | 4070C→T (Arg158Cys) | Lipoprotein lipase | 280G→A (Asp9Asn) |
| Apolipoprotein (a) | 93C→T | | 1127A→G (Asn291Ser) |
| | 121G→A | Manganese superoxide dismutase | 47C→T (Ala16Val) |
| | 11764A→C (Thr12Pro) | | 173T→C (Ile58Thr) |
| ATP-binding cassette transporter 1 | -477C→T | Matrix Gla protein | -7G→A |
| | 1051G→A (Arg219Lys) | | 7158A→G (Thr83Ala) |
| Atrial natriuretic peptide | 664G→A (Val7Met) | Metalloproteinase-1 (collagenase) | −1607G→GG |
| Atrial natriuretic peptide clearance receptor | -55A→C | Metalloproteinase-12 (macrophage elastase) | -82A→G |
| β2-adrenergic receptor | 46A→G (Arg16Gly) | Methionine synthase | 2756A→G (Asp919Gly) |
| | 79C→G (Gln27Glu) | Methylenetetrahydrofolate reductase | 677C→T (Ala222Val) |
| | 491C→T (Thr164Ile) | Monocyte chemoattractant protein-1 | -2518G→A |
| β3-adrenergic receptor | 190T→C (Trp64Arg) | NADH/NADPH oxidase p22 phox | 242C→T (His72Tyr) |
| β-Fibrinogen | -854G→A | Neuropeptide Y | 1128T→C (Leu7Pro) |
| | -455G→A | Paraoxonase | -107T→C |
| | 148C→T | | 172A→T (Met55Leu) |
| | 8059G→A (Arg448Lys) | | 584G→A (Gln192Arg) |
| CD14 receptor | -260C→T | PECAM1 (CD31) | 1454C→G (Leu125Val) |

Fig.2

| | | | |
|---|---|---|---|
| Chemokine receptor 2 | 190G→A (Val64Ile) | PECAM1 (CD31) | 4428G→A (Ser563Asn) |
| Cholesterol ester transfer protein | 1061A→G (Ile405Val) | Peroxisome proliferator-activated receptor-α | 696C→G (Leu162Val) |
| | 1163A→G (Asp442Gly) | Peroxisome proliferator-activated receptor -γ2 | 34C→G (Pro12Ala) |
| | 1200G→A (Arg451Gln) | | 344C→A (Pro115Gln) |
| Coagulation factor V | 1691G→A (Arg506Gln) | Plasminogen-activator inhibitor-1 | –668/4G→5G |
| Coagulation factor VII | 11496G→A (Arg353Glu) | Platelet-activating factor acetylhydrolase | 994G→T (Val279Phe) |
| Coagulation factor XII | 46C→T | Prothrombin | 20210G→A |
| Coagulation factor XIII A-subunit | 163G→T (Val34Leu) | P-selectin | 76666A→C (Thr715Pro) |
| Connexin 37 | 1019C→T (Pro319Ser) | Scavenger receptor-BI | 4G→A (Gly2Ser) |
| Endothelial nitric oxide synthase | -786T→C | | 403G→A (Val135Ile) |
| | 894G→T (Glu298Asp) | Serotonin 2A receptor | 102T→C |
| Endothelin-1 | 5665G→T (Lys198Asn) | Stromelysin-1 | –1171/5A→6A |
| E-selectin | 98G→T | Thrombomodulin | -33G→A |
| | 561A→C (Ser128Arg) | | -10GG→TA |
| | 1839C→T (Leu554Phe) | | 845G→A (Ala25Thr) |
| Extracellular superoxide dismutase | 5775C→G (Arg213Gly) | | 2136C→T (Ala455Val) |
| Fatty acid-binding protein 2 | 2445G→A (Ala54Thr) | Thrombopoietin | 5713A→G |
| Fractalkine receptor | 84635G→A (Val249Ile) | Thrombospondin 1 | 2210A→G (Asn700Ser) |
| Glycoprotein Ia | 807C→T | Thrombospondin 4 | 1186G→C (Ala387Pro) |
| | 873G→A | Tissue factor pathway inhibitor | 874G→A (Val264Met) |
| | 1648A→G (Lys505Glu) | Transforming growth factor-β1 | -509C→T |
| Glycoprotein Ibα | 1018C→T (Thr145Met) | | 869T→C (Leu10Pro) |
| Glycoprotein IIIa | 1565T→C (Leu33Pro) | Tumor necrosis factor-α | -863C→A |
| Glycoprotein PC-1 | 97A→C (Lys121Gln) | | -850C→T |
| G-protein β3 subunit | 825C→T (splice variant) | | -308G→A |
| Hemochromatosis-associated protein | 845G→A (Cys282Tyr) | | -238G→A |
| Hepatic lipase | -480C→T | von Willebrand factor | -1234C→T |
| | -250G→A | | -1051G→A |

Fig.3

| Gene | SNP | Lebels | Primers (5'→3') | Cycles | Probes (5'→3') | Formamide |
|---|---|---|---|---|---|---|
| Angiotensinogen | -6G→A | TxR | CGGCAGCTTCTTCCCXCG | | | |
| | | FITC | CGGCAGCTTCTTCCCXTG | 35 | | |
| | | Biotin | CCACCCCTCAGCTATAAATAGG | | | |
| Apolipoprotein C-III | -482C→T | | CGGAGCCACTGATGCXCG | | AGCCACTGATGCXCGGTCT | |
| | | | CGGAGCCACTGATGCXTG | 35 | AGCCACTGATGCXTGGTCT | 30% |
| | | Biotin | TGTTTGGAGTAAAGGCACAGAA | | | |
| Apolipoprotein E | 3932T→C | FITC | GGACATGGAGGACGTXCG | | | |
| | | TxR | CGGACATGGAGGACGTXTG | 40 | | |
| | | Biotin | CGCGGTACTGCACCAGGC | | | |
| E-selectin | 561A→C | | ACATTCACCGTGGCCAXTG | | CACCGTGGCCAXTGCAGGAT | |
| | | | CATTCACCGTGGCCAXGG | 35 | CACCGTGGCCAXGGCAGGAT | 45% |
| | | Biotin | AGCTGCCTGTACCAATACATCC | | | |
| Fatty acid-binding protein 2 | 2445G→A | | TCACAGTCAAAGAATCAAGXGC | | GAATCAAGXGCTTTTCGAAACATT | |
| | | | ATTCACAGTCAAAGAATCAAGXAC | 40 | GAATCAAGXACTTTTCGAAACATT | 37.5% |
| | | Biotin | CAAAAACAACTTCAATGTTTCGA | | | |
| G-protein β3 subunit | 825C→T | TxR | TCTGCGGCATCACGTXCG | | | |
| | | FITC | TCTGCGGCATCACGTXTG | 35 | | |
| | | Biotin | GAATAGTAGGCGGCCACTGA | | | |
| Glycoprotein Ia | 1648A→G | FITC | GAGTCTACCTGTTTACTATCAAXAA | | | |
| | | TxR | GAGTCTACCTGTTTACTATCAAXGA | 40 | | |
| | | Biotin | ACCAGTACTAAAGCAAATTAAACT | | | |
| Glycoprotein Ibα | 1018C→T | FITC | CCCAGGGCTCCTGXCG | | | |
| | | TxR | CCCCAGGGCTCCTGXTG | 40 | | |
| | | Biotin | TGAGCTTCTCCAGCTTGGGTG | | | |
| Paraoxonase | 584G→A | FITC | ACCCAAATACATCTCCCAGGAXCG | | | |
| | | TxR | AACCCAAATACATCTCCCAGGXCT | 35 | | |
| | | Biotin | GAATGATATTGTTGCTGTGGGAC | | | |
| Plasminogen-activator inhibitor-1 | -668/4G→5G | | GGCACAGAGAGAGTCTGGACACG | | TGGACACGTGGGGGAGTCAG | |
| | | Biotin | GGCCGCCTCCGATGATACA | 35 | TGGACACGTGGGGAGTCAGC | 45% |

Fig.4

| | | | | |
|---|---|---|---|---|
| Platelet-activating factor acetylhydrolase | 994G→T | FITC | TTCTTTTGGTGGAGCAACXGT | |
| | | TxR | ATTCTTTTGGTGGAGCAACXTT | 40 |
| | | Biotin | TCTTACCTGAATCTCTGATCTTCA | |
| Thrombomodulin | 2136C→T | FITC | CCCGACTCGGCCCTTXCC | |
| | | TxR | CCCGACTCGGCCCTTXTC | 40 |
| | | Biotin | GTCACAGTCGGTGCCAATGT | |
| Thrombopoietin | 5713A→G | FITC | CCGACATCAGCATTGTCTXAT | |
| | | TxR | CCGACATCAGCATTGTCTXGT | 35 |
| | | Biotin | CTGCAGGGAAGGGAGCTGT | |
| Thrombospondin 4 | 1186G→C | TxR | CGAGTTGGGAACGCACXCT | |
| | | FITC | CGAGTTGGGAACGCACXGT | 35 |
| | | Biotin | GGTCTGCACTGACATTGATGAG | |
| Tumor necrosis factor-α | -863C→A | TxR | GGCCCTGTCTTCGTTAAXGG | |
| | | FITC | ATGGCCCTGTCTTCGTTAAXTG | 35 |
| | | Biotin | CCAGGGCTATGGAAGTCGAGTATC | |

Fig.5

| Gene | SNP | Gene | SNP |
|---|---|---|---|
| Men | | Women | |
| Angiotensinogen | -6G→A | Apolipoprotein C-III | -482C→T |
| Apolipoprotein C-III | -482C→T | Apolipoprotein E | 3932T→C |
| Apolipoprotein C-III | 1100C→T | Apolipoprotein E | 4070C→T |
| Apolipoprotein E | -219G→T | ATP-binding cassette transporter 1 | 1051G→A |
| Apolipoprotein E | 4070C→T | CD14 receptor | -260C→T |
| Chemokine receptor 2 | 190G→A | Connexin 37 | 1019C→T |
| Connexin 37 | 1019C→T | E-selectin | 561A→C |
| Endothelial nitric oxide synthase | -786T→C | Endothelial nitric oxide synthase | -786T→C |
| G-protein β3 subunit | 825C→T | Endothelin-1 | 5665G→T |
| Glycoprotein Ia | 1648A→G | Fatty acid-binding protein 2 | 2445G→A |
| Interleukin-10 | -819T→C | Glycoprotein Ibα | 1018C→T |
| Interleukin-10 | -592A→C | Insulin receptor substrate-1 | 3494G→A |
| NADH/NADPH oxidase p22 phox | 242C→T | Interleukin-6 | -634C→G |
| Platelet-activating factor acetylhydrolase | 994G→T | Paraoxonase | 584G→A |
| Thrombomodulin | 2136C→T | Plasminogen-activator inhibitor-1 | -668/4G→5G |
| Thrombopoietin | 5713A→G | Stromelysin-1 | -1171/5A→6A |
| Thrombospondin 4 | 1186G→C | Tumor necrosis factor-α | -850C→T |
| Transforming growth factor-β1 | 869T→C | Tumor necrosis factor-α | -238G→A |
| Tumor necrosis factor-α | -863C→A | | |

Fig.6

| | POBA (n = 910) | | Stent implantation (n = 710) | |
|---|---|---|---|---|
| | No restenosis (n = 525) | Restenosis (n = 385) | No restenosis (n = 527) | Restenosis (n = 183) |
| Age (years) | 58.5 ± 9.5 | 55.9 ± 9.6*1 | 56.8 ± 8.8 | 53.8 ± 9.9*2 |
| Body mass index ($kg/m^2$) | 24.0 ± 2.9 | 24.2 ± 2.8 | 24.0 ± 3.0 | 23.5 ± 2.9 |
| Smoking (%) | 77.0 | 81.3 | 88.4 | 94.5‡ |
| Hypertension (%) | 68.0 | 79.5*2 | 77.8 | 83.1 |
| Systolic BP (mmHg) | 147.5 ± 25.3 | 152.6 ± 26.4*4 | 149.1 ± 25.9 | 156.4 ± 24.4*4 |
| Diastolic BP (mmHg) | 80.9 ± 14.0 | 85.4 ± 17.1*1 | 82.7 ± 15.2 | 87.0 ± 17.3*4 |
| Diabetes mellitus (%) | 32.4 | 40.0*3 | 41.4 | 50.3*3 |
| Fasting blood sugar (g/dL) | 119.5 ± 54.5 | 123.5 ± 47.8 | 118.6 ± 43.7 | 125.1 ± 54.2 |
| Hypercholesterolemia (%) | 57.3 | 56.9 | 56.9 | 55.2 |
| Total cholesterol (mg/dL) | 208.9 ± 43.0 | 210.9 ± 45.0 | 210.7 ± 48.1 | 203.0 ± 47.1 |
| Triglycerides (mg/dL) | 158.5 ± 101.9 | 147.0 ± 93.6 | 152.1 ± 129.9 | 139.0 ± 75.3 |
| HDL-cholesterol (mg/dL) | 46.4 ± 13.1 | 44.3 ± 13.6 | 44.4 ± 12.2 | 44.3 ± 14.1 |
| Hyperuricemia (%) | 23.0 | 18.4 | 14.4 | 22.4*3 |
| Uric acid (mg/dL) | 6.0 ± 1.6 | 5.8 ± 1.6 | 5.8 ± 1.7 | 5.6 ± 1.4 |
| Coronary lesions | | | | |
| Right coronary artery (%) | 30.5 | 28.3 | 32.4 | 39.9 |
| Left anterior descendent (%) | 45.1 | 48.6 | 52.8 | 45.4 |
| Left circumflex (%) | 24.4 | 23.1 | 14.8 | 14.8 |

Fig.7

| | POBA (n = 480) | | Stent implantation (n = 291) | |
|---|---|---|---|---|
| | No restenosis (n = 286) | Restenosis (n = 194) | No restenosis (n = 204) | Restenosis (n = 87) |
| Age (years) | 63.1 ± 10.2 | 65.8 ± 7.7*1 | 63.2 ± 8.8 | 67.0 ± 9.8*1 |
| Body mass index ($kg/m^2$) | 23.7 ± 3.4 | 23.4 ± 3.1 | 23.9 ± 3.3 | 23.5 ± 2.6 |
| Smoking (%) | 15.4 | 24.7*2 | 32.4 | 20.7*2 |
| Hypertension (%) | 65.0 | 62.9 | 85.3 | 55.2*3 |
| Systolic BP (mmHg) | 149.4 ± 28.3 | 148.2 ± 27.5 | 148.4 ± 31.0 | 156.1 ± 28.7 |
| Diastolic BP (mmHg) | 79.0 ± 15.5 | 77.8 ± 15.6 | 78.9 ± 14.0 | 84.5 ± 14.6*2 |
| Diabetes mellitus (%) | 32.2 | 45.4*1 | 42.6 | 79.3*3 |
| Fasting blood sugar (g/dL) | 121.6 ± 53.4 | 141.3 ± 65.4*1 | 135.9 ± 72.0 | 152.3 ± 57.0*4 |
| Hypercholesterolemia (%) | 69.9 | 63.9 | 70.6 | 72.4 |
| Total cholesterol (mg/dL) | 211.7 ± 38.4 | 213.1 ± 44.5 | 219.1 ± 46.6 | 218.7 ± 40.2 |
| Triglycerides (mg/dL) | 127.8 ± 61.8 | 129.6 ± 73.0 | 134.2 ± 82.7 | 161.0 ± 119.2*2 |
| HDL-cholesterol (mg/dL) | 47.4 ± 13.4 | 46.8 ± 14.6 | 56.2 ± 17.4 | 54.4 ± 13.5 |
| Hyperuricemia (%) | 17.5 | 22.7 | 33.8 | 17.2*1 |
| Uric acid (mg/dL) | 4.6 ±1.2 | 4.6 ± 1.5 | 4.9 ± 1.4 | 4.8 ± 1.3 |
| Coronary arteries | | | | |
| Right coronary (%) | 22.7 | 47.9*3 | 45.6 | 34.5 |
| Left anterior descendent (%) | 41.6 | 41.8 | 39.7 | 55.2*2 |
| Left circumflex (%) | 35.7 | 10.3‡ | 14.7 | 10.3 |

Fig.8

| Gene | SNP | Dominant | | Recessive | | Additive | |
|---|---|---|---|---|---|---|---|
| | | *P* | OR (95% CI) | *P* | OR (95% CI) | *P* | OR (95% CI) |
| POBA | | | | | | | |
| Glycoprotein Ia | 1684A→G | 0.7410 | | **0.0012** | 0.5 (0.3-0.8) | 0.7401 | |
| G-protein β3 subunit | 825C→T | 0.2916 | | **0.0033** | 1.6 (1.2-2.3) | 0.0119 | 1.6 (1.1-2.4) |
| Tumor necrosis factor-α | -863C→A | **0.0066** | 1.5 (1.1-2.1) | 0.8408 | | 0.0039 | 1.6 (1.2-2.3) |
| Apolipoprotein C-III | -482C→T | **0.0096** | 1.5 (1.1-2.1) | 0.1986 | | 0.0216 | 1.6 (1.1-2.4) |
| Apolipoprotein E | 3932T→C | **0.0101** | 1.6 (1.1-2.4) | 0.7705 | | 0.0103 | 1.7 (1.1-2.5) |
| Angiotensinogen | -6G→A | **0.0307** | 0.4 (0.2-0.9) | 0.4615 | | 0.0306 | 0.4 (0.17-0.90) |
| Stent implantation | | | | | | | |
| Tumor necrosis factor-α | -863C→A | 0.0415 | 1.5 (1.0-2.1) | **0.0142** | 2.0 (1.1-3.6) | 0.0082 | 2.2 (1.2-3.9) |
| Thrombomodulin | 2136C→T | **0.0143** | 1.6 (1.1-2.3) | 0.2937 | | 0.0241 | 1.6 (1.1-2.3) |
| Thrombospondin 4 | 1186G→C | **0.0229** | 1.7 (1.1-2.7) | | | 0.0229 | 1.7 (1.1-2.7) |
| Platelet-activating factor acetylhydrolase | 994G→T | **0.0475** | 1.5 (1.0-2.2) | 0.3905 | | 0.0666 | |
| Thrombopoietin | 5713A→G | 0.3159 | | **0.0499** | 1.5 (1.0-2.1) | 0.8858 | |

Fig.9

| Gene | SNP | Dominant | | Recessive | | Additive | |
|---|---|---|---|---|---|---|---|
| | | *P* | OR (95% CI) | *P* | OR (95% CI) | *P* | OR (95% CI) |
| POBA | | | | | | | |
| Fatty acid-binding protein 2 | 2445G→A | **0.0001** | 2.3 (1.5-3.6) | 0.0014 | 2.7 (1.5-4.9) | 0.0001 | 3.8 (2.0-7.4) |
| Plasminogen-activator inhibitor-1 | -668/4G→5G | **0.0091** | 1.8 (1.2-2.7) | 0.6798 | | 0.0030 | 2.0 (1.3-3.1) |
| Glycoprotein Ibα | 1018C→T | **0.0117** | 1.8 (1.1-2.8) | 0.7326 | | 0.0003 | 2.4 (1.5-3.9) |
| Paraoxonase | 584G→A | **0.0174** | 1.6 (1.1-2.4) | 0.0270 | 2.4 (1.1-5.1) | 0.0098 | 2.8 (1.3-6.2) |
| E-selectin | 561A→C | **0.0249** | 2.9 (1.2-7.7) | | | 0.0249 | 2.9 (1.2-7.7) |
| Apolipoprotein E | 3932T→C | **0.0462** | 1.7 (1.0-2.8) | 0.5308 | | 0.0691 | |
| Stent implantation | | | | | | | |
| Plasminogen-activator inhibitor-1 | -668/4G→5G | **0.0013** | 3.2 (1.6-6.5) | 0.6063 | | 0.0003 | 4.2 (2.0-9.3) |
| Paraoxonase | 584G→A | **0.0083** | 2.5 (1.3-4.9) | 0.4102 | | 0.0114 | 2.5 (1.2-5.0) |
| Glycoprotein Ibα | 1018C→T | **0.0187** | 2.6 (1.2-5.7) | | | 0.0187 | 2.6 (1.2-5.7) |
| Apolipoprotein E | 3932T→C | **0.0299** | 2.5 (1.1-5.9) | 0.8671 | | 0.0046 | 3.6 (1.5-8.7) |
| Apolipoprotein C-III | -482C→T | 0.0602 | | **0.0337** | 2.3 (1.1-5.0) | 0.7313 | |

Fig.10

| Gene | chromosomal locus | SNP | Genetic model | *P* | Odds ratio | 95% CI |
|---|---|---|---|---|---|---|
| POBA | | | | | | |
| Apolipoprotein E | 19q13.2 | 3932T→C | *CC* + *TC* versus *TT* | 0.0035 | 1.80 | 1.21-2.66 |
| Glycoprotein Ia | 5q23-q31 | 1684A→G | *GG* versus *AG* + *AA* | 0.0162 | 0.57 | 0.37-0.90 |
| Tumor necrosis factor-α | 6p21.3 | -863C→A | *AA* + *CA* versus *CC* | 0.0075 | 1.54 | 1.12-2.11 |
| G-protein β3 subunit | 12p13 | 825C→T | *TT* versus *CT* + *CC* | 0.0187 | 1.51 | 1.07-2.12 |
| Apolipoprotein C-III | 11q23 | -482C→T | *TT* + *CT* versus *CC* | 0.0236 | 1.44 | 1.05-1.98 |
| Angiotensinogen | 1q42-q43 | -6G→A | *AA* + *GA* versus *GG* | 0.4384 | 0.70 | 0.29-1.70 |
| Stent implantation | | | | | | |
| Thrombospondin 4 | 5q13 | 1186G→C | *CC* + *GC* versus *GG* | 0.0217 | 1.75 | 1.08-2.81 |
| Tumor necrosis factor-α | 6p21.3 | -863C→A | *AA* versus *CA* + *CC* | 0.1140 | 1.61 | 0.89-2.91 |
| Thrombomodulin | 20p11.2 | 2136C→T | *TT* + *CT* versus *CC* | 0.0767 | 1.42 | 0.96-2.08 |
| Thrombopoietin | 3q26.3-q27 | 5713A→G | *GG* versus *AG* + *AA* | 0.1266 | 1.36 | 0.92-2.02 |
| Platelet-acrivating factor acetylhydrolase | 6p21.2-p12 | 994G→T | *TT* + *GT* versus *GG* | 0.3460 | 1.22 | 0.81-1.84 |

Fig.11

| Gene | chromosomal locus | SNP | Genetic model | *P* | Odds ratio | 95% CI |
|---|---|---|---|---|---|---|
| POBA | | | | | | |
| E-selectin | 1q23-q25 | 561A→C | *CC* + *AC* versus *AA* | 0.0227 | 3.54 | 1.19-10.52 |
| Fatty acid-binding protein 2 | 4q28-q31 | 2445G→A | *AA* + *GA* versus *GG* | 0.0002 | 2.42 | 1.52-3.85 |
| Glycoprotein Ibα | 22q11.2 | 1018C→T | *TT* + *CT* versus *CC* | 0.0111 | 1.86 | 1.15-3.02 |
| Plasminogen activator inhibitor-1 | 7q21.3-q22 | -668/4G→5G | *5G/5G* + *4G/5G* versus *4G/4G* | 0.0475 | 1.62 | 1.01-2.60 |
| Paraoxonase | 7q21.3 | 584G→A | *AA* + *GA* versus *GG* | 0.0994 | 1.45 | 0.93-2.25 |
| Apolipoprotein E | 19q13.2 | 3932T→C | *CC* + *TC* versus *TT* | 0.5569 | 1.19 | 0.661-2.16 |
| Stent implantation | | | | | | |
| Plasminogen activator inhibitor-1 | 7q21.3-q22 | -668/4G→5G | *5G/5G* + *4G/5G* versus *4G/4G* | 0.0006 | 3.88 | 1.78-8.45 |
| Apolipoprotein C-III | 11q23 | -482C→T | *TT* versus *CT* + *CC* | 0.0100 | 3.11 | 1.31-7.38 |
| Paraoxonase | 7q21.3 | 584G→A | *AA* + *GA* versus *GG* | 0.0116 | 2.67 | 1.24-5.72 |
| Glycoprotein Ibα | 22q11.2 | 1018C→T | *TT* + *CT* versus *CC* | 0.0754 | 2.23 | 0.92-5.42 |
| Apolipoprotein E | 19q13.2 | 3932T→C | *CC* + *TC* versus *TT* | 0.3174 | 1.64 | 0.62-4.35 |

Fig.12

| Apolipoprotein E (0 = *TT*, 1 = *TC* = *CC*) | Glycoprotein Ia (0 = *AA* + *AG*, 1 = *GG*) | Tumor necrosis factor-α (0 = *CC*, 1 = *CA* = *AA*) | G-protein β3 subunit (0 = *CC* = *CT*, 1 = *TT*) | Apolipoprotein C-III (0 = *CC*, 1 = *CT* = *TT*) | Odds ratio |
|---|---|---|---|---|---|
| 1 | 0 | 1 | 1 | 1 | 10.55 |
| 1 | 0 | 1 | 1 | 0 | 7.33 |
| 1 | 0 | 1 | 0 | 1 | 6.99 |
| 1 | 0 | 1 | 0 | 0 | 4.85 |
| 1 | 0 | 0 | 1 | 1 | 6.85 |
| 1 | 0 | 0 | 1 | 0 | 4.76 |
| 1 | 0 | 0 | 0 | 1 | 4.54 |
| 1 | 0 | 0 | 0 | 0 | 3.15 |
| 1 | 1 | 1 | 1 | 1 | 6.03 |
| 1 | 1 | 1 | 1 | 0 | 4.19 |
| 1 | 1 | 1 | 0 | 1 | 3.99 |
| 1 | 1 | 1 | 0 | 0 | 2.77 |
| 1 | 1 | 0 | 1 | 1 | 3.91 |
| 1 | 1 | 0 | 1 | 0 | 2.72 |
| 1 | 1 | 0 | 0 | 1 | 2.59 |
| 1 | 1 | 0 | 0 | 0 | 1.80 |
| 0 | 0 | 1 | 1 | 1 | 5.86 |
| 0 | 0 | 1 | 1 | 0 | 4.07 |
| 0 | 0 | 1 | 0 | 1 | 3.88 |
| 0 | 0 | 1 | 0 | 0 | 2.70 |
| 0 | 0 | 0 | 1 | 1 | 3.81 |
| 0 | 0 | 0 | 1 | 0 | 2.64 |
| 0 | 0 | 0 | 0 | 1 | 2.52 |
| 0 | 0 | 0 | 0 | 0 | 1.75 |
| 0 | 1 | 1 | 1 | 1 | 3.35 |
| 0 | 1 | 1 | 1 | 0 | 2.33 |
| 0 | 1 | 1 | 0 | 1 | 2.22 |
| 0 | 1 | 1 | 0 | 0 | 1.54 |
| 0 | 1 | 0 | 1 | 1 | 2.17 |
| 0 | 1 | 0 | 1 | 0 | 1.51 |
| 0 | 1 | 0 | 0 | 1 | 1.44 |
| 0 | 1 | 0 | 0 | 0 | 1.00 |

Fig.13

| Thrombospondin 4 (0 = *GG*, 1 = *GC* = *CC*) | Tumor necrosis factor-α (0 = *CC* + *CA*, 1 = *AA* | Thrombomodulin (0 = *CC*, 1 = *CT* = *TT*) | Thrombopoietin (0 = *AA* = *AG*, 1 = *GG*) | Platelet-activating factor acetylhydrolase (0 = *GG*, 1 = *GT* = *TT*) | Odds ratio |
|---|---|---|---|---|---|
| 1 | 1 | 1 | 1 | 1 | 6.64 |
| 1 | 1 | 1 | 1 | 0 | 5.44 |
| 1 | 1 | 1 | 0 | 1 | 4.88 |
| 1 | 1 | 1 | 0 | 0 | 4.00 |
| 1 | 1 | 0 | 1 | 1 | 4.67 |
| 1 | 1 | 0 | 1 | 0 | 3.83 |
| 1 | 1 | 0 | 0 | 1 | 3.44 |
| 1 | 1 | 0 | 0 | 0 | 2.82 |
| 1 | 0 | 1 | 1 | 1 | 4.12 |
| 1 | 0 | 1 | 1 | 0 | 3.38 |
| 1 | 0 | 1 | 0 | 1 | 3.03 |
| 1 | 0 | 1 | 0 | 0 | 2.49 |
| 1 | 0 | 0 | 1 | 1 | 2.90 |
| 1 | 0 | 0 | 1 | 0 | 2.38 |
| 1 | 0 | 0 | 0 | 1 | 2.14 |
| 1 | 0 | 0 | 0 | 0 | 1.75 |
| 0 | 1 | 1 | 1 | 1 | 3.79 |
| 0 | 1 | 1 | 1 | 0 | 3.11 |
| 0 | 1 | 1 | 0 | 1 | 2.79 |
| 0 | 1 | 1 | 0 | 0 | 2.29 |
| 0 | 1 | 0 | 1 | 1 | 2.67 |
| 0 | 1 | 0 | 1 | 0 | 2.19 |
| 0 | 1 | 0 | 0 | 1 | 1.96 |
| 0 | 1 | 0 | 0 | 0 | 1.61 |
| 0 | 0 | 1 | 1 | 1 | 2.36 |
| 0 | 0 | 1 | 1 | 0 | 1.93 |
| 0 | 0 | 1 | 0 | 1 | 1.73 |
| 0 | 0 | 1 | 0 | 0 | 1.42 |
| 0 | 0 | 0 | 1 | 1 | 1.66 |
| 0 | 0 | 0 | 1 | 0 | 1.36 |
| 0 | 0 | 0 | 0 | 1 | 1.22 |
| 0 | 0 | 0 | 0 | 0 | 1.00 |

Fig.14

| E-selectin (0 = *AA*, 1 = *AC* = *CC*) | Fatty acid-binding protein 2 (0 = *GG*, 1 = *GA* + *AA*) | Glycoprotein Ibα (0 = *CC*, 1 = *CT* = *TT*) | Plasminogen activator inhibitor-1 (0 = *4G/4G*, 1 = *4G/5G* = *5G/5G*) | Paraoxonase (0 = *GG*, 1 = *GA* = *AA*) | Odds ratio |
|---|---|---|---|---|---|
| 1 | 1 | 1 | 1 | 1 | 37.43 |
| 1 | 1 | 1 | 1 | 0 | 25.81 |
| 1 | 1 | 1 | 0 | 1 | 23.10 |
| 1 | 1 | 1 | 0 | 0 | 15.93 |
| 1 | 1 | 0 | 1 | 1 | 20.12 |
| 1 | 1 | 0 | 1 | 0 | 13.88 |
| 1 | 1 | 0 | 0 | 1 | 12.42 |
| 1 | 1 | 0 | 0 | 0 | 8.57 |
| 1 | 0 | 1 | 1 | 1 | 15.47 |
| 1 | 0 | 1 | 1 | 0 | 10.67 |
| 1 | 0 | 1 | 0 | 1 | 9.55 |
| 1 | 0 | 1 | 0 | 0 | 6.58 |
| 1 | 0 | 0 | 1 | 1 | 8.32 |
| 1 | 0 | 0 | 1 | 0 | 5.74 |
| 1 | 0 | 0 | 0 | 1 | 5.13 |
| 1 | 0 | 0 | 0 | 0 | 3.54 |
| 0 | 1 | 1 | 1 | 1 | 10.57 |
| 0 | 1 | 1 | 1 | 0 | 7.29 |
| 0 | 1 | 1 | 0 | 1 | 6.53 |
| 0 | 1 | 1 | 0 | 0 | 4.50 |
| 0 | 1 | 0 | 1 | 1 | 5.69 |
| 0 | 1 | 0 | 1 | 0 | 3.92 |
| 0 | 1 | 0 | 0 | 1 | 3.51 |
| 0 | 1 | 0 | 0 | 0 | 2.42 |
| 0 | 0 | 1 | 1 | 1 | 4.37 |
| 0 | 0 | 1 | 1 | 0 | 3.01 |
| 0 | 0 | 1 | 0 | 1 | 2.70 |
| 0 | 0 | 1 | 0 | 0 | 1.86 |
| 0 | 0 | 0 | 1 | 1 | 2.35 |
| 0 | 0 | 0 | 1 | 0 | 1.62 |
| 0 | 0 | 0 | 0 | 1 | 1.45 |
| 0 | 0 | 0 | 0 | 0 | 1.00 |

Fig.15

| Plasminogen activator inhibitor-1 (0 = *4G/4G*, 1 = *4G/5G* = *5G/5G*) | Apolipoprotein C-III (0 = *CC* + *CT*, 1 = *TT*) | Paraoxonase (0 = *GG*, 1 = *GA* = *AA*) | Glycoprotein Ibα (0 = *CC*, 1 = *CT* = *TT*) | Apolipoprotein E (0 = *TT*, 1 = *TC* = *CC*) | Odds ratio |
|---|---|---|---|---|---|
| 1 | 1 | 1 | 1 | 1 | 117.83 |
| 1 | 1 | 1 | 1 | 0 | 71.85 |
| 1 | 1 | 1 | 0 | 1 | 52.84 |
| 1 | 1 | 1 | 0 | 0 | 32.22 |
| 1 | 1 | 0 | 1 | 1 | 44.13 |
| 1 | 1 | 0 | 1 | 0 | 26.91 |
| 1 | 1 | 0 | 0 | 1 | 19.79 |
| 1 | 1 | 0 | 0 | 0 | 12.07 |
| 1 | 0 | 1 | 1 | 1 | 37.89 |
| 1 | 0 | 1 | 1 | 0 | 23.10 |
| 1 | 0 | 1 | 0 | 1 | 16.99 |
| 1 | 0 | 1 | 0 | 0 | 10.36 |
| 1 | 0 | 0 | 1 | 1 | 14.19 |
| 1 | 0 | 0 | 1 | 0 | 8.65 |
| 1 | 0 | 0 | 0 | 1 | 6.36 |
| 1 | 0 | 0 | 0 | 0 | 3.88 |
| 0 | 1 | 1 | 1 | 1 | 30.37 |
| 0 | 1 | 1 | 1 | 0 | 18.52 |
| 0 | 1 | 1 | 0 | 1 | 13.62 |
| 0 | 1 | 1 | 0 | 0 | 8.30 |
| 0 | 1 | 0 | 1 | 1 | 11.37 |
| 0 | 1 | 0 | 1 | 0 | 6.94 |
| 0 | 1 | 0 | 0 | 1 | 5.10 |
| 0 | 1 | 0 | 0 | 0 | 3.11 |
| 0 | 0 | 1 | 1 | 1 | 9.76 |
| 0 | 0 | 1 | 1 | 0 | 5.95 |
| 0 | 0 | 1 | 0 | 1 | 4.38 |
| 0 | 0 | 1 | 0 | 0 | 2.67 |
| 0 | 0 | 0 | 1 | 1 | 3.66 |
| 0 | 0 | 0 | 1 | 0 | 2.23 |
| 0 | 0 | 0 | 0 | 1 | 1.64 |
| 0 | 0 | 0 | 0 | 0 | 1.00 |

METHOD OF DIAGNOSING RISK OF RESTENOSIS AFTER CORONARY ANGIOPLASTY

TECHNICAL FIELD

The present invention relates to a detection method using genes associated with restenosis after coronary angioplasty. More particularly, it relates to a detection method using a plurality of gene polymorphisms associated with restenosis after coronary angioplasty and to a kit used for the method. The present invention can be used for, for example, diagnosing a risk of restenosis after coronary angioplasty.

BACKGROUND ART

Although coronary angioplasties have been carried out widely as a treatment for coronary artery diseases, restenosis is a large problem (McBride W, Lange R A, Hillis L D. Restenosis after successful coronary angioplasty. Pathophysiology and prevention. N Engl J Med 1998;318:1734-7). The use of intra-coronary stents reduces the incidence of restenosis, however, restenosis is still observed in 10 to 20% (Serruys P W, de Jaegere P, Kiemeneij F, et al. A comparison of balloon-expandable-stent implantation with balloon angioplasty in patients with coronary artery disease. Benestent Study Group. N Engl J Med 1994;331:489-95.). A number of clinical and angiographic findings, including hypertension, diabetes mellitus, hyperlipidemia, unstable angina, severe coronary artery stenosis and long stenosis lesions, have been reported to be associated with an increased risk of restenosis after coronary angioplasty (Hirshfeld J W Jr, Schwartz J S, Jugo R, et al. Restenosis after coronary angioplasty: a multivariate statistical model to relate lesion and procedure variables to restenosis. The M-HEART Investigators. J Am Coll Cardiol 1991;18:647-56.; Weintraub W S, Kosinski A S, Brown C L 3rd, King S B 3rd. Can restenosis after coronary angioplasty be predicted from clinical variables? J Am Coll Cardiol 1993;21:6-14.; Stein B, Weintraub W S, Gebhart S P, et al. Influence of diabetes mellitus on early and late outcome after percutaneous transluminal coronary angioplasty. Circulation 1995;91:979-89.; Violaris A G, Melkert R, Serruys P W. Long-term luminal renarrowing after successful elective coronary angioplasty of total occlusions. A quantitative angiographic analysis. Circulation 1995;91:2140-50.). The molecular mechanisms underlying restenosis, however, remain to be elucidated. Intra-coronary ultrasound studies in humans suggest that chronic remodeling (vascular constriction) is the major mechanism of restenosis after balloon dilatation (Mintz G S, Popma J J, Pichard A D, et al. Arterial remodeling after coronary angioplasty: a serial intravascular ultrasound study. Circulation 1996;94:35-43.), whereas neointimal hyperplasia is the most important mechanism in in-stent restenosis (Hoffmann R, Mintz G S, Dussaillant G R, et al. Patterns and mechanisms of in-stent restenosis. A serial intravascular ultrasound study. Circulation 1996;94:1247-54). One approach to preventing the development of restenosis after coronary angioplasty is to identify susceptibility genes. Although genetic epidemiological studies have revealed that several genetic polymorphisms, including those of angiotensin-converting enzyme (Amant C, Bauters C, Bodart J-C, et al. D allele of the angiotensin I-converting enzyme is a major risk factor for restenosis after coronary stenting. Circulation 1997;96:56-60.; Ribichini F, Steffenino G, Dellavalle A, et al. Plasma activity and insertion/deletion polymorphism of angiotensin I-converting enzyme: a major risk factor and a marker of risk for coronary stent restenosis. Circulation 1998;97:147-154.), angiotensinogen (Volzke H, Hertwig S, Rettig R, Motz W. The angiotensinogen gene 235T variant is associated with an increased risk of restenosis after percutaneous transluminal coronary angioplasty. Clin Sci 2000;99:19-25.), apolipoprotein E (van Bockxmeer F M, Mamotte C D S, Gibbons F R, Taylor R R. Apolipoprotein e4 homozygosity-a determinant of restenosis after coronary angioplasty. Atherosclerosis 1994;110:195-202.), platelet glycoprotein IIIa (Walter D H, Schachinger V, Elsner M, Dimmeler S, Zeiher A M. Platelet glycoprotein IIIa polymorphisms and risk of coronary stent thrombosis. Lancet 1997; 350: 1217-1219.), and stromelysin-1 (Humphries S, Bauters C, Meirhaeghe A, Luong L, Bertrand M, Amouyel P. The 5A6A polymorphism in the promoter of the stromelysin-1 (MMP3) as a risk factor for restenosis. Eur Heart J 2002;23:721-725.), have been reported to be associated with restenosis after balloon dilatation or in-stent restenosis, the genes that contribute to genetic susceptibility to restenosis remain to be identified definitively.

SUMMARY OF THE INVENTION

As mentioned above, a large number of association study between gene polymorphisms and restenosis after coronary angioplasty have been carried out previously. However, many studies have not reached a certain finding in terms of significance thereof. This is mainly because populations of subjects in many studies are not sufficient and not only gene polymorphisms but also environmental factors are different between races. Furthermore, even if the association with restenosis is recognized, in the analysis of large scale population, relative risk (odds ratio) is generally low.

The present invention was made on the basis of the above-mentioned background, and the object thereof is to provide a means of diagnosing genetic risk of restenosis after coronary angioplasty with high accuracy and high predictability.

To achieve the above-mentioned objects, the present inventors have extracted 71 genes which were estimated to be associated with coronary arteriosclerosis, coronary artery spasm, hypertension, diabetes mellitus, hyperlipidemia, etc., and mainly selected 112 polymorphisms which were predicted to be associated with functional changes of genes by the use of a plurality of public databases. Then, as to 112 polymorphisms of 71 genes, association study with respect to myocardial infarction was carried out in 445 myocardial cases and 464 controls. As a result, the present inventors have found 19 SNPs (single nucleotide polymorphisms) which were associated with myocardial infarction in men and 18 SNPs in women (Yamada Y, Izawa H, Ichihara S, et al. Genetic risk diagnosis system for myocardial infarction developed by a large scale association study of 112 gene polymorphisms in 5061 individuals (in press)). However, such polymorphisms also inluded candidate genes of restenosis after coronary angioplasty. Then, the present inventors performed a large scale association study on the association between these SNPs and restenosis after cornoary angioplasty. As a result, the present inventors succeeded in identifying ten SNPs which were associated with restenosis after coronary angioplasty in men and seven SNPs in women. In addition, analysis of the combination of these polymorphisms revealed maximal odds ratios of 15.09 and 44.54 for restenosis after balloon dilatation, and of 6.64 and 117.83 for in-stent restenosis in men and women, respectively, on the basis of the stepwise forward selection method of multivariate logistic regression analysis. In the analysis, the odds ratios were maximum among the odds ratios which had been reported in the past. Based on these results, it was possible to obtain a finding that by selecting a plurality of SNPs from these SNPs and using the combination of the results of analysis of each SNP, diagnosis of restenosis after coronary angioplasty can be carried out with high reliability and high predictability. The present invention was made based on the above findings and provides the following configuration.

[1] A method for detecting the genotype in a nucleic acid sample, comprising the following step (a):

(a) analyzing two or more polymorphisms selected from the group consisting of the following (1) to (6) in a nucleic acid sample:

(1) polymorphism at the base number position 3932 of the apolipoprotein E gene;

(2) polymorphism at the base number position 1648 of the glycoprotein Ia gene;

(3) polymorphism at the base number position −863 of the tumor necrosis factor-α gene;

(4) polymorphism at the base number position 825 of G-protein β3 subunit gene;

(5) polymorphism at the base number position −482 of the apolipoprotein C-III gene; and (6) polymorphism at the base number position −6 of the angiotensinogen gene.

[2] A method for detecting the genotype in a nucleic acid sample, comprising the following step (b):

(b) analyzing two or more polymorphisms selected from the group consisting of the following (7) to (11) in a nucleic acid sample:

(7) polymorphism at the base number position 1186 of the thrombospondin 4 gene;

(8) polymorphism at the base number position −863 of the tumor necrosis factor-α gene;

(9) polymorphism at the base number position 2136 of the thrombomodulin gene;

(10) polymorphism at the base number position 5713 of the thrombopoietin gene; and

(11) polymorphism at the base number position 994 of the platelet-activating factor acetylhydrolase gene.

[3] A method for detecting the genotype in a nucleic acid sample, comprising the following step (c):

(c) analyzing two or more polymorphisms selected from the group consisting of the following (12) to (17) in a nucleic acid sample:

(12) polymorphism at the base number position 561 of the E-selectin gene;

(13) polymorphism at the base number position 2445 of the fatty acid-binding protein 2 gene;

(14) polymorphism at the base number position 1018 of the glycoprotein Ibα gene;

(15) polymorphism at the base number position −668 of the plasminogen activator inhibitor-1 gene;

(16) polymorphism at the base number position 584 of the paraoxonase gene; and

(17) polymorphism at the base number position 3932 of the apolipoprotein E gene.

[4] A method for detecting the genotype in a nucleic acid sample, comprising the following step (d):

(d) analyzing two or more polymorphisms selected from the group consisting of the following (18) to (22) in a nucleic acid sample:

(18) polymorphism at the base number position −668 of the plasminogen activator inhibitor-1 gene;

(19) polymorphism at the base number position −482 of the apolipoprotein C-III gene;

(20) polymorphism at the base number position 584 of the paraoxonase gene;

(21) polymorphism at the base number position 1018 of glycoprotein Ibα gene; and

(22) polymorphism at the base number position 3932 of the apolipoprotein E gene.

[5] A method for diagnosing the risk of restenosis after coronary angioplasty, comprising the following steps (i) to (iii):

(i) analyzing two or more polymorphisms selected from the group consisting of the following (1) to (6) in a nucleic acid sample:

(1) polymorphism at the base number position 3932 of the apolipoprotein E gene;

(2) polymorphism at the base number position 1648 of the glycoprotein Ia gene;

(3) polymorphism at the base number position −863 of the tumor necrosis factor-α gene;

(4) polymorphism at the base number position 825 of G-protein β3 subunit gene;

(5) polymorphism at the base number position −482 of the apolipoprotein C-III gene; and (6) polymorphism at the base number position −6 of the angiotensinogen gene;

(ii) determining, based on the information about polymorphism which was obtained in the step (i), the genotype of the nucleic acid sample; and (iii) assessing, based on the genotype determined, a genetic risk of restenosis after coronary angioplasty.

[6] A method for diagnosing the risk of restenosis after coronary angioplasty, comprising the following steps (iv) to (vi):

(iv) analyzing two or more polymorphisms selected from the group consisting of the following (7) to (11) in a nucleic acid sample:

(7) polymorphism at the base number position 1186 of the thrombospondin 4 gene;

(8) polymorphism at the base number position −863 of the tumor necrosis factor-α gene;

(9) polymorphism at the base number position 2136 of the thrombomodulin gene;

(10) polymorphism at the base number position 5713 of the thrombopoietin gene; and

(11) polymorphism at the base number position 994 of the platelet-activating factor acetylhydrolase gene;

(v) determining, based on the information about polymorphism which was obtained in the step (iv), the genotype of the nucleic acid sample; and (vi) assessing, based on the genotype determined, a genetic risk of restenosis after coronary angioplasty.

[7] A method for diagnosing the risk of restenosis after coronary angioplasty, comprising the following steps (vii) to (ix):

(vii) analyzing two or more polymorphisms selected from the group consisting of the following (12) to (17) in a nucleic acid sample:

(12) polymorphism at the base number position 561 of the E-selectin gene;

(13) polymorphism at the base number position 2445 of the fatty acid-binding protein 2 gene;

(14) polymorphism at the base number position 1018 of the glycoprotein Ibα gene;

(15) polymorphism at the base number position −668 of the plasminogen activator inhibitor-1 gene;

(16) polymorphism at the base number position 584 of the paraoxonase gene; and

(17) polymorphism at the base number position 3932 of the apolipoprotein E gene;

(viii) determining, based on the information about polymorphism which was obtained in the step (vii), the genotype of the nucleic acid sample; and (ix) assessing, based on the genotype determined, a genetic risk of restenosis after coronary angioplasty.

[8] A method for diagnosing the risk of restenosis after coronary angioplasty, comprising the following steps (x) to (xii):

(x) analyzing two or more polymorphisms selected from the group consisting of the following (18) to (22) in a nucleic acid sample:

(18) polymorphism at the base number position −668 of the plasminogen activator inhibitor-1 gene;

(19) polymorphism at the base number position −482 of the apolipoprotein C-III gene;

(20) polymorphism at the base number position 584 of the paraoxonase gene;

(21) polymorphism at the base number position 1018 of glycoprotein Ibα gene; and

(22) polymorphism at the base number position 3932 of the apolipoprotein E gene;

(xi) determining, based on the information about polymorphism which was obtained in the step (x), the genotype of the nucleic acid sample; and (xii) assessing, based on the genotype determined, a genetic risk of restenosis after coronary angioplasty.

[9] A kit for detecting the genotype, comprising two or more of nucleic acids selected from the group consisting of the following (1) to (6):

(1) a nucleic acid for analyzing polymorphism at the base number position 3932 of the apolipoprotein E gene;

(2) a nucleic acid for analyzing polymorphism at the base number position 1648 of the glycoprotein Ia gene;

(3) a nucleic acid for analyzing polymorphism at the base number position −863 of the tumor necrosis factor-α gene;

(4) a nucleic acid for analyzing polymorphism at the base number position 825 of G-protein β3 subunit gene;

(5) a nucleic acid for analyzing polymorphism at the base number position −482 of the apolipoprotein C-III gene; and (6) a nucleic acid for analyzing polymorphism at the base number position −6 of the angiotensinogen gene.

[10] A kit for detecting the genotype, comprising two or more of nucleic acids selected from the group consisting of the following (7) to (11):

(7) a nucleic acid for analyzing polymorphism at the base number position 1186 of the thrombospondin 4 gene;

(8) a nucleic acid for analyzing polymorphism at the base number position −863 of the tumor necrosis factor-a gene;

(9) a nucleic acid for analyzing polymorphism at the base number position 2136 of the thrombomodulin gene;

(10) a nucleic acid for analyzing polymorphism at the base number position 5713 of the thrombopoietin gene; and

(11) a nucleic acid for analyzing polymorphism at the base number position 994 of the platelet-activating factor acetylhydrolase gene.

[11] A kit for detecting the genotype, comprising two or more of nucleic acids selected from the group consisting of the following (12) to (17):

(12) a nucleic acid for analyzing polymorphism at the base number position 561 of the E-selectin gene;

(13) a nucleic acid for analyzing polymorphism at the base number position 2445 of the fatty acid-binding protein 2 gene;

(14) a nucleic acid for analyzing polymorphism at the base number position 1018 of glycoprotein Ibα gene;

(15) a nucleic acid for analyzing polymorphism at the base number position −668 of the plasminogen activator inhibitor-1 gene;

(16) a nucleic acid for analyzing polymorphism at the base number position 584 of the paraoxonase gene; and

(17) a nucleic acid for analyzing polymorphism at the base number position 3932 of the apolipoprotein E gene.

[12] A kit for detecting the genotype, comprising two or more of nucleic acids selected from the group consisting of the following (18) to (22):

(18) a nucleic acid for analyzing polymorphism at the base number position −668 of the plasminogen activator inhibitor-1 gene;

(19) a nucleic acid for analyzing polymorphism at the base number position −482 of the apolipoprotein C-III gene;

(20) a nucleic acid for analyzing polymorphism at the base number position 584 of the paraoxonase gene;

(21) a nucleic acid for analyzing polymorphism at the base number position 1018 of the glycoprotein Ibα gene; and

(22) a nucleic acid for analyzing polymorphism at the base number position 3932 of the apolipoprotein E gene.

[13] Fixed nucleic acids comprising the following two or more nucleic acid selected from the group consisting of the following (1) to (7) fixed to an insoluble support:

(1) a nucleic acid for analyzing polymorphism at the base number position 3932 of the apolipoprotein E gene;

(2) a nucleic acid for analyzing polymorphism at the base number position 1648 of the glycoprotein Ia gene;

(3) a nucleic acid for analyzing polymorphism at the base number position −863 of the tumor necrosis factor-α gene;

(4) a nucleic acid for analyzing polymorphism at the base number position 825 of G-protein β3 subunit gene;

(5) a nucleic acid for analyzing polymorphism at the base number position −482 of the apolipoprotein C-III gene; and (6) a nucleic acid for analyzing polymorphism at the base number position −6 of the angiotensinogen gene.

[14] Fixed nucleic acids comprising the following two or more nucleic acid selected from the group consisting of the following (7) to (11) fixed to an insoluble support:

(7) a nucleic acid for analyzing polymorphism at the base number position 1186 of the thrombospondin 4 gene;

(8) a nucleic acid for analyzing polymorphism at the base number position −863 of the tumor necrosis factor-α gene;

(9) a nucleic acid for analyzing polymorphism at the base number position 2136 of the thrombomodulin gene;

(10) a nucleic acid for analyzing polymorphism at the base number position 5713 of the thrombopoietin gene; and

(11) a nucleic acid for analyzing polymorphism at the base number position 994 of the platelet-activating factor acetylhydrolase gene.

[15] Fixed nucleic acids comprising the following two or more nucleic acid selected from the group consisting of the following (12) to (17) fixed to an insoluble support:

(12) a nucleic acid for analyzing polymorphism at the base number position 561 of the E-selectin gene;

(13) a nucleic acid for analyzing polymorphism at the base number position 2445 of the fatty acid-binding protein 2 gene;

(14) a nucleic acid for analyzing polymorphism at the base number position 1018 of glycoprotein Ibα gene;

(15) a nucleic acid for analyzing polymorphism at the base number position −668 of the plasminogen activator inhibitor-1 gene;

(16) a nucleic acid for analyzing polymorphism at the base number position 584 of the paraoxonase gene; and

(17) a nucleic acid for analyzing polymorphism at the base number position 3932 of the apolipoprotein E gene.

[16] Fixed nucleic acids comprising the following two or more nucleic acid selected from the group consisting of the following (18) to (22) fixed to an insoluble support:

(18) a nucleic acid for analyzing polymorphism at the base number position −668 of the plasminogen activator inhibitor-1 gene;

(19) a nucleic acid for analyzing polymorphism at the base number position −482 of the apolipoprotein C-III gene;

(20) a nucleic acid for analyzing polymorphism at the base number position 584 of the paraoxonase gene;

(21) a nucleic acid for analyzing polymorphism at the base number position 1018 of the glycoprotein Ibα gene; and

(22) a nucleic acid for analyzing polymorphism at the base number position 3932 of the apolipoprotein E gene.

BRIEF DESCRIPTION OF THE DRAWINGS

FIG. 1 is a table summarizing 112 gene polymorphisms examined in a screening association study in Examples.

FIG. 2 is also a table summarizing 112 gene polymorphisms examined in a screening association study in Examples.

FIG. 3 is a table summarizing primers (SEQ ID NOs: 31, 32, 33, 28, 29, 30, 16, 17, 18, 46, 47, 48, 49, 50, 51, 25, 26, 27, 19, 20, 21, 52, 53, 54, 57, 58, 59, 55 and 56 in this order from the top), probes (SEQ ID NOs: 60, 61, 62, 63, 64, 65, 66 and 67 in this order from the top) and other conditions used to determine the genotype in Examples. In FIG. 3, FITC denotes fluorescein isothiocyanate, TxR denotes Texas Red and Biotin denotes biotin, respectively.

FIG. 4 is also a table summarizing primers (SEQ ID NOs: 43, 44, 45, 37, 38, 39, 40, 41, 42, 34, 35, 36, 22, 23 and 24 in this order from the top) and other conditions used to determine the genotype in Examples. In FIG. 4, FITC denotes fluorescein isothiocyanate and TxR denotes Texas Red and Biotin denotes biotin, respectively.

FIG. 5 is a table summarizing single nucleotide polymorphisms examined in an association study in Examples.

FIG. 6 is a table summarizing the background data of 1620 lesions in men examined in an association study in Examples. Each data is represented by average±standard deviation or percentage (%). In table, *1 denotes P<0.0001 (versus corresponding "No restenosis"), *2 denotes P<0.001 (versus corresponding "No restenosis"), *3 denotes P<0.05 (versus corresponding "No restenosis") and *4 denotes P<0.005 (versus corresponding "No restenosis"), respectively.

FIG. 7 is a table summarizing the background data of 771 lesions in women examined in an association study in Examples. Each data is represented by average±standard deviation or percentage (%). In table, *1 denotes P<0.005 (versus corresponding "No restenosis"), *2 denotes P<0.05 (versus corresponding "No restenosis"), *3 denotes P<0.0001 (versus corresponding "No restenosis") and *4 denotes P<0.001 (versus corresponding "No restenosis"), respectively.

FIG. 8 is a table summarizing gene polymorphisms and results of multivariate logistic regression analysis examined in the association study (in men).

FIG. 9 is a table summarizing gene polymorphisms and results of multivariate logistic regression analysis examined in the association study (in women).

FIG. 10 is a table showing results of step forward selection method of multivariate logistic regression analysis of gene polymorphisms associated with restenosis after coronary angioplasty (in men).

FIG. 11 is a table showing results of step forward selection method of multivariate logistic regression analysis of gene polymorphisms associated with restenosis after coronary angioplasty (in women).

FIG. 12 is a table showing results of diagnosis of genetic risk of restenosis after balloon dilatation using a combination of five gene polymorphisms in men.

FIG. 13 is a table showing results of diagnosis of genetic risk of restenosis after stent implantation using a combination of five gene polymorphisms in men.

FIG. 14 is a table showing results of diagnosis of genetic risk of restenosis after balloon dilatation using a combination of five gene polymorphisms in women.

FIG. 15 is a table showing results of diagnosis of genetic risk of restenosis after stent implantation using a combination of five gene polymorphisms in women.

BEST MODE FOR CARRYING OUT THE INVENTION

Figure 16:
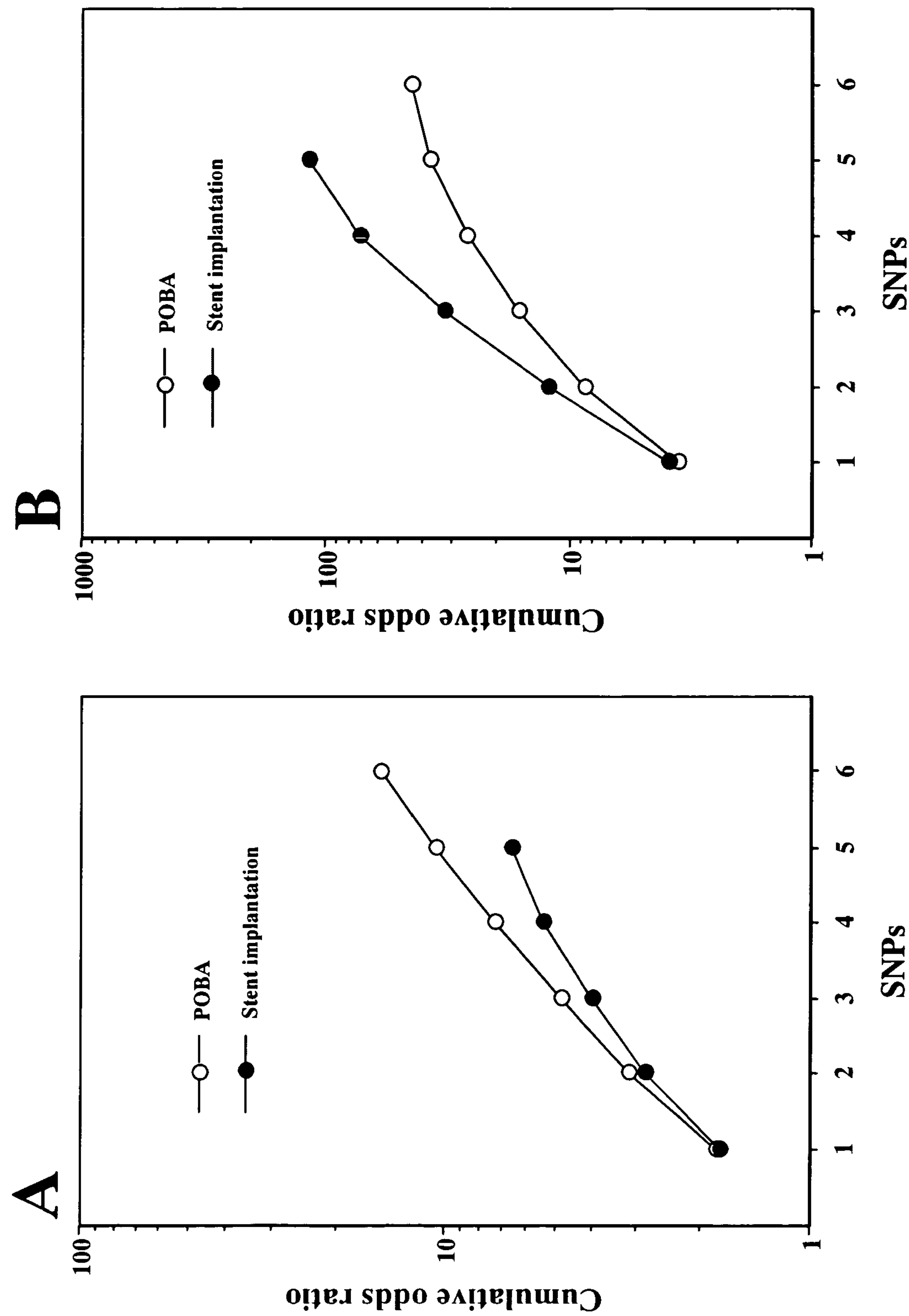
FIG. 16 is a graph showing a correlation between the cumulative odds ratio for restenosis after coronary angioplasty and the number of single nucleotide polymorphisms. (○) shows the correlation in restenosis after balloon dilatation and (●) shows the correlation in restenosis after stent implantation, and (A) shows the correlation in men and (B) shows the correlation in women. In (A), SNPs of restenosis after balloon dilatation include: SNP 1: ApoE (3932T→C) polymorphism; SNP 2: GPIa (1648A→G) polymorphism; SNP 3: TNFα (−863C→A) polymorphism; SNP 4: G-protein β3 (825C→T) polymorphism; SNP5: ApoC-III (−482C→T) polymorphism; and SNP6: AGT (−6G→A) polymorphism. Similarly, in (A) SNPs of restenosis after stent implantation include: SNP1: TSP4 (1186G→C) polymorphism, SNP2: TNFα (−863C→A) polymorphism; SNP3: TM (2136C→T) polymorphism; SNP4: TPO (5713A→G) polymorphism; and SNP5: PAF-AH (994G→T). In (B) SNPs of restenosis after balloon dilatation include: SNP 1: E-selectin gene (561A→C) polymorphism; SNP2: FABP2 (2445G→A) polymorphism; SNP3: GPIbα (1018C→T) polymorphism; SNP4: PAI1 (−668/4G→5G) polymorphism; SNP5: PON (584G→A) polymorphism; and SNP6: ApoE (3932T→CPAI1) polymorphism. Similarly, in (B) SNPs of restenosis after stent implantation include: SNP1: PAI1 (−668/4G →5G) polymorphism; SNP2: ApoC-III (−482C→T) polymorphism; SNP3: PON (584G→A) polymorphism; SNP4: GPIbα (1018C→T) polymorphism; and SNP5: ApoE (3932T→C) polymorphism.

The first aspect of the present invention relates to a method of detecting the genotype in a nucleic acid sample. One embodiment of the present invention is featured by including the step of analyzing two or more polymorphisms selected from the group consisting of the following (1) to (6). Another embodiment is featured by including the step of analyzing two or more polymorphisms selected from the group consisting of the following (7) to (11). Further embodiment is featured by including the step of analyzing two or more polymorphisms selected from the group consisting of the following (12) to (17). Yet further embodiment is featured by including the step of analyzing two or more polymorphisms selected from the group consisting of the following (18) to (22). Note here that it is possible to determine, based on the information about polymorphism which was obtained in the above-mentioned step, the genotype of the nucleic acid sample, and thereby to assess, based on the genotype determined, a genetic risk of restenosis after coronary angioplasty.

(1) polymorphism at the base number position 3932 of the apolipoprotein E gene: 3932T→C (hereinafter, also referred to as "ApoE (3932T→C) polymorphism")

(2) polymorphism at the base number position 1648 of the glycoprotein Ia gene: 1648A→G (hereinafter, also referred to as "GPIa (1648A→G) polymorphism")

(3) polymorphism at the base number position −863 of the tumor necrosis factor-α gene: −863C→A (hereinafter, also referred to as "TNFα (−863C→A) polymorphism")

(4) polymorphism at the base number position 825 of the G-protein β3 subunit gene: 825C→T (hereinafter, also referred to as "G-protein β3 (825C→T) polymorphism")

(5) polymorphism at the base number position −482 of the apolipoprotein C-III gene: −482C→T (hereinafter, also referred to as "ApoC-III (−482C→T) polymorphism")

(6) polymorphism at the base number position −6 of the angiotensinogen gene: −6G→A (hereinafter, also referred to as "AGT (−6G→A) polymorphism")

(7) polymorphism at the base number position 1186 of the thrombospondin 4 gene: 1186G→C (hereinafter, also referred to as "TSP4 (1186G→C) polymorphism")

(8) polymorphism at the base number position −863 of the tumor necrosis factor-α gene: −863C→A (hereinafter, also referred to as "TNFα (−863C→A) polymorphism")

(9) polymorphism at the base number position 2136 of the thrombomodulin gene: 2136C→T (hereinafter, also referred to as "TM (2136C→T) polymorphism")

(10) polymorphism at the base number position 5713 of the thrombopoietin gene: 5713A→G (hereinafter, also referred to as "TPO (5713A→G) polymorphism")

(11) polymorphism at the base number position 994 of the platelet-activating factor acetylhydrolase gene: 994G→T (hereinafter, also referred to as "PAF-AH (994G→T) polymorphism")

(12) polymorphism at the base number position 561 of the E-selectin gene: 561A→C (hereinafter, also referred to as "E-selectin (561A→C) polymorphism")

(13) polymorphism at the base number position 2445 of the fatty acid-binding protein 2 gene: 2445G→A (hereinafter, also referred to as "FABP2 (2445G→A)polymorphism")

(14) polymorphism at the base number position 1018 of the glycoprotein Ibα gene: 1018 C→T (hereinafter, also referred to as "GPIbα (1018C→T) polymorphism")

(15) polymorphism at the base number position −668 of the plasminogen activator inhibitor-1 gene: −668/4G→5G (hereinafter, also referred to as "PAI1 (−668/4G→5G) polymorphism")

(16) polymorphism at the base number position 584 of the paraoxonase gene: 584G→A (hereinafter, also referred to as "PON (584G→A) polymorphism")

(17) polymorphism at the base number position 3932 of the apolipoprotein E gene: 3932T→C (hereinafter, also referred to as "ApoE (3932T→C) polymorphism")

(18) polymorphism at the base number position −668 of the plasminogen activator inhibitor-1 gene: −668/4G→5G (hereinafter, also referred to as "PAI1 (−668/4G→5G) polymorphism")

(19) polymorphism at the base number position −482 of the apolipoprotein C-III gene: −482C→T (hereinafter, also referred to as "ApoC-III (−482C→T) polymorphism")

(20) polymorphism at the base number position 584 of the paraoxonase gene: 584G→A (hereinafter, also referred to as "PON (584G→A) polymorphism")

(21) polymorphism at the base number position 1018 of the glycoprotein Ibα gene: 1018C→T (hereinafter, also referred to as "GPIbα (1018C→T) polymorphism")

(22) polymorphism at the base number position 3932 of the apolipoprotein E gene: 3932T→C (hereinafter, also referred to as "ApoE (3932T→C) polymorphism")

In the above, description such as 3932T→C means that polymorphism at the relevant base number position consists of two genotypes, bases before and after the arrow. Herein, −668/4G→5G means a polymorphism consisting of a genotype having four G (guanines) existing successively in the 3' direction from the base number position −668 and a genotype having five G existing successively in the 3' direction from the base number position −668.

The base number of each gene is expressed using as standards the known sequences which are registered in the public database, GenBank (NCBI). Note here that in the base sequence of SEQ ID NO: 1 (Accession No. M10065 J03053 J03054: Human apolipoprotein E (epsilon-4 allele) gene, complete cds), the 3932nd base corresponds to the base at position 3932 of the apolipoprotein E gene. Similarly, in the base sequence of SEQ ID NO: 2 (Accession No. X17033 M28249: Human mRNA for integrin alpha-2 subunit), the 1648th base corresponds to the base at position 1648 of the glycoprotein Iα gene; in the base sequence of SEQ ID NO: 3 (Accession No. L11698: Homo sapiens tumor necrosis factor alpha gene, promoter region), the 197th base corresponds to the base at position −863 of the tumor necrosis factor-α gene; in the base sequence of SEQ ID NO: 4 (Accession No. M31328: Human guanine nucleotide-binding protein beta-3 subunit mRNA, complete cds), the 831st base corresponds to the base at position 825 of the G-protein β3 subunit gene; in the base sequence of SEQ ID NO: 5 (Accession No. X13367: Human DNA for apolipoprotein C-III 5'-flank), the 936th base corresponds to the base at position −482 of the apolipoprotein C-III gene; in the sequence of SEQ ID NO: 6 (Accession No. X15323: *H.sapiens* angiotensinogen gene 5' region and exon 1), the 463rd base corresponds to the base at position −6 of the angiotensinogen gene; in the sequence of SEQ ID NO: 7 (Accession No. Z19585: *H.sapiens* mRNA for thrombospondin-4), the 1186th base corresponds to the base at position 1186 of the thrombospondin 4 gene; in the sequence of SEQ ID NO: 8 (Accession No. D00210: *Homo sapiens* gene for thrombomodulin precursor, complete cds), the 2136th base corresponds to the base at position 2136 of the thrombomodulin gene; in the sequence of SEQ ID NO: 9 (Accession No. L36051: Human thrombopoietin gene, complete cds), the 5753rd base corresponds to the base at position 5713; in the sequence of SEQ ID NO: 10 (Accession No. U20157: Human platelet-activating factor acetylhydrolase mRNA, complete cds), the 996th base corresponds to the base at position 994 of the platelet-activating factor acetylhydrolase gene; in the sequence of SEQ ID NO: 11 (Accession No. M24736: Human endothelial leukocyte adhesion molecule 1 (ELAM-1) mRNA, complete cds), the 561st base corresponds to the base at position 561 of the E-selectin gene; in the sequence of SEQ ID NO: 12 (Accession No. M18079 J03465: Human, intestinal fatty acid binding protein gene, complete cds, and an Alu repetitive element.), the 2445th base corresponds to the base at position 2445 of the fatty acid-binding protein 2 gene; in the sequence of SEQ ID NO: 13 (Accession No. J02940: Human platelet glycoprotein Ib alpha chain mRNA, complete cds), the 524th base corresponds to the base at position 1018 of the glycoprotein Ibα gene; in the sequence of SEQ ID NO: 14 (Accession No. X13323: Human gene for plasminogen activator inhibitor 1 (PAI-1) 5'-flank and exon 1), the 131st base corresponds to the base at position −668 of the plasminogen activator inhibitor-1 gene; and in the sequence of SEQ ID NO: 15 (Accession No. M63012: *H.sapiens* serum paraoxonase (PON) mRNA, complete cds), the 584th base corresponds to the base at position 584 of the paraoxonase gene.

In the present invention, "analyzing polymorphism" means the investigation as to what genotype a nucleic acid sample has in the gene polymorphism to be analyzed. It is the same meaning as the investigation on the base (base sequence) of the position in which the polymorphism exists. Typically, for example, in the case of the analysis of the ApoE (3932T→C) polymorphism, it refers to investigation on what genotype, i.e., CC (the base at position 3932 is a homozygote of allele C), TC (the base at position 3932 is a heterozygote of allele T and allele C) and TT (the base at position 3932 is a homozygote of allele T), the apolipoprotein E gene in a nucleic acid sample has.

As shown in Examples mentioned below, the polymorphisms mentioned (1) to (6) above are polymorphisms that are recognized as being particularly effective to be used in determining genetic risk of restenosis after coronary angioplasty in an analysis of Japanese male subjects who underwent balloon dilatation. Therefore, analysis targeting these polymorphisms enables diagnosis with higher accuracy and with higher predictability when balloon dilatation is performed as a coronary angioplasty and subjects are men (particularly, Japanese men).

Similarly, as shown in Examples mentioned below, the polymorphisms mentioned (7) to (11) above are polymorphisms that are recognized as being particularly effective to be used in determining genetic risk of restenosis after coronary angioplasty in an analysis of Japanese male subjects who underwent stent implantation. Therefore, analysis targeting these polymorphisms enables diagnosis with higher accuracy and with higher predictability when stent implantation is performed as a coronary angioplasty and subjects are men (particularly, Japanese men).

Similarly, as shown in Examples mentioned below, the polymorphisms mentioned (12) to (17) above are polymorphisms that are recognized as being particularly effective to be used in determining genetic risk of restenosis after coronary angioplasty in an analysis of Japanese female subjects who underwent balloon dilatation. Therefore, analysis targeting these polymorphisms enables diagnosis with higher accuracy and with higher predictability when balloon dilatation is performed as a coronary angioplasty and subjects are women (particularly, Japanese women).

Similarly, as shown in Examples mentioned below, the polymorphisms mentioned (18) to (22) above are polymorphisms that are recognized as being particularly effective to be used in determining genetic risk of restenosis after coronary angioplasty in an analysis of Japanese female subjects who underwent stent implantation. Therefore, analysis targeting these polymorphisms enables diagnosis with higher accuracy and with higher predictability when stent implantation is performed as a coronary angioplasty and subjects are women (particularly, Japanese women).

Herein, in principle, in proportion to the increase in the number of polymorphisms to be analyzed, the genotypes of nucleic acid sample are classified more finely. Thereby, it is possible to diagnose a genetic risk of restenosis after coronary angioplasty with higher predictability. From this viewpoint, it is preferable to detect the genotype by analyzing a larger number of polymorphisms in the above-mentioned polymorphisms (1) to (6). Therefore, it is the most preferable to analyze all of the polymorphisms (1) to (6). In the case where detection is carried out by combining five or less of polymorphisms, it is preferable to preferentially select the polymorphisms with higher odds ratios as in Examples mentioned below. For example, in the case where five polymorphisms are used in combination, it is preferable to select five polymorphisms with higher odds ratio, that is, to select (1), (2), (3), (4) and (5). Similarly, in the case where four polymorphisms are used in combination, it is preferable to select (1), (3), (4) and (5). Similarly, in the case where three polymorphisms are used in combination, it is preferable to select (1), (3) and (4).

Similarly, in the case where two or more polymorphisms selected from the group consisting of polymorphisms (7) to (11), it is most preferable to analyze all these polymorphisms, that is, five polymorphisms. In the case where detection is carried out by combining four or less of polymorphisms, it is preferable to preferentially select the polymorphisms with higher odds ratios in Examples mentioned below. For example, in the case where four polymorphisms are used in combination, it is preferable to select four polymorphisms with higher odds ratio, that is, to select (7), (8), (9) and (10). Similarly, in the case where three polymorphisms are used in combination, it is preferable to select (7), (8) and (9). Similarly, in the case where two polymorphisms are used in combination, it is preferable to select (7) and (8).

Similarly, in the case where two or more polymorphisms selected from the group consisting of polymorphisms (12) to (17), it is most preferable to analyze all these polymorphisms, that is, six polymorphisms. In the case where detection of the genotype is carried out by combining five or less of polymorphisms, it is preferable to preferentially select the polymorphisms with higher odds ratios in Examples mentioned below. For example, in the case where five polymorphisms are used in combination, it is preferable to select five polymorphisms with higher odds ratio, that is, to select (12), (13), (14), (15) and (16). Similarly, in the case where four polymorphisms are used in combination, it is preferable to select (12), (13) (14) and (15). Similarly, in the case where three polymorphisms are used in combination, it is preferable to select (12), (13) and (14).

Similarly, in the case where two or more polymorphisms selected from the group consisting of polymorphisms (18) to (22), it is most preferable to analyze all these polymorphisms, that is, five polymorphisms. In the case where detection of the genotype is carried out by combining four or less of polymorphisms, it is preferable to preferentially select the polymorphisms with higher odds ratios in Examples mentioned below. For example, in the case where four polymorphisms are used in combination, it is preferable to select four polymorphisms with higher odds ratio, that is, to select (18), (19), (20) and (21). Similarly, in the case where three polymorphisms are used in combination, it is preferable to select (18), (19) and (20). Similarly, in the case where two polymorphisms are used in combination, it is preferable to select (18) and (19).

A method for analyzing each genetic polymorphism is not particularly limited. Known methods may include, for example, amplification by PCR using an allele-specific primer (and probe), a method for analyzing polymorphism of amplified product by means of fluorescence or luminescence, PCR-RFLP (polymerase chain reaction-restriction fragment length polymorphism) method, PCR-SSCP (polymerase chain reaction-single strand conformation polymorphism) method (Orita, M. et al., Proc. Natl. Acad. Sci., U.S.A., 86, 2766-2770 (1989), etc.), PCR-SSO (specific sequence oligonucleotide) method, which use PCR method, ASO (allele specific oligonucleotide) hybridization method combining the PCR-SSO method and a dot hybridization method (Saiki, Nature, 324, 163-166 (1986), etc.), or TaqMan-PCR method (Livak, K J, Genet Anal, 14, 143 (1999), Morris, T. et al., J. Clin. Microbiol.,34, 2933 (1996)), Invader method (Lyamichev V et al., Nat Biotechnol, 17, 292 (1999)), MALDI-TOF/MS (matrix) method using a primer extension method (Haff L A, Smirnov I P, Genome Res 7, 378 (1997)), RCA (rolling cycle amplification) method (Lizardi P M et al., Nat Genet 19,225 (1998)), a method using DNA microchip or micro-array (Wang D G et al., Science 280, 1077 (1998), etc.)), a primer extension method, a Southern blot hybridization method, a dot hybridization method (Southern, E., J. Mol. Biol. 98, 503-517 (1975)), etc.), or the like. Furthermore, an analysis may be made by direct sequencing of the portion of polymorphism which is subject to analysis. Note here that polymorphisms may be analyzed by combining these methods ad libitum.

In the case where the amount of nucleic acid sample is small, it is preferable to analyze it by a method using PCR (for example, PCR-RFLP method) from the viewpoint of detection sensitivity or accuracy. Furthermore, any of the above-mentioned analysis methods may be employed after nucleic acid sample is amplified in advance (including a partial region of nucleic acid sample) by a gene amplification such as PCR method or a method applying PCR method.

Meanwhile, in the case where a large number of nucleic acid samples are analyzed, a method capable of analyzing a large number of samples in a relatively short period of time, for example, allele-specific PCR method, allele-specific hybridization method, TaqMan-PCR method, Invader method, MALDI-TOF/MS (matrix) method using a primary extension method, RCA (rolling cycle amplification) method, or a method using a DNA chip or a micro-array.

The above methods use nucleic acids (also called "nucleic acids for analyzing polymorphism" in the present invention), e.g., primer and probe, in accordance with each method. An example of the nucleic acids for analyzing polymorphism may include a nucleic acid having a sequence complementary to a given region including the site of polymorphism (partial DNA region) in a gene which contains polymorphism to be analyzed, and a nucleic acid (primer) which has a sequence complementary to a given region including the site of polymorphism (partial DNA region) in a gene which contains polymorphism to be analyzed and which is designed to specifically amplify the DNA fragment containing the relevant site of polymorphism. In the case where polymorphism at position 3932 of the apolipoprotein E gene is a subject to be analyzed, an example of such nucleic acids includes a nucleic acid having a sequence complementary to a partial DNA region including the position 3932 of the apolipoprotein E gene whose base at position 3932 is T (thymine), or a nucleic acid having a sequence complementary to a partial DNA region including the position 3932 of the apolipoprotein E gene whose base at position 3932 is C (cytosine).

Other concrete examples of nucleic acids for analyzing polymorphism may include a set of nucleic acids which is designed to specifically amplify the partial DNA region that contains the relevant site of polymorphism only in the case where the site of polymorphism to be analyzed is a certain genotype. A more concrete example may include a set of nucleic acids which is designed to specifically amplify the partial DNA region including the site of polymorphism to be analyzed and which consists of a sense primer that specifically hybridizes the partial DNA region including the relevant site of polymorphism in an antisense strand whose site of polymorphism is a certain genotype and of an antisense primer that specifically hybridizes a partial region in the sense strand. In the case where polymorphism at position 3932 of the apolipoprotein E gene is a subject to the analysis, examples of such a set of nucleic acids include a set of nucleic acids which is designed to specifically amplify the partial DNA region including the base at position 3932 of the apolipoprotein E gene and which consists of a sense primer that specifically hybridizes the partial DNA region containing the base at position 3932 in the antisense strand of the apolipoprotein E gene whose base at 3932 is T (thymine) and of an antisense primer that specifically hybridizes a partial region in the sense strand; or a set of nucleic acids which consists of a sense primer that specifically hybridizes the partial DNA region including the base at position 3932 in the antisense strand of the apolipoprotein E gene whose base at position 3932 is C (cytosine) and of an antisense primer that specifically hybridizes a partial region in the sense strand. The length of the partial DNA region to be amplified here is set accordingly in a range which is appropriate for its detection, and is for example, 50 bp to 200 bp, and preferably 80 bp to 150 bp. A more concrete example may include a set of nucleic acids for analyzing the ApoE (3932T→C) polymorphism containing the following sequences. Note here that an underlined part in the following sequences means a part corresponding to the polymorphism. Furthermore, in the sequence, N denotes any of A, T, C and G.

```
antisense primer
GGACATGGAGGACGTNCG:,          SEQ ID NO: 16
or
CGGACATGGAGGACGTNTG:          SEQ ID NO: 17

sense primer
CGCGGTACTGCACCAGGC:           SEQ ID NO: 18
```

Similarly, an example of a nucleic acid primer for analyzing the GPIa (1648A→G) polymorphism may include a set containing the following sequences.

```
sense primer
GAGTCTACCTGTTTACTATCAANAA:,     SEQ ID NO: 19
or
GAGTCTACCTGTTTACTATCAANGA:      SEQ ID NO: 20

antisense primer
ACCAGTACTAAAGCAAATTAAACT:       SEQ ID NO: 21
```

Similarly, an example of a nucleic acid primer for analyzing the TNFα (−863C→A) polymorphism may include a set containing the following sequences.

```
antisense primer
GGCCCTGTCTTCGTTAANGG:,          SEQ ID NO: 22
or
ATGGCCCTGTCTTCGTTAANTG:         SEQ ID NO: 23

sense primer
CCAGGGCTATGGAAGTCGAGTATC:       SEQ ID NO: 24
```

Similarly, an example of a nucleic acid primer for analyzing the G-protein β3 (825C→T) polymorphism may include a set containing the following sequences.

```
sense primer
TCTGCGGCATCACGTNCG:,          SEQ ID NO: 25
or
TCTGCGGCATCACGTNTG:           SEQ ID NO: 26

antisense primer
GAATAGTAGGCGGCCACTGA:         SEQ ID NO: 27
```

Similarly, an example of a nucleic acid primer for analyzing the ApoC-III (−482C→T) polymorphism may include a set containing the following sequences.

sense primer
CGGAGCCACTGATGCNCG:, SEQ ID NO: 28
or
CGGAGCCACTGATGCNTG: SEQ ID NO: 29 antisense primer
TGTTTGGAGTAAAGGCACAGAA: SEQ ID NO: 30

Similarly, an example of a nucleic acid primer for analyzing the AGT (−6G→A) polymorphism may include a set containing the following sequences.

antisense primer
CGGCAGCTTCTTCCCNCG:, SEQ ID NO: 31
or
CGGCAGCTTCTTCCCNTG: SEQ ID NO: 32 sense primer
CCACCCCTCAGCTATAAATAGG: SEQ ID NO: 33

Similarly, an example of a nucleic acid primer for analyzing the TSP4 (1186G→C) polymorphism may include a set containing the following sequences.

sense primer
CGAGTTGGGAACGCACNCT:, SEQ ID NO: 34
or
CGAGTTGGGAACGCACNGT: SEQ ID NO: 35 antisense primer
GGTCTGCACTGACATTGATGAG: SEQ ID NO: 36

Similarly, an example of a nucleic acid primer for analyzing the TM (2136C→T) polymorphism may include a set containing the following sequences.

sense primer
CCCGACTCGGCCCTTNCC:, SEQ ID NO: 37
or
CCCGACTCGGCCCTTNTC: SEQ ID NO: 38 antisense primer
GTCACAGTCGGTGCCAATGT: SEQ ID NO: 39

Similarly, an example of a nucleic acid primer for analyzing the TPO (5713A→G) polymorphism may include a set containing the following sequences.

sense primer
CCGACATCAGCATTGTCTNAT:, SEQ ID NO: 40
or
CCGACATCAGCATTGTCTNGT: SEQ ID NO: 41 antisense primer
CTGCAGGGAAGGGAGCTGT: SEQ ID NO: 42

Similarly, an example of a nucleic acid primer for analyzing the PAF-AH (994G→T) polymorphism may include a set containing the following sequences.

sense primer
TTCTTTTGGTGGAGCAACNGT:, SEQ ID NO: 43
or
ATTCTTTTGGTGGAGCAACNTT: SEQ ID NO: 44 antisense primer
TCTTACCTGAATCTCTGATCTTCA: SEQ ID NO: 45

Similarly, an example of a nucleic acid primer for analyzing the E-selectin (561A→C) polymorphism may include a set containing the following sequences.

antisense primer
ACATTCACCGTGGCCANTG:, SEQ ID NO: 46
or
CATTCACCGTGGCCANGG: SEQ ID NO: 47 sense primer
AGCTGCCTGTACCAATACATCC: SEQ ID NO: 48

Similarly, an example of a nucleic acid primer for analyzing the FABP2 (2445G→A) polymorphism may include a set containing the following sequences.

sense primer
TCACAGTCAAAGAATCAAGNGC:, SEQ ID NO: 49
or
ATTCACAGTCAAAGAATCAAGNAC: SEQ ID NO: 50 antisense primer
CAAAAACAACTTCAATGTTTCGA: SEQ ID NO: 51

Similarly, an example of a nucleic acid primer for analyzing the GPIbα (1018C→T) polymorphism may include a set containing the following sequences.

sense primer
CCCAGGGCTCCTGNCG:, SEQ ID NO: 52
or
CCCCAGGGCTCCTGNTG: SEQ ID NO: 53 antisense primer
TGAGCTTCTCCAGCTTGGGTG: SEQ ID NO: 54

Similarly, an example of a nucleic acid primer for analyzing the PAI1 (−668/4G→5G) polymorphism may include a set containing the following sequences.

sense primer
GGCACAGAGAGAGTCTGGACACG: SEQ ID NO: 55 antisense primer
GGCCGCCTCCGATGATACA: SEQ ID NO: 56

Similarly, an example of a nucleic acid primer for analyzing the PON (584G→A) polymorphism may include a set containing the following sequences.

sense primer
ACCCAAATACATCTCCCAGGANCG:, SEQ ID NO: 57
or
AACCCAAATACATCTCCCAGGNCT: SEQ ID NO: 58 antisense primer
GAATGATATTGTTGCTGTGGGAC: SEQ ID NO: 59

On the other hand, a concrete example of the probe can include: as a probe for analyzing Apo C-III (−482C→T) polymorphism, AGCCACTGATGCNCGGTCT:, SEQ ID NO: 60
or
AGCCACTGATGCNTGGTCT:, SEQ ID NO: 61 as a probe for analyzing E-selectin (561A→C) polymorphism,

CACCGTGGCCANTGCAGGAT:, SEQ ID NO: 62
or
CACCGTGGCCANGGCAGGAT:, SEQ ID NO: 63 as a probe for analyzing FABP2 (2445G→A) polymorphism,

GAATCAAGNGCTTTTCGAAACATT:, SEQ ID NO: 64
or
GAATCAAGNACTTTTCGAAACATT:, SEQ ID NO: 65 as a probe for analyzing PAIL (−668/4G→5G) polymorphism,

TGGACACGTGGGGGAGTCAG:, SEQ ID NO: 66
or
TGGACACGTGGGGAGTCAGC:. SEQ ID NO: 67

The above nucleic acid primers and nucleic acid probes are mere examples. Nucleic acid primers may contain a partially modified base sequence as long as they can carry out the aimed amplification reaction without inconvenience, while nucleic acid probes may contain a partially modified base sequence as long as they can carry out the aimed hybridization reaction without inconvenience. “Partially modified” herein means that a part of bases is deleted, replaced, inserted, and/or added. The numbers of modified bases are for example one to seven, preferably one to five, and more preferably one to three. Note here that such a modification is made in the portions other than bases which correspond to the site of polymorphism, in principle. However, in the case where the polymorphism to be analyzed is PAI1 (−668/4G→5G) polymorphism, it is also possible to use a primer or probe obtained by modifying a part of the base corresponding to the polymorphism site.

As nucleic acids for analyzing polymorphism (probes or primers), DNA fragments or RNA fragments are used accordingly in response to the analysis method employed. The base length of nucleic acids for analyzing polymorphism may be sufficient if it exerts respective functions of each nucleic acid. Base lengths in the case of use as primers are for example, 10 to 50 bp, preferably 15 to 40 bp, and more preferably 15 to 30 bp.

Note here that in the case of use as primers, some mismatches to the sequence which constitutes the template may be admitted as long as the primer can specifically hybridize the subject for amplification and amplify the target DNA fragment. In the case of probes, some mismatches to the sequence which is subject to detection may be similarly admitted as long as the probe can specifically hybridize the sequence which is subject to detection. The numbers of mismatches are one to several, preferably one to five, and more preferably one to three.

Nucleic acids for analyzing polymorphism (primers and probes) can be synthesized in accordance with known methods, e.g., phosphodiester method. Note here that textbooks (e.g., Molecular Cloning, Third Edition, Cold Spring Harbor Laboratory Press, N.Y.) can be referred with respect to the design, synthesis, and others of nucleic acids for analyzing polymorphism.

Nucleic acids for analyzing polymorphism in the present invention can be labeled with labeling substances in advance. The use of such labeled nucleic acids allows, for example, the analysis of polymorphism by using the labeling amount in the product of amplification as a marker. Furthermore, by labeling two kinds of primers which were designed specifically amplify the partial DNA region in the gene of each genotype that constitute polymorphism with labeling substances that are different from each other, the genotype of a nucleic acid sample can be discriminated according to the labeling substance and labeling amount to be detected based on the product of amplification. Concrete examples of detection methods using these labeled primers may include: a method for detecting polymorphism, comprising labeling, with fluorescein isocyanate and Texas red, two kinds of nucleic acid primers (allele-specific sense primers) that respectively and specifically hybridize the sense strand of each genotype constituting polymorphism; amplifying the partial DNA region including the site of polymorphism by using these labeled primers and the antisense primers that specifically hybridize the antisense strand; and measuring the labeling amount of each fluorescent substance in the product of amplification obtained. Note here that labeling of the antisense primer herein with for example, biotin allows the separation of the product of amplification by utilizing the specific binding between biotin and avidin.

Radioactive isotopes, for example, $^{32}$P, and fluorescent substance, for example, fluorescein isothiocyanate, tetramethylrhodamine isothiocyanate, and Texas red, etc. can be exemplified as labeling substances to be used in labeling nucleic acids for analyzing polymorphism. The 5' terminal labeling method using alkaline phosphatase and T4 polynucleotide kinase, the 3' terminal labeling method using T4 DNA polymerase and Klenow fragment, nicktranslation method, random primer method (Molecular Cloning, Third Edition, Chapter 9, Cold Spring Harbor Laboratory Press, N.Y.), and the like can be exemplified as labeling methods.

The above-mentioned nucleic acids for analyzing polymorphism can be used also under a condition fixed to an insoluble support. Processing of an insoluble support to be used for the fixation to several forms such as chips and beads allows the more simplified analysis of polymorphism by using these fixed nucleic acids.

A nucleic acid sample can be prepared from blood, skin cells, mucous cells, hair, and others from the subject according to known extraction methods and purification methods. In the case of including the gene which is subject to the analysis of polymorphism, the genome DNA of arbitrary length can be used as a nucleic acid sample. Furthermore, it is not necessary to use a nucleic acid sample in which all genes subject to the analysis are present on one nucleic acid. That is to say, as a nucleic acid sample of the present invention, both material in which all genes subject to the analysis are present on one nucleic acid and material in which genes subject to the analysis are present separately on two or more nucleic acids can be used. Note here that material in a fragmented or partial condition may be accepted as long as the site of polymorphism to be analyzed is at least present, although genes subject to the analysis in a nucleic acid sample are not in a complete condition (i.e., a condition in which the full length of the gene is present).

Analysis of each gene polymorphism is carried out each by each of the gene polymorphism or a plurality or entire gene polymorphisms are carried out simultaneously. In the former case, for example, nucleic acid sample collected from the subjects is divided in accordance with the number of polymorphisms to be analyzed, and analysis of polymorphism is carried out individually. In the latter case, for example, analysis of polymorphism can be carried out by DNA chip or micro-array. Note here that “simultaneousness” herein not only imply that all operations of the analysis process are conducted simultaneously but also include the case in which part of operations (e.g., operation to amplify nucleic acid, hybridization or detection of the probe) is conducted simultaneously.

Polymorphism of each gene can be analyzed by using mRNA which is a product of transcription of the gene which is subject to the analysis. After extracting and purifying mRNA of the gene which is subject to the analysis from blood, urine, and others of the subject, for example, polymorphism can be analyzed with mRNA as a starting material by conducting methods, e.g., Northern blotting method (Molecular Cloning, Third Edition, 7.42, Cold Spring Harbor Laboratory Press, N.Y.), dot blotting method (Molecular Cloning, Third Edition, 7.46, Cold Spring Harbor Laboratory Press, N.Y.), RT-PCR method (Molecular Cloning, Third Edition, 8.46, Cold Spring Harbor Laboratory Press, N.Y.), and methods using the DNA chip (DNA array), and the like.

In addition, in the above-mentioned polymorphism, polymorphism involved with changes in amino acids can analyzed by using the expression product of gene that is a subject to analysis. In this case, material even being partial protein or partial peptide, can be used as a sample for analysis as long as it contains amino acids which correspond to the site of polymorphism.

Analysis methods using these expression products of gene may include: a method for directly analyzing amino acids at the site of polymorphism, a method for immunologically analyzing utilizing changes of three-dimensional structure, or the like. As the former, a well-known amino acid sequence analysis method (a method using Edman method) can be used. As the latter, ELISA (enzyme-linked immunosorbent assay) using the monoclonal antibody or polyclonal antibody which has binding activity specific to the expression product of gene which has any of genotypes that constitute polymorphism; radioimmunoassay, immunoprecipitation method, immunodiffusion method, and the like can be used.

Information about polymorphisms to be obtained by conducting the detection methods of the present invention described above can be used to diagnose a genetic risk of restenosis after coronary angioplasty. That is to say, the present invention also provides a method for diagnosing a genetic risk of restenosis after coronary angioplasty, which comprises a step of determining the genotype in a nucleic acid sample based on information about polymorphism that was obtained by the above-detection methods, and a step of assessing a genetic risk of restenosis after coronary angioplasty based on the determined genotype of the nucleic acid sample. Herein, the determination of the genotype is typically to determine which genotype both alleles of nucleic acid samples have with respect to the polymorphism to be detected. In the case where the subject to be detected is, for example, ApoE (3932T→C) polymorphism, the detection of genotype is typically, an investigation on what genotype that is, TT (the base at position 3932 is a homozygote of allele T), CT (the base at position 3932 is a heterozygote of allele T and allele C) or CC (the base at position 3932 is a homozygote of allele C), the apolipoprotein E gene has in a nucleic acid sample.

By considering the results obtained in Example mentioned below, in order to enable a diagnosis of genetic risk of restenosis after coronary angioplasty with high accuracy and high predictability, for example, in the case of the ApoE (3932T→C) polymorphism, it is determined whether the genotype in a nucleic acid sample is CC or TC, or TT. Similarly, in the case of the GPIa (1648A→G) polymorphism, it is determined whether the genotype is GG, or AG or AA; in the case of the TNFα (−863C→A) polymorphism, it is determined whether the genotype is AA or CA, or CC; in the case of the G-protein β3 (825C→T) polymorphism, it is determined whether the genotype is TT, or CT or CC; in the case of the ApoC-III (−482C→T) polymorphism, it is determined whether the genotype is TT or CT, or CC, or TT, or CT or CC; in the case of AGT (−6G→A) polymorphism, it is determined whether the genotype is AA or GA, or GG; in the case of TSP4 (1186G→C) polymorphism, it is determined whether the genotype is CC or GC, or GG; in the case of TM (2136C→T) polymorphism, it is determined whether the genotype is TT or CT, or CC; in the case of the TPO (5713A→G) polymorphism, it is determined whether the genotype is GG, or AG or AA; in the case of the PAF-AH (994G→T) polymorphism, it is determined whether the genotype is TT or GT, or GG; in the case of the E-selectin (561A→C) polymorphism, it is determined whether the genotype is CC or AC, or AA; in the case of glycoprotein FABP2 (2445G→A) polymorphism, it is determined whether the genotype is AA or GA, or GG; in the case of paraoxonase GPIbα (1018C→T) polymorphism, it is determined whether the genotype is TT or CT, or CC; in the case of PAI1 (−668/4G→5G) polymorphism, it is determined whether the genotype is 5G/5G or 4G/5G, or 4G/4G; in the case of PON (584G→A) polymorphism, it is determined whether the genotype is AA or GA, or GG.

Diagnosis of a genetic risk of restenosis after coronary angioplasty enables prediction of potentiality (susceptibility to development) in that restenosis might be developed after coronary angioplasty. That is to say, according to the diagnosis method of the present invention, it is possible to evaluate the risk of development of restenosis after coronary angioplasty. It is clinically significant that such an evaluation enables the selection of an appropriate treatment method in advance.

By utilizing the genetic information associated with the development of restenosis obtained by the present invention, it is possible to reduce the development rate of restenosis after coronary angioplasty. For example, as a result of carrying out the diagnostic method of the present invention, when the polymorphism to be analyzed is a genotype to increase the risk of development of restenosis, by introducing a gene having a genotype with low risk of development into a living body, due to the expression of the gene, the reduction of disease can be expected. The same treatment effect can be expected by a method including of introducing antisense strand with respect to mRNA of gene having a genotype with high risk of development of restenosis and suppressing the expression of the mRNA.

The introduction of such genes into the living body can be carried out by a method, for example, a method using a plasmid for gene introduction or a virus vector, electroporation (Potter, H. et al., Proc. Natl. Acad. Sci. U.S.A. 81, 7161-7165(1984), an ultrasonic microbubble (Lawrie, A., et al. Gene Therapy 7, 2023-2027 (2000)), lipofection (Felgner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73,366-370(1976)), and the like. By utilizing these methods, desired genes, etc. can be directly introduced (in vivo method) or indirectly introduced (ex vivo method).

Furthermore, by using an instrument such as a stent previously coated with gene, etc. (a gene held by a plasmid for introducing genes or virus vector may be coated), the above-mentioned gene introduction can be carried out at the same time or after the coronary angioplasty.

The second aspect of the present invention provides a kit to be used in the above-mentioned detecting method or diagnostic method in the present invention (a kit for detecting the genotype or a kit for diagnosing restenosis after coronary angioplasty). Such a kit contains nucleic acids (nucleic acids for analyzing polymorphism) for analyzing two or more polymorphisms selected from the group consisting of polymorphisms described in (1) to (6) above. As another embodiment, such a kit is constructed, which contains nucleic acids (nucleic acids for analyzing polymorphism) for analyzing two or more polymorphisms selected from the group consisting of polymorphisms described in (7) to (11) above. As a further embodiment, such a kit is constructed, which contains nucleic acids (nucleic acids for analyzing polymorphism) for analyzing two or more polymorphisms selected from the group consisting of polymorphisms described in (12) to (17) above. As a yet further embodiment, such a kit is constructed, which contains nucleic acids (nucleic acids for analyzing polymorphism) for analyzing two or more polymorphisms selected from the group consisting of polymorphisms described in (18) to (22) above.

In the analysis methods by which it is applied (a method which utilizes PCR using the above-mentioned allele-specific nucleic acids and the like, PCR-RFLP method, PCR-SSCP method, TaqMan-PCR method, Invader method, etc.), nucleic acids for analyzing polymorphism are designed as materials which can specifically amplifies (primer) or specifically detect (probe) the DNA region containing the polymorphism portion to be analyzed or mRNA which corresponds to the region. Concrete examples of kits to be provided according to the present invention are described below.

A kit for detecting the genotype, comprising two or more nucleic acids selected from the group consisting of the following (1) to (6):

(1) a nucleic acid having a sequence which is complementary to the partial DNA region containing the base at position 3932 of the apolipoprotein E gene whose base at position 3932 is T, or a nucleic acid having a sequence which is complementary to the partial DNA region containing the base at position 3932 of the apolipoprotein E gene whose base at position 3932 is C:

(2) a nucleic acid having a sequence which is complementary to the partial DNA region containing the base at position 1648 of the glycoprotein Ia gene whose base at position 1648 is A, or a nucleic acid having a sequence which is complementary to the partial DNA region containing the base at position 1648 of the glycoprotein Ia gene whose base at position 1648 is G:

(3) a nucleic acid having a sequence which is complementary to the partial DNA region containing the base at position −863 of the tumor necrosis factor-α gene whose base at position −863 is C, or a nucleic acid having a sequence which is complementary to the partial DNA region containing the base at position −863 of the tumor necrosis factor-α gene whose base at position −863 is A:

(4) a nucleic acid having a sequence which is complementary to the partial DNA region containing the base at position 825 of the G-protein β3 subunit gene whose base at position 825 is C, or a nucleic acid having a sequence which is complementary to the partial DNA region containing the base at position 825 of the G-protein β3 subunit gene whose base at position 825 is T:

(5) a nucleic acid having a sequence which is complementary to the partial DNA region containing the base at position −482 of the apolipoprotein C-III gene whose base at position −482 is C, or a nucleic acid having a sequence which is complementary to the partial DNA region containing the base at position −482 of the apolipoprotein C-III gene whose base at position −482 is T: and (6) a nucleic acid having a sequence which is complementary to the partial DNA region containing the base at position −6 of the angiotensinogen gene whose base at position −6 is G, or a nucleic acid having a sequence which is complementary to the partial DNA region containing the base at position −6 of the angiotensinogen gene whose base at position −6 is A.

In the above mention, kits are constructed by selecting two or more nucleic acids from the group consisting of (1) to (6). However, kits may be constructed by making a group consisting of two or more nucleic acids arbitrarily selected from (1) to (6) and selecting two or more nucleic acids from such a group. For example, kits may be constructed by selecting two or more nucleic acids from the group consisting of (1) to (5) (a set of nucleic acids for analyzing polymorphisms with five highest odds ratio and P values which are considered in Example mentioned below), or kits may be constructed by selecting two or more nucleic acids from the group consisting of (1), (3), (4) and (5) (nucleic acids for analyzing polymorphisms with four highest odds ratios in Example mentioned below).

A kit for detecting the genotype, comprising two or more nucleic acids selected from the group consisting of the following (7) to (11):

(7) a nucleic acid having a sequence which is complementary to the partial DNA region containing the base at position 1186 of the thrombospondin 4 gene whose base at position 1186 is G, or a nucleic acid having a sequence which is complementary to the partial DNA region containing the base at position 1186 of the thrombospondin 4 gene whose base at position 1186 is C;

(8) a nucleic acid having a sequence which is complementary to the partial DNA region containing the base at position −863 of the tumor necrosis factor-α gene whose base at position −863 is C, or a nucleic acid having a sequence which is complementary to the partial DNA region containing the base at position −863 of the tumor necrosis factor-α gene whose base at position −863 is A;

(9) a nucleic acid having a sequence which is complementary to the partial DNA region containing the base at position 2136 of the thrombomodulin gene whose base at position 2136 is C, or a nucleic acid having a sequence which is complementary to the partial DNA region containing the base at position 2136 of the thrombomodulin gene whose base at position 2136 is T;

(10) a nucleic acid having a sequence which is complementary to the partial DNA region containing the base at position 5713 of the thrombopoietin gene whose base at position 5713 is A, or a nucleic acid having a sequence which is complementary to the partial DNA region containing the base at position 5713 of the thrombopoietin gene whose base at position 5713 is G; and

(11) a nucleic acid having a sequence which is complementary to the partial DNA region containing the base at position 994 of the platelet-activating factor acetylhydrolase gene whose base at position 994 is G, or a nucleic acid having a sequence which is complementary to the partial DNA region containing the base at position 994 of the platelet-activating factor acetylhydrolase gene whose base at position 994 is T.

In the above mention, kits are constructed by selecting two or more nucleic acids from the group consisting of (7) to (11). However, kits may be constructed by making a group consisting of two or more nucleic acids arbitrarily selected from (7) to (11) and selecting two or more nucleic acids from such a group. For example, kits may be constructed by selecting two or more nucleic acids from the group consisting of (7) to (10) (nucleic acids for analyzing polymorphisms with four highest odds ratios in Example mentioned below), or kits may be constructed by selecting two or more nucleic acids from the group consisting of (7) to (9) (nucleic acids for analyzing polymorphisms with three highest odds ratios in Example mentioned below).

A kit for detecting the genotype, comprising two or more nucleic acids selected from the group consisting of the following (12) to (17):

(12) a nucleic acid having a sequence which is complementary to the partial DNA region containing the base at position 561 of the E-selectin gene whose base at position 561 is A, or a nucleic acid having a sequence which is complementary to the partial DNA region containing the base at position 561 of the E-selectin gene whose base at position 561 is C;

(13) a nucleic acid having a sequence which is complementary to the partial DNA region containing the base at position 2445 of the fatty acid-binding protein 2 gene whose base at position 2445 is G, or a nucleic acid having a sequence which is complementary to the partial DNA region containing the base at position 2445 of the fatty acid-binding protein 2 gene whose base at position 2445 is A;

(14) a nucleic acid having a sequence which is complementary to the partial DNA region containing the base at position 1018 of the glycoprotein Ibα gene whose base at position 1018 is C, or a nucleic acid having a sequence which is complementary to the partial DNA region containing the base at position 1018 of the glycoprotein Ibα gene whose base at position 1018 is T;

(15) a nucleic acid having a sequence which is complementary to the partial DNA region containing the part of sequence of the plasminogen activator inhibitor-1 gene in which four G successively exist in the 3' direction from the position −668, or a nucleic acid having a sequence which is complementary to the partial DNA region containing the part of sequence of the plasminogen activator inhibitor-1 gene in which five G successively exist in the 3' direction from the position −668;

(16) a nucleic acid having a sequence which is complementary to the partial DNA region containing the base at position 584 of the paraoxonase gene whose base at position 584 is G, or a nucleic acid having a sequence which is complementary to the partial DNA region containing the base at position 584 of the paraoxonase gene whose base at position 584 is A; and

(17) a nucleic acid having a sequence which is complementary to the partial DNA region containing the base at position 3932 of the apolipoprotein E gene whose base at position 3932 is T, or a nucleic acid having a sequence which is complementary to the partial DNA region containing the base at position 3932 of the apolipoprotein E gene whose base at position 3932 is C.

In the above mention, kits are constructed by selecting two or more nucleic acids from the group consisting of (12) to (17). However, kits may be constructed by making a group consisting of two or more nucleic acids arbitrarily selected from (12) to (17) and selecting two or more nucleic acids from such a group. For example, kits may be constructed by selecting two or more nucleic acids from the group consisting of (12) to (16) (nucleic acids for analyzing polymorphisms with five highest odds ratios in Example mentioned below), or kits may be constructed by selecting two or more nucleic acids from the group consisting of (12) to (15) (nucleic acids with four highest odds ratios in Example mentioned below).

A kit for detecting the genotype, comprising two or more nucleic acids selected from the group consisting of the following (18) to (22):

(18) a nucleic acid having a sequence which is complementary to the partial DNA region containing the part of sequence of the plasminogen activator inhibitor-1 gene in which four G successively exist in the 3' direction from the position −668, or a nucleic acid having a sequence which is complementary to the partial DNA region containing the part of sequence of the plasminogen activator inhibitor-1 gene in which five G successively exist in the 3' direction from the position −668;

(19) a nucleic acid having a sequence which is complementary to the partial DNA region containing the base at position −482 of the apolipoprotein C-III gene whose base at position −482 is C, or a nucleic acid having a sequence which is complementary to the partial DNA region containing the base at position −482 of the apolipoprotein C-III gene whose base at position −482 is T;

(20) a nucleic acid having a sequence which is complementary to the partial DNA region containing the base at position 584 of the paraoxonase gene whose base at position 584 is G, or a nucleic acid having a sequence which is complementary to the partial DNA region containing the base at position 584 of the paraoxonase gene whose base at position 584 is A;

(21) a nucleic acid having a sequence which is complementary to the partial DNA region containing the base at position 1018 of the glycoprotein Ibα gene whose base at position 1018 is C, or a nucleic acid having a sequence which is complementary to the partial DNA region containing the base at position 1018 of the glycoprotein Ibα gene whose base at position 1018 is T; and

(22) a nucleic acid having a sequence which is complementary to the partial DNA region containing the base at position 3932 of the apolipoprotein E gene whose base at position 3932 is T, or a nucleic acid having a sequence which is complementary to the partial DNA region containing the base at position 3932 of the apolipoprotein E gene whose base at position 3932 is C.

In the above mention, kits are constructed by selecting two or more nucleic acids from the group consisting of (18) to (22). However, kits may be constructed by making a group consisting of two or more nucleic acids arbitrarily selected from (18) to (22) and selecting two or more nucleic acids from such a group. For example, kits may be constructed by selecting two or more nucleic acids from the group consisting of (18) to (21) (nucleic acids for analyzing polymorphisms with four highest odds ratios in Example mentioned below), or kits may be constructed by selecting two or more nucleic acids from the group consisting of (18) to (20) (nucleic acids for analyzing polymorphisms with three highest odds ratios in Example mentioned below).

A kit for detecting the genotype, comprising two or more sets of nucleic acids selected from the group consisting of the following (1) to (6):

(1) a set of nucleic acids which is designed to specifically amplify the partial DNA region containing the base at position 3932 of the apolipoprotein E gene only in the case where the base at position 3932 of the apolipoprotein E gene in a nucleic acid sample is T, or a set of nucleic acids which is designed to specifically amplify the partial DNA region containing the base at position 3932 of the apolipoprotein E gene only in the case where the base at position 3932 of the apolipoprotein E gene in a nucleic acid sample is C;

(2) a set of nucleic acids which is designed to specifically amplify the partial DNA region containing the base at position 1648 of the glycoprotein Ia gene only in the case where the base at position 1648 of the glycoprotein Ia gene in a nucleic acid sample is A, or a set of nucleic acids which is designed to specifically amplify the partial DNA region containing the base at position 1648 of the glycoprotein Ia gene only in the case where the base at position 1648 of the glycoprotein Ia gene in a nucleic acid sample is G;

(3) a set of nucleic acids which is designed to specifically amplify the partial DNA region containing the base at position −863 of the tumor necrosis factor-α gene only in the case where the base at position −863 of the tumor necrosis factor-α gene in a nucleic acid sample is C, or a set of nucleic acids which is designed to specifically amplify the partial DNA region containing the base at position −863 of the tumor necrosis factor-α gene only in the case where the base at position −863 of the glycoprotein Ia gene in a nucleic acid sample is A;

(4) a set of nucleic acids which is designed to specifically amplify the partial DNA region containing the base at position 825 of the G-protein β3 subunit gene only in the case where the base at position 825 of the G-protein β3 subunit gene in a nucleic acid sample is C, or a set of nucleic acids which is designed to specifically amplify the partial DNA region containing the base at position 825 of the G-protein β3 subunit gene only in the case where the base at position 825 of the G-protein β3 subunit gene in a nucleic acid sample is T;

(5) a set of nucleic acids which is designed to specifically amplify the partial DNA region containing the base at position −482 of the apolipoprotein C-III gene only in the case where the base at position −482 of the apolipoprotein C-III gene in a nucleic acid sample is C, or a set of nucleic acids which is designed to specifically amplify the partial DNA region containing the base at position −482 of the apolipoprotein C-III gene only in the case where the base at position −482 of the apolipoprotein C-III gene in a nucleic acid sample is T; and (6) a set of nucleic acids which is designed to specifically amplify the partial DNA region containing the base at position −6 of the angiotensinogen gene only in the case where the base at position −6 of the angiotensinogen gene in a nucleic acid sample is G, or a set of nucleic acids which is designed to specifically amplify the partial DNA region containing the base at position −6 of the angiotensinogen gene only in the case where the base at position −6 of the angiotensinogen gene in a nucleic acid sample is A.

In the above mention, kits are constructed by selecting two or more sets of nucleic acids from the group consisting of (1) to (6). However, kits may be constructed by making a group consisting of two or more sets of nucleic acids arbitrarily selected from (1) to (6) and selecting two or more sets of nucleic acids from such a group. For example, kits may be constructed by selecting two or more sets of nucleic acids from the group consisting of (1) to (5) (sets of nucleic acids for analyzing polymorphisms with five highest odds ratio and P values which are considered in Example mentioned below), or kits may be constructed by selecting two or more sets of nucleic acids from the group consisting of (1), (3), (4) and (5) (nucleic acids for analyzing polymorphisms with four highest odds ratios in Example mentioned below).

A kit for detecting the genotype, comprising two or more sets of nucleic acids selected from the group consisting of the following (7) to (11):

(7) a set of nucleic acids which is designed to specifically amplify the partial DNA region containing the base at position 1186 of the thrombospondin 4 gene only in the case where the base at position 1186 of the thrombospondin 4 gene in a nucleic acid sample is G, or a set of nucleic acids which is designed to specifically amplify the partial DNA region containing the base at position 1186 of the thrombospondin 4 gene only in the case where the base at position 1186 of the thrombospondin 4 gene in a nucleic acid sample is C;

(8) a set of nucleic acids which is designed to specifically amplify the partial DNA region containing the base at position −863 of the tumor necrosis factor-α gene only in the case where the base at position −863 of the tumor necrosis factor-α gene in a nucleic acid sample is C, or a set of nucleic acids which is designed to specifically amplify the partial DNA region containing the base at position −863 of the tumor necrosis factor-α gene only in the case where the base at position −863 of the tumor necrosis factor-α gene in a nucleic acid sample is A;

(9) a set of nucleic acids which is designed to specifically amplify the partial DNA region containing the base at position 2136 of the thrombomodulin gene only in the case where the base at position 2136 of the thrombomodulin gene in a nucleic acid sample is C, or a set of nucleic acids which is designed to specifically amplify the partial DNA region containing the base at position 2136 of the thrombomodulin gene only in the case where the base at position 2136 of the thrombomodulin gene in a nucleic acid sample is T;

(10) a set of nucleic acids which is designed to specifically amplify the partial DNA region containing the base at position 5713 of the thrombopoietin gene only in the case where the base at position 5713 of the thrombopoietin gene in a nucleic acid sample is A, or a set of nucleic acids which is designed to specifically amplify the partial DNA region containing the base at position 5713 of the thrombopoietin gene only in the case where the base at position 5713 of the thrombopoietin gene in a nucleic acid sample is G; and

(11) a set of nucleic acids which is designed to specifically amplify the partial DNA region containing the base at position 994 of the platelet-activating factor acetylhydrolase gene only in the case where the base at position 994 of the platelet-activating factor acetylhydrolase gene in a nucleic acid sample is G or a set of nucleic acids which is designed to specifically amplify the partial DNA region containing the base at position 994 of the platelet-activating factor acetylhydrolase gene only in the case where the base at position 994 of the platelet-activating factor acetylhydrolase gene in a nucleic acid sample is T.

In the above mention, kits are constructed by selecting two or more sets of nucleic acids from the group consisting of (7) to (11). However, kits may be constructed by making a group consisting of two or more sets of nucleic acids arbitrarily selected from (7) to (11) and selecting two or more sets of nucleic acids from such a group. For example, kits may be constructed by selecting two or more sets of nucleic acids from the group consisting of (7) to (10) (sets of nucleic acids for analyzing polymorphisms with four highest odds ratio in Example mentioned below), or kits may be constructed by selecting two or more sets of nucleic acids from the group consisting of (7) to (9) (sets of nucleic acids for analyzing polymorphisms with three highest odds ratio in Example mentioned below).

A kit for detecting the genotype, comprising two or more sets of nucleic acids selected from the group consisting of the following (12) to (17):

(12) a set of nucleic acids which is designed to specifically amplify the partial DNA region containing the base at position 561 of the E-selectin gene only in the case where the base at position 561 of the E-selectin gene in a nucleic acid sample is A, or a set of nucleic acids which is designed to specifically amplify the partial DNA region containing the base at position 561 of the E-selectin gene only in the case where the base at position 561 of the E-selectin gene in a nucleic acid sample is C;

(13) a set of nucleic acids which is designed to specifically amplify the partial DNA region containing the base at position 2445 of the fatty acid-binding protein 2 gene only in the case where the base at position 2445 of the fatty acid-binding protein 2 gene in a nucleic acid sample is G, or a set of nucleic acids which is designed to specifically amplify the partial DNA region containing the base at position 2445 of the fatty acid-binding protein 2 gene only in the case where the base at position 2445 of the fatty acid-binding protein 2 gene in a nucleic acid sample is A;

(14) a set of nucleic acids which is designed to specifically amplify the partial DNA region containing the base at position 1018 of the glycoprotein Ibα gene only in the case where the base at position 1018 of the glycoprotein Ibα gene in a nucleic acid sample is C, or a set of nucleic acids which is designed to specifically amplify the partial DNA region containing the base at position 1018 of the glycoprotein Ibα gene only in the case where the base at position 1018 of the glycoprotein Ibα gene in a nucleic acid sample is T;

(15) a set of nucleic acids which is designed to specifically amplify a partial DNA region containing the part of sequence of the plasminogen activator inhibitor-1 gene only in the case where four G successively exist in the 3' direction from the position −668 in the plasminogen activator inhibitor-1 gene in a nucleic sample, or a set of nucleic acids which is designed to specifically amplify a partial DNA region containing the part of sequence of the plasminogen activator inhibitor-1 gene only in the case where five G successively exist in the 3' direction from the position −668 in the plasminogen activator inhibitor-1 gene in a nucleic sample;

(16) a set of nucleic acids which is designed to specifically amplify the partial DNA region containing the base at position 584 of the paraoxonase gene only in the case where the base at position 584 of the paraoxonase gene in a nucleic acid sample is G, or a set of nucleic acids which is designed to specifically amplify the partial DNA region containing the base at position 584 of the paraoxonase gene only in the case where the base at position 584 of the paraoxonase gene in a nucleic acid sample is A; and

(17) a set of nucleic acids which is designed to specifically amplify the partial DNA region containing the base at position 3932 of the apolipoprotein E gene only in the case where the base at position 3932 of the apolipoprotein E gene in a nucleic acid sample is T, or a set of nucleic acids which is designed to specifically amplify the partial DNA region containing the base at position 3932 of the apolipoprotein E gene only in the case where the base at position 3932 of the apolipoprotein E gene in a nucleic acid sample is C.

In the above mention, kits are constructed by selecting two or more sets of nucleic acids from the group consisting of (12) to (17). However, kits may be constructed by making a group consisting of two or more sets of nucleic acids arbitrarily selected from (12) to (17) and selecting two or more sets of nucleic acids from such a group. For example, kits may be constructed by selecting two or more sets of nucleic acids from the group consisting of (12) to (16) (sets of nucleic acids for analyzing polymorphisms with five highest odds ratios in Example mentioned below), or kits may be constructed by selecting two or more sets of nucleic acids from the group consisting of (12) to (15) (sets of nucleic acids for analyzing polymorphisms with four highest odds ratios in Example mentioned below).

A kit for detecting the genotype, comprising two or more sets of nucleic acids selected from the group consisting of the following (18) to (22):

(18) a set of nucleic acids which is designed to specifically amplify a partial DNA region containing the part of sequence of the plasminogen activator inhibitor-1 gene only in the case where four G successively exist in the 3' direction from the position −668 in the plasminogen activator inhibitor-1 gene in a nucleic sample, or a set of nucleic acids which is designed to specifically amplify a partial DNA region containing the part of sequence of the plasminogen activator inhibitor-1 gene only in the case where five G successively exist in the 3' direction from the position −668 in the plasminogen activator inhibitor-1 gene in a nucleic sample;

(19) a set of nucleic acids which is designed to specifically amplify the partial DNA region containing the base at position −482 of the apolipoprotein C-III gene only in the case where the base at position −482 of the apolipoprotein C-III gene in a nucleic acid sample is C, or a set of nucleic acids which is designed to specifically amplify the partial DNA region containing the base at position −482 of the apolipoprotein C-III gene only in the case where the base at position −482 of the apolipoprotein C-III gene in a nucleic acid sample is T;

(20) a set of nucleic acids which is designed to specifically amplify the partial DNA region containing the base at position 584 of the paraoxonase gene only in the case where the base at position 584 of the paraoxonase gene in a nucleic acid sample is G, or a set of nucleic acids which is designed to specifically amplify the partial DNA region containing the base at position 584 of the paraoxonase gene only in the case where the base at position 584 of the paraoxonase gene in a nucleic acid sample is A;

(21) a set of nucleic acids which is designed to specifically amplify the partial DNA region containing the base at position 1018 of the glycoprotein Ibα gene only in the case where the base at position 1018 of the glycoprotein Ibα gene in a nucleic acid sample is C, or a set of nucleic acids which is designed to specifically amplify the partial DNA region containing the base at position 1018 of the glycoprotein Ibα gene only in the case where the base at position 1018 of the glycoprotein Ibα gene in a nucleic acid sample is T; and

(22) a set of nucleic acids which is designed to specifically amplify the partial DNA region containing the base at position 3932 of the apolipoprotein E gene only in the case where the base at position 3932 of the apolipoprotein E gene in a nucleic acid sample is T, or a set of nucleic acids which is designed to specifically amplify the partial DNA region containing the base at position 3932 of the apolipoprotein E gene only in the case where the base at position 3932 of the apolipoprotein E gene in a nucleic acid sample is C.

In the above mention, kits are constructed by selecting two or more sets of nucleic acids from the group consisting of (18) to (22). However, kits may be constructed by making a group consisting of two or more sets of nucleic acids arbitrarily selected from (18) to (22) and selecting two or more sets of nucleic acids from such a group. For example, kits may be constructed by selecting two or more sets of nucleic acids from the group consisting of (18) to (21) (sets of nucleic acids for analyzing polymorphisms with four highest odds ratio in Example mentioned below), or kits may be constructed by selecting two or more sets of nucleic acids from the group consisting of (18) to (20) (sets of nucleic acid for analyzing polymorphisms with three highest odds ratios in Example mentioned below).

A kit for detecting the genotype, comprising two or more sets of nucleic acids selected from the group consisting of the following (1) to (6):

(1) a set of nucleic acids which is designed to specifically amplify the partial DNA region containing the base at position 3932 of the apolipoprotein E gene and which consists of a sense primer that specifically hybridizes the partial DNA region containing the base at position 3932 of the apolipoprotein E gene whose base at position 3932 is T and/or a sense primer that specifically hybridizes the partial DNA region containing the base at position 3932 of the apolipoprotein E gene whose gene at position 3932 is C and of an antisense primer that specifically hybridizes a partial region of the apolipoprotein E gene;

(2) a set of nucleic acids which is designed to specifically amplify the partial DNA region containing the base at position 1648 of the glycoprotein Ia gene and which consists of a sense primer that specifically hybridizes the partial DNA region containing the base at position 1648 of the glycoprotein Ia gene whose base at position 1648 is A and/or a sense primer that specifically hybridizes the partial DNA region containing the base at position 1648 of the glycoprotein Ia gene whose gene at position 1648 is G and of an antisense primer that specifically hybridizes a partial region of the glycoprotein Ia gene;

(3) a set of nucleic acids which is designed to specifically amplify the partial DNA region containing the base at position −863 of the tumor necrosis factor-α gene and which consists of an antisense primer that specifically hybridizes the partial DNA region containing the base at position −863 of the tumor necrosis factor-α gene whose base at position −863 is C and/or an antisense primer that specifically hybridizes the partial DNA region containing the base at position −863 of the tumor necrosis factor-α gene whose gene at position −863 is A and of a sense primer that specifically hybridizes a partial region of the tumor necrosis factor-α gene;

(4) a set of nucleic acids which is designed to specifically amplify the partial DNA region containing the base at position 825 of the G-protein ≈3 subunit gene and which consists of a sense primer that specifically hybridizes the partial DNA region containing the base at position 825 of the G-protein β3 subunit gene whose base at position 825 is C and/or a sense primer that specifically hybridizes the partial DNA region containing the base at position 825 of the G-protein β3 subunit gene whose gene at position 825 is T and of an antisense primer that specifically hybridizes a partial region of the G-protein β3 subunit gene;

(5) a set of nucleic acids which is designed to specifically amplify the partial DNA region containing the base at position −482 of the apolipoprotein C-III gene and which consists of a sense primer that specifically hybridizes the partial DNA region containing the base at position −482 of the apolipoprotein C-III gene whose base at position −482 is C and/or a sense primer that specifically hybridizes the partial DNA region containing the base at position −482 of the apolipoprotein C-III gene whose gene at position −482 is T and of an antisense primer that specifically hybridizes a partial region of the apolipoprotein C-III gene; and (6) a set of nucleic acids which is designed to specifically amplify the partial DNA region containing the base at position -6 of the angiotensinogen gene and which consists of an antisense primer that specifically hybridizes the partial DNA region containing the base at position −6 of the angiotensinogen gene whose base at position −6 is G and/or an antisense primer that specifically hybridizes the partial DNA region containing the base at position -6 of the angiotensinogen gene whose gene at position −6 is A and of a sense primer that specifically hybridizes a partial region of the angiotensinogen gene.

In the above mention, kits are constructed by selecting two or more sets of nucleic acids from the group consisting of (1) to (6). However, kits may be constructed by making a group consisting of two or more sets of nucleic acids arbitrarily selected from (1) to (6) and selecting two or more sets of nucleic acids from such a group. For example, kits may be constructed by selecting two or more nucleic acids from the group consisting of (1) to (5) (sets of nucleic acids for analyzing polymorphisms with five highest odds ratio and P values which are considered in Example mentioned below), or kits may be constructed by selecting two or more sets of nucleic acids from the group consisting of (1), (3), (4) and (5) (sets of nucleic acids for analyzing polymorphisms with four highest odds ratios in Example mentioned below).

A kit for detecting the genotype, comprising two or more sets of nucleic acids selected from the group consisting of the following (7) to (11):

(7) a set of nucleic acids which is designed to specifically amplify the partial DNA region containing the base at position 1186 of the thrombospondin 4 gene and which consists of a sense primer that specifically hybridizes the partial DNA region containing the base at position 1186 of the thrombospondin 4 gene whose base at position 1186 is G and/or a sense primer that specifically hybridizes the partial DNA region containing the base at position 1186 of the thrombospondin 4 gene whose gene at position 1186 is C and of an antisense primer that specifically hybridizes a partial region of the thrombospondin 4 gene;

(8) a set of nucleic acids which is designed to specifically amplify the partial DNA region containing the base at position −863 of the tumor necrosis factor-α gene and which consists of an antisense primer that specifically hybridizes the partial DNA region containing the base at position −863 of the tumor necrosis factor-α gene whose base at position −863 is C and/or an antisense primer that specifically hybridizes the partial DNA region containing the base at position −863 of the tumor necrosis factor-α gene whose gene at position −863 is A and of a sense primer that specifically hybridizes a partial region of the tumor necrosis factor-α gene;

(9) a set of nucleic acids which is designed to specifically amplify the partial DNA region containing the base at position 2136 of the thrombomodulin gene and which consists of a sense primer that specifically hybridizes the partial DNA region containing the base at position 2136 of the thrombomodulin gene whose base at position 2136 is C and/or a sense primer that specifically hybridizes the partial DNA region containing the base at position 2136 of the thrombomodulin gene whose gene at position 2136 is T and of an antisense primer that specifically hybridizes a partial region of the thrombomodulin gene;

(10) a set of nucleic acids which is designed to specifically amplify the partial DNA region containing the base at position 5713 of the thrombopoietin gene and which consists of a sense primer that specifically hybridizes the partial DNA region containing the base at position 5713 of the thrombopoietin gene whose base at position 5713 is A and/or a sense primer that specifically hybridizes the partial DNA region containing the base at position 5713 of the thrombopoietin gene whose gene at position 5713 is G and of an antisense primer that specifically hybridizes a partial region of the thrombopoietin gene; and

(11) a set of nucleic acids which is designed to specifically amplify the partial DNA region containing the base at position 994 of the platelet-activating factor acetylhydrolase gene and which consists of a sense primer that specifically hybridizes the partial DNA region containing the base at position 994 of the platelet-activating factor acetylhydrolase gene whose base at position 994 is G and/or a sense primer that specifically hybridizes the partial DNA region containing the base at position 994 of the platelet-activating factor acetylhydrolase gene whose gene at position 994 is T and of an antisense primer that specifically hybridizes a partial region of the platelet-activating factor acetylhydrolase gene.

In the above mention, kits are constructed by selecting two or more sets of nucleic acids from the group consisting of (7) to (11). However, kits may be constructed by making a group consisting of two or more sets of nucleic acids arbitrarily selected from (7) to (11) and selecting two or more sets of nucleic acids from such a group. For example, kits may be constructed by selecting two or more nucleic acids from the group consisting of (7) to (10) (sets of nucleic acids for analyzing polymorphisms with four highest odds ratio in Example mentioned below), or kits may be constructed by selecting two or more sets of nucleic acids from the group consisting of (7) to (9) (sets of nucleic acids for analyzing polymorphisms with three highest odds ratios in Example mentioned below).

A kit for detecting the genotype comprising two or more sets of nucleic acids selected from the group consisting of the following (12) to (17);

(12) a set of nucleic acids which is designed to specifically amplify the partial DNA region containing the base at position 561 of the E-selectin gene and which consists of an antisense primer that specifically hybridizes the partial DNA region containing the base at position 561 of the E-selectin gene whose base at position 561 is A and/or an antisense primer that specifically hybridizes the partial DNA region containing the base at position 561 of the E-selectin gene whose gene at position 561 is C and of a sense primer that specifically hybridizes a partial region of the E-selectin gene;

(13) a set of nucleic acids which is designed to specifically amplify the partial DNA region containing the base at position 2445 of the fatty acid-binding protein 2 gene and which consists of a sense primer that specifically hybridizes the partial DNA region containing the base at position 2445 of the fatty acid-binding protein 2 gene whose base at position 2445 is G and/or a sense primer that specifically hybridizes the partial DNA region containing the base at position 2445 of the fatty acid-binding protein 2 gene whose gene at position 2445 is A and of an antisense primer that specifically hybridizes a partial region of the fatty acid-binding protein 2 gene;

(14) a set of nucleic acids which is designed to specifically amplify the partial DNA region containing the base at position 1018 of the glycoprotein Ibα gene and which consists of a sense primer that specifically hybridizes the partial DNA region containing the base at position 1018 of the glycoprotein Ibα gene whose base at position 1018 is C, and/or a sense primer that specifically hybridizes the partial DNA region containing the base at position 1018 of the glycoprotein Ibα gene whose base at position 1018 is T, and of an antisense primer that specifically hybridizes a partial region of the glycoprotein Ibα gene;

(15) a set of nucleic acids consisting of a pair of primers which are designed to specifically amplify the partial DNA region containing a part of polymorphism at position −668 of the plasminogen activator inhibitor 1 gene, as well as a probe that specifically hybridizes the partial DNA region containing the sequence in the plasminogen activator inhibitor 1 gene in which four G successively exist in the 3' direction from the position −668 and/or a probe that-specifically hybridizes the partial DNA region containing the sequence in the plasminogen activator inhibitor 1 gene in which five G successively exist in the 3' direction from the position −668;

(16) a set of nucleic acids which is designed to specifically amplify the partial DNA region containing a base at position 584 of the paraoxonase gene and which consists of a sense primer that specifically hybridizes the partial DNA region containing the base at position 584 of the paraoxonase gene whose base at position 584 is G. and/or a sense primer that specifically hybridizes the partial DNA region containing the base at position 584 of the paraoxonase gene whose base at position 584 is A, and of an antisense primer that specifically hybridizes a partial region of the paraoxonase gene; and

(17) a set of nucleic acids which is designed to specifically amplify the partial DNA region containing a base at position 3932 of the apolipoprotein E gene and which consists of a sense primer that specifically hybridizes the partial DNA region containing the base at position 3932 of the apolipoprotein E gene whose base at position 3932 is T, and/or a sense primer that specifically hybridizes the partial DNA region containing the base at position 3932 of the apolipoprotein E gene whose gene at position 3932 is C, and an antisense primer that specifically hybridizes a partial region of the apolipoprotein E gene.

In the above mention, kits are constructed by selecting two or more nucleic acids from the group consisting of (12) to (17). However, kits may be constructed by making a group consisting of two or more nucleic acids arbitrarily selected from (12) to (17) and selecting two or more nucleic acids from such a group. For example, kits may be constructed by selecting two or more nucleic acids from the group consisting of (12) to (16) (sets of nucleic acids for analyzing polymorphisms with five highest odds ratios in Example mentioned below), or kits may be constructed by selecting two or more nucleic acids from the group consisting of (12) to (15) (sets of nucleic acids for analyzing polymorphisms with four highest odds ratios in Example mentioned below).

A kit for detecting the genotype, comprising two or more sets of nucleic acids selected from the group consisting of the following (18) to (22):

(18) a set of nucleic acids consisting of a pair of primers which are designed to specifically amplify the partial DNA region containing a part of polymorphism at position −668 of the plasminogen activator inhibitor 1 gene, as well as of a probe that specifically hybridizes the partial DNA region containing the sequence in the plasminogen activator inhibitor 1 gene in which four G successively exist in the 3' direction from the position −668 and/or of a probe that specifically hybridizes the partial DNA region containing the sequence in the plasminogen activator inhibitor 1 gene in which five G successively exist in the 3' direction from the position −668;

(19) a set of nucleic acids which is designed to specifically amplify the partial DNA region containing the base at position −482 of the apolipoprotein C-III gene and which consists of a sense primer that specifically hybridizes the partial DNA region containing the base at position −482 of the apolipoprotein C-III gene whose base at position −482 is C, and/or a sense primer that specifically hybridizes the partial DNA region containing the base at position −482 of the apolipoprotein C-III gene whose base at position −482 is T, and of an antisense primer that specifically hybridizes a partial region of the apolipoprotein C-III gene;

(20) a set of nucleic acids which is designed to specifically amplify the partial DNA region containing a base at position 584 of the paraoxonase gene and which consists of a sense primer that specifically hybridizes the partial DNA region containing the base at position 584 of the paraoxonase gene whose base at position 584 is G, and/or a sense primer that specifically hybridizes the partial DNA region containing the base at position 584 of the paraoxonase gene whose base at position 584 is A, and of an antisense primer that specifically hybridizes a partial region of the paraoxonase gene;

(21) a set of nucleic acids which is designed to specifically amplify the partial DNA region containing a base at position 1018 of the glycoprotein Ibα gene and which consists of a sense primer that specifically hybridizes the partial DNA region containing the base at position 1018 of the glycoprotein Ibα gene whose base at position 1018 is C, and/or a sense primer that specifically hybridizes the partial DNA region containing the base at position 1018 of the glycoprotein Ibα gene whose base at position 1018 is T, and of an antisense primer that specifically hybridizes a partial region of region of the glycoprotein Ibα gene; and

(22) a set of nucleic acids which is designed to specifically amplify the partial DNA region containing a base at position 3932 of the apolipoprotein E gene and which consists of a sense primer that specifically hybridizes the partial DNA region containing the base at position 3932 of the apolipoprotein E gene whose base at position 3932 is T, and/or a sense primer that specifically hybridizes the partial DNA region containing the base at position 3932 of the apolipoprotein E gene whose base at position 3932 is C, and of an antisense primer that specifically hybridizes a partial region of the apolipoprotein E gene.

In the above mention, kits are constructed by selecting two or more sets of nucleic acids from the group consisting of (18) to (22). However, kits may be constructed by making a group consisting of two or more sets of nucleic acids arbitrarily selected from (18) to (22) and selecting two or more sets of nucleic acids from such a group. For example, kits may be constructed by selecting two or more nucleic acids from the group consisting of (18) to (21) (sets of nucleic acids for analyzing polymorphisms with four highest odds ratios in Example mentioned below), or kits may be constructed by selecting two or more sets of nucleic acids from the group consisting of (18) to (20) (sets of nucleic acid for analyzing polymorphisms with three highest odds ratios in Example mentioned below).

A kit for detecting the genotype comprising two or more sets of nucleic acids selected from the group consisting of the following (1) to (6);

(1) a set of nucleic acids which consists of a first nucleic acid that specifically hybridizes a partial region containing the base corresponding to the base at position 3932 in the antisense strand of the apolipoprotein E gene whose base at position 3932 is T and that is labeled with a first labeling substance, of a second nucleic acid that specifically hybridizes a partial region containing the base corresponding to the base at position 3932 in the antisense strand of the apolipoprotein E gene whose base at position 3932 is C and that is labeled with a second labeling substance, and of the third nucleic acid that specifically hybridizes a partial region in the sense strand of the apolipoprotein E gene and that can specifically amplify the partial DNA region containing the base at position 3932 of the apolipoprotein E gene in concurrent use with the above first or second nucleic acid;

(2) a set of nucleic acids which consists of a first nucleic acid that specifically hybridizes a partial region containing the base at position 1648 in the antisense strand of the glycoprotein Ia gene whose base at position 1648 is A and that is labeled with a first labeling substance, of a second nucleic acid that specifically hybridizes a partial region containing the base at position 1648 in the antisense strand of the glycoprotein Ia gene whose base at position 1648 is G and that is labeled with a second labeling substance, and of the third nucleic acid that specifically hybridizes a partial region in the sense strand of the glycoprotein Ia gene and that can specifically amplify the partial DNA region containing the base at position 1648 of the glycoprotein Ia gene in concurrent use with the above first or second nucleic acid;

(3) a set of nucleic acids which consists of a first nucleic acid that specifically hybridizes a partial region containing the base at position −863 in the sense strand of the tumor necrosis factor α gene whose base at position −863 is C and that is labeled with a first labeling substance, of a second nucleic acid that specifically hybridizes a partial region containing the base at position −863 in the sense strand of the tumor necrosis factor α gene whose base at position −863 is A and that is labeled with a second labeling substance, and of the third nucleic acid that specifically hybridizes a partial region in the antisense strand of the tumor necrosis factor α gene and that can specifically amplify the partial DNA region containing the base at position −863 of the tumor necrosis factor α in concurrent use with the above first or second nucleic acid;

(4) a set of nucleic acids which consists of a first nucleic acid that specifically hybridizes a partial region containing the base at position 825 in the antisense strand of the G-protein β3 subunit gene whose base at position 825 is C and that is labeled with a first labeling substance, of a second nucleic acid that specifically hybridizes a partial region containing the base at position 825 in the antisense strand of the G-protein β3 subunit gene whose base at position 825 is T and that is labeled with a second labeling substance, and of the third nucleic acid that specifically hybridizes a partial region in the sense strand of the G-protein β3 subunit gene and that can specifically amplify the partial DNA region containing the base at position 825 of the G-protein β3 subunit gene in concurrent use with the above first or second nucleic acid;

(5) a set of nucleic acids which consists of a first nucleic acid that specifically hybridizes a partial region containing the base corresponding to the base at position −482 in the antisense strand of the apolipoprotein C-III gene whose base at position −482 is C and that is labeled with a first labeling substance, of a second nucleic acid that specifically hybridizes a partial region containing the base corresponding to the base at position −482 in the antisense strand of the apolipoprotein C-III gene whose base at position −482 is T and that is labeled with a second labeling substance, and of the third nucleic acid that specifically hybridizes a partial region in the sense strand of the apolipoprotein C-III gene and that can specifically amplify the partial DNA region containing the base at position −482 of the apolipoprotein C-III gene in concurrent use with the above first or second nucleic acid; and (6) a set of nucleic acids which consists of a first nucleic acid that specifically hybridizes a partial region containing the base at position −6 in the sense strand of the angiotensinogen gene whose base at position −6 is G and that is labeled with a first labeling substance, of a second nucleic acid that specifically hybridizes a partial region containing the base at position −6 in the sense strand of the angiotensinogen gene whose base at position −6 is A and that is labeled with a second labeling substance, and of the third nucleic acid that specifically hybridizes a partial region in the antisense strand of the angiotensinogen gene and that can specifically amplify the partial DNA region containing the base at position -6 of the angiotensinogen in concurrent use with the above first or second nucleic acid.

In the above mention, kits are constructed by selecting two or more sets of nucleic acids from the group consisting of (1) to (6). However, kits may be constructed by making a group consisting of two or more sets of nucleic acids arbitrarily selected from (1) to (6) and selecting two or more sets of nucleic acids from such a group. For example, kits may be constructed by selecting two or more sets of nucleic acids from the group consisting of (1) to (5) (sets of nucleic acids for analyzing polymorphisms with five highest odds ratios and P values which are considered in Example mentioned below), or kits may be constructed by selecting two or more sets of nucleic acids from the group consisting of (1), (3), (4) and (5) (sets of nucleic acids for analyzing polymorphisms with four highest odds ratios in Example mentioned below).

A kit for detecting the genotype comprising two or more sets of nucleic acids selected from the group consisting of the following (7) to (11);

(7) a set of nucleic acids which consists of a first nucleic acid that specifically hybridizes a partial region containing the base corresponding to the base at position 1186 in the antisense strand of the thrombospondin 4 gene whose base at position 1186 is G and that is labeled with a first labeling substance, of a second nucleic acid that specifically hybridizes a partial region containing the base corresponding to the base at position 1186 in the antisense strand of the thrombospondin 4 gene whose base at position 1186 is C and that is labeled with a second labeling substance, and of the third nucleic acid that specifically hybridizes a partial region in the sense strand of the thrombospondin 4 gene and that can specifically amplify the partial DNA region containing the base at position 1186 of the thrombospondin 4 gene in concurrent use with the above first or second nucleic acid;

(8) a set of nucleic acids which consists of a first nucleic acid that specifically hybridizes a partial region containing the base at position −863 in the sense strand of the tumor necrosis factor α gene whose base at position −863 is C and that is labeled with a first labeling substance, of a second nucleic acid that specifically hybridizes a partial region containing the base at position −863 in the sense strand of the tumor necrosis factor α gene whose base at position −863 is A and that is labeled with a second labeling substance, and of the third nucleic acid that specifically hybridizes a partial region in the antisense strand of the tumor necrosis factor α gene and that can specifically amplify the partial DNA region containing the base at position −863 of the tumor necrosis factor α in concurrent use with the above first or second nucleic acid;

(9) a set of nucleic acids which consists of a first nucleic acid that specifically hybridizes a partial region containing the base at position 2136 in the antisense strand of the thrombomodulin gene whose base at position 2136 is C and that is labeled with a first labeling substance, of a second nucleic acid that specifically hybridizes a partial region containing the base at position 2136 in the antisense strand of the thrombomodulin gene whose base at position 2136 is T and that is labeled with a second labeling substance, and of the third nucleic acid that specifically hybridizes a partial region in the sense strand of the thrombomodulin gene and that can specifically amplify the partial DNA region containing the base at position 2136 of the thrombomodulin gene in concurrent use with the above first or second nucleic acid;

(10) a set of nucleic acids which consists of a first nucleic acid that specifically hybridizes a partial region containing the base at position 5713 in the antisense strand of the thrombopoietin gene whose base at position 5713 is A and that is labeled with a first labeling substance, of a second nucleic acid that specifically hybridizes a partial region containing the base at position 5713 in the antisense strand of the thrombopoietin gene whose base at position 5713 is G and that is labeled with a second labeling substance, and of the third nucleic acid that specifically hybridizes a partial region in the sense strand of the thrombopoietin gene and that can specifically amplify the partial DNA region containing the base at position 5713 of the thrombopoietin gene in concurrent use with the above first or second nucleic acid; and

(11) a set of nucleic acids which consists of a first nucleic acid that specifically hybridizes a partial region containing the base at position 994 in the antisense strand of the platelet-activating factor acetylhydrolase gene whose base at position 994 is G and that is labeled with a first labeling substance, of a second nucleic acid that specifically hybridizes a partial region containing the base at position 994 in the antisense strand of the platelet-activating factor acetylhydrolase gene whose base at position 994 is T and that is labeled with a second labeling substance, and of the third nucleic acid that specifically hybridizes a partial region in the sense strand of the platelet-activating factor acetylhydrolase gene and that can specifically amplify the partial DNA region containing the base at position 994 of the platelet-activating factor acetylhydrolase gene in concurrent use with the above first or second nucleic acid.

In the above mention, kits are constructed by selecting two or more sets of nucleic acids from the group consisting of (7) to (11). However, kits may be constructed by making a group consisting of two or more nucleic acids arbitrarily selected from (7) to (11) and selecting two or more nucleic acids from such a group. For example, kits may be constructed by selecting two or more nucleic acids from the group consisting of (7) to (10) (sets of nucleic acids for analyzing polymorphisms with four highest odds ratios in Example mentioned below), or kits may be constructed by selecting two or more sets of nucleic acids from the group consisting of (7) to (9) (sets of nucleic acids for analyzing polymorphisms with three highest odds ratios in Example mentioned below).

A kit for detecting the genotype comprising two or more sets of nucleic acids selected from the group consisting of the following (12) to (17);

(12) a set of nucleic acids which consists of a first nucleic acid that specifically hybridizes a partial region containing the base corresponding to the base at position 561 in the sense strand of the E-selectin gene whose base at position 561 is A and that is labeled with a first labeling substance, of a second nucleic acid that specifically hybridizes a partial region containing the base corresponding to the base at position 561 in the sense strand of the E-selectin gene whose base at position 561 is C and that is labeled with a second labeling substance, and of the third nucleic acid that specifically hybridizes a partial region in the antisense strand of the E-selectin gene and that can specifically amplify the partial DNA region containing the base at position 561 of the E-selectin gene in concurrent use with the above first or second nucleic acid;

(13) a set of nucleic acids which consists of a first nucleic acid that specifically hybridizes a partial region containing the base at position 2445 in the antisense strand of the fatty acid-binding protein 2 gene whose base at position 2445 is G and that is labeled with a first labeling substance, of a second nucleic acid that specifically hybridizes a partial region containing the base at position 2445 in the antisense strand of the fatty acid-binding protein 2 gene whose base at position 2445 is A and that is labeled with a second labeling substance, and of the third nucleic acid that specifically hybridizes a partial region in the sense strand of the fatty acid-binding protein 2 gene and that can specifically amplify the partial DNA region containing the base at position 2445 of the fatty acid-binding protein 2 gene in concurrent use with the above first or second nucleic acid;

(14) a set of nucleic acids which consists of a first nucleic acid that specifically hybridizes a partial region containing a base corresponding to the base at position 1018 in the antisense strand of the glycoprotein Ibα gene whose base at position 1018 is C and that is labeled with a first labeling substance, of a second nucleic acid that specifically hybridizes a partial region containing a base corresponding to the base at position 1018 in the antisense strand of the glycoprotein Ibα gene whose base at position 1018 is T and that is labeled with a second labeling substance, and of a third nucleic acid that specifically hybridizes a partial region in the sense strand of the glycoprotein Ibα gene and that can specifically amplify the partial DNA region containing the base at position 1018 of the glycoprotein Ibα gene in concurrent use with the above first or second nucleic acid;

(15) a set of nucleic acids which consists of a pair of nucleic acids (first and second nucleic acids) that is designed to specifically amplify the partial region of DNA containing a part of polymorphism at position −668 of the plasminogen activator inhibitor 1 gene, of a third nucleic acid that specifically hybridizes the nucleic acid which is obtained by amplification using plasminogen activator inhibitor 1 gene in which four G successively exist in the 3' direction from the position −668 as a template and the pair of nucleic acids, and of a fourth nucleic acid that specifically hybridizes a nucleic acid which is obtained by amplification using plasminogen activator inhibitor 1 gene in which five G successively exist in the 3' direction from the position −668 as a template and the pair of nucleic acids;

(16) a set of nucleic acids which consists of a first nucleic acid that specifically hybridizes a partial region containing a base corresponding to the base at position 584 in the antisense strand of the paraoxonase gene whose base at position 584 is G and that is labeled with a first labeling substance, of a second nucleic acid that specifically hybridizes a partial region containing a base corresponding to the base at position 584 in the antisense strand of the paraoxonase gene whose base at position 584 is A and that is labeled with a second labeling substance, and of a third nucleic acid that specifically hybridizes a partial region in the sense strand of the paraoxonase gene and that can specifically amplify the partial DNA region containing the base at position 584 of the paraoxonase gene in concurrent use with the above first or second nucleic acid; and

(17) a set of nucleic acids which consists of a first nucleic acid that specifically hybridizes a partial region containing the base corresponding to the base at position 3932 in the antisense strand of the apolipoprotein E gene whose base at position 3932 is T and that is labeled with a first labeling substance, of a second nucleic acid that specifically hybridizes a partial region containing the base corresponding to the base at position 3932 in the antisense strand of the apolipoprotein E gene whose base at position 3932 is C and that is labeled with a second labeling substance, and of the third nucleic acid that specifically hybridizes a partial region in the sense strand of the apolipoprotein E gene and that can specifically amplify the partial DNA region containing the base at position 3932 of the apolipoprotein E gene in concurrent use with the above first or second nucleic acid.

In the above mention, kits are constructed by selecting two or more nucleic acids from the group consisting of (12) to (17). However, kits may be constructed by making a group consisting of two or more nucleic acids arbitrarily selected from (12) to (17) and selecting two or more nucleic acids from such a group. For example, kits may be constructed by selecting two or more nucleic acids from the group consisting of (12) to (16) (sets of nucleic acids for analyzing polymorphisms with five highest odds ratios in Example mentioned below), or kits may be constructed by selecting two or more nucleic acids from the group consisting of (12) to (15) (nucleic acids for analyzing polymorphisms with four highest odds ratios in Example mentioned below).

A kit for detecting the genotype comprising two or more sets of nucleic acids selected from the group consisting of the following (18) to (22);

(18) a set of nucleic acids which consists of a pair of nucleic acids (first and second nucleic acids) that is designed to specifically amplify the partial region of DNA containing a part of polymorphism at position −668 of the plasminogen activator inhibitor 1 gene, of a third nucleic acid that specifically hybridizes the nucleic acid which is obtained by amplification using plasminogen activator inhibitor 1 gene in which four G successively exist in the 3' direction from the position −668 as a template and the pair of nucleic acids, and of a fourth nucleic acid that specifically hybridizes a nucleic acid which is obtained by amplification using plasminogen activator inhibitor 1 gene in which five G successively exist in the 3' direction from the position −668 as a template and the pair of nucleic acids;

(19) a set of nucleic acids which consists of a first nucleic acid that specifically hybridizes a partial region containing a base corresponding to the base at position −482 in the antisense strand of the apolipoprotein C-III gene whose base at position −482 is C and that is labeled with a first labeling substance, of a second nucleic acid that specifically hybridizes a partial region containing a base corresponding to the base at position −482 in the antisense strand of the apolipoprotein C-III gene whose base at position −482 is T and that is labeled with a second labeling substance, and of a third nucleic acid that specifically hybridizes a partial region in the sense strand of the apolipoprotein C-III gene and that can specifically amplify the partial DNA region containing the base at position −482 of the apolipoprotein C-III gene in concurrent use with the above first or second nucleic acid;

(20) a set of nucleic acids which consists of a first nucleic acid that specifically hybridizes a partial region containing a base corresponding to the base at position 584 in the antisense strand of the paraoxonase gene whose base at position 584 is G and that is labeled with a first labeling substance, of a second nucleic acid that specifically hybridizes a partial region containing a base corresponding to the base at position 584 in the antisense strand of the paraoxonase gene whose base at position 584 is A and that is labeled with a second labeling substance, and of a third nucleic acid that specifically hybridizes a partial region in the sense strand of the paraoxonase gene and that can specifically amplify the partial DNA region containing the base at position 584 of the paraoxonase gene in concurrent use with the above first or second nucleic acid;

(21) a set of nucleic acids which consists of a first nucleic acid that specifically hybridizes a partial region containing a base corresponding to the base at position 1018 in the antisense strand of the glycoprotein Ibα gene whose base at position 1018 is C and that is labeled with a first labeling substance, of a second nucleic acid that specifically hybridizes a partial region containing a base corresponding to the base at position 1018 in the antisense strand of the glycoprotein Ibα gene whose base at position 1018 is T and that is labeled with a second labeling substance, and of a third nucleic acid that specifically hybridizes a partial region in the sense strand of the glycoprotein Ibα gene and that can specifically amplify the partial DNA region containing the base at position 1018 of the glycoprotein Ibα gene in concurrent use with the above first or second nucleic acid; and

(22) a set of nucleic acids which consists of a first nucleic acid that specifically hybridizes a partial region containing the base corresponding to the base at position 3932 in the antisense strand of the apolipoprotein E gene whose base at position 3932 is T and that is labeled with a first labeling substance, of a second nucleic acid that specifically hybridizes a partial region containing the base corresponding to the base at position 3932 in the antisense strand of the apolipoprotein E gene whose base at position 3932 is C and that is labeled with a second labeling substance, and of the third nucleic acid that specifically hybridizes a partial region in the sense strand of the apolipoprotein E gene and that can specifically amplify the partial DNA region containing the base at position 3932 of the apolipoprotein E gene in concurrent use with the above first or second nucleic acid.

In the above mention, kits are constructed by selecting two or more nucleic acids from the group consisting of (18) to (22). However, kits may be constructed by making a group consisting of two or more nucleic acids arbitrarily selected from (18) to (22) and selecting two or more nucleic acids from such a group. For example, kits may be constructed by selecting two or more nucleic acids from the group consisting of (18) to (21) (sets of nucleic acids for analyzing polymorphisms with four highest odds ratios in Example mentioned below), or kits may be constructed by selecting two or more nucleic acids from the group consisting of (18) to (20) (nucleic acids for analyzing polymorphisms with three highest odds ratios in Example mentioned below).

In the above-mentioned kits, one or two or more of reagents (buffer, reagent for reaction, and reagent for detection, etc.) may be combined in response to the usage of the kit.

The present invention is hereinafter explained in more detail by way of Examples.

EXAMPLE 1

Selection of Gene Polymorphism

By using several kinds of public databases including PubMed [National Center for Biological Information (NCBI)], Online Mendelian inheritance in Men (NCBI), Single Nucleotide Polymorphism (NCBI), etc., from a comprehensive viewpoint including vascular biology, platelet-leukocyte biology, coagulation-fibrinogenolysis system, and lipid and glucose metabolism, etc., 71 genes which were estimated to be associated with coronary arteriosclerosis, coronary artery spasm, hypertension, diabetes mellitus, hyperlipidemia, etc. were extracted from genes which had been previously reported. Furthermore, among the polymorphisms existing in these genes, 112 polymorphisms including polymorphisms which exist in promoter regions or exons, or polymorphisms which were located in splice donor sites or acceptor sites and expected to be associated with the functional changes of gene products were selected (FIGS. 1 and 2).

EXAMPLE 2

Determination of Gene Polymorphism

Subjects were 1869 Japanese men and women (1313 men and 556 women) who were hospitalized so as to undergo coronary angioplasty (balloon dilatation or stent implantation) between July 1998 and December 2001. The 1390 (910 in men and 480 in women) and 1001 (710 in men and 291 in women) coronary lesions undergone balloon dilatation and stent implantation, respectively, were examined. Follow-up coronary angiography was performed six months after the coronary angioplasty. Coronary restenosis lesions with acute occlusion after balloon dilatation or with subacute stent thrombosis were excluded from the study. Quantitative angiographic measurements were performed on end-diastolic frames. Restenosis was defined as narrowing of 50% or more of the minimal lumen diameter the coronary artery at the site coronary angioplasty was performed.

From each of the subjects, 7 mL of venous blood was collected in a tube containing 50 mmol/L EDTA-2Na and genome DNA was extracted by using a DNA extraction kit (Qiagen, Chatsworth, Calif.). Genotypes of single nucleotide polymorphisms were determined with a fluorescence- or colorimetry-based allele-specific primer-probe assay system (Toyobo Gene Analysis, Tsuruga, Japan) (see FIGS. 3 and 4). DNA fragment containing a polymorphism site was amplified by polymerase chain reaction (PCR) by using two kinds of allele specific sense primers (or antisense primers) whose 5' end were labeled with fluorescein isothiocyanate (FITC) or Texas red (TxR) and an antisense primer (or a sense primer) whose 5' end was labeled with biotin. Alternatively, DNA fragment containing polymorphism site was amplified by PCR by using two kinds of allele specific sense (or antisense) primers and an antisense (or a sense) primer whose 5' end was labeled with biotin, or by using a sense primer and an antisense primer whose 5' end was labeled with biotin. The reaction solution (25 μL) contained 20 ng of DNA, 5 pmol of each primer, 0.2 mmol/L of each deoxynucleoside triphosphate, 1 to 4 mmol/L of $MgCl_2$, 1 U of DNA polymerase (rTaq or KODplus; Toyobo Co., Ltd. Osaka, Japan) in corresponding DNA polymerase buffer. The amplification protocol comprised an initial denaturation at 95° C. for 5 minutes; 35 to 45 cycles of denaturation at 95° C. for 30 seconds, annealing at 55 to 67.5° C. for 30 seconds, extension at 72° C. for 30 seconds, and a final extension at 72° C. for 2 minutes.

For determination of genotype by fluorescence, amplified DNA was incubated with a solution containing streptavidin-conjugated magnetic beads in 96-well plates at room temperature. The plates were placed on a magnetic stand, supernatants were collected from the wells and then transferred to the wells of a 96-well plate containing 0.01 M NaOH, followed by measuring fluorescence by microplate reader at excitation wavelength and emission wavelength of 485 nm and 538 nm for FITC and at excitation wavelength and emission wavelength of 584 nm and 612 nm for TxR. Furthermore, for determination of genotype by colorimetry, amplified DNA was denatured with 0.3 M NaOH and then subjected to hybridization at 37° C. for 30 min in hybridization buffer containing 30 to 45% formamide with any of allele-specific capture probes fixed to the bottom of the wells of a 96-well plate. After thorough washing of the wells, alkaline phosphatase-conjugated streptavidin was added to each well and the plate was shaken at 37° C. for 15 min. The wells were again washed, and, after the addition of a solution containing 0.8 mM 2-(4-iodophenyl)-3-(4-nitrophenyl)-5-(2,4-disulfophenyl)-2H-tetrazolium (monosodium salt) and 0.4 mM 5-bromo-4-chloro-3-indolyl phosphate p-toluidine salt, the absorbance at 450 nm was measured.

To confirm the accuracy of genotyping by this method, DNA samples of 50 people were selected at random, and the samples were subjected to PCR-restriction fragment length analyzing polymorphism method or direct sequencing method of PCR products. In any samples, the genotype determined by the allele specific primer-probe measurement system was identical to that determined by PCR-polymerase chain reaction-restriction fragment length polymorphism method or direct sequencing method.

Note here that statistical analysis in the following association study was carried out as follows. Clinical data were compared between coronary lesions with restenosis and without restenosis by the unpaired Student's t test or the Mann-Whitney U test. Qualitative data were examined by the chi-square test. Allele frequencies were estimated by the gene counting method, and the chi-square test was used to identify departures from Hardy-Weinberg equilibrium. The present inventors performed multivariate logistic regression analysis with adjustment for risk factors, with restenosis as a dependent variable and with age, body mass index (BMI), smoking status (0=nonsmoker, 1=smoker), metabolic variables (0=no history of diabetes mellitus, hypercholesterolemia, or hyperuricemia; 1=positive history) and genotype of each polymorphism as independent variables. Each genotype was assessed according to dominant, recessive, and additive genetic models, and the P value, odds ratio, and 95% confidence interval were calculated. For combined genotype analyses, the present inventors performed the stepwise forward selection method of multivariate logistic regression analysis to calculate odds ratios for each combined genotype.

EXAMPLE 3

Selection of Polymorphism Associated with Restenosis After Coronary Angioplasty and Development of Method for Diagnosing Restenosis After Coronary Angioplasty The present inventors performed an association study of the 112 polymorphisms of the 71 candidate genes with myocardial infarction in 451 men (myocardial infarction: 219, control: 232) and in 458 women (myocardial infarction: 226, control: 232) in the previous report (Yamada Y, Izawa H, Ichihara S, et al. Genetic risk diagnosis system for myocardial infarction developed by a large scale association study of 112 gene polymorphisms in 5061 individuals (in press)). In this study, the present inventors have found that 19 and 18 single nucleotide polymorphisms were associated with the development of myocardial infarction in men and women, respectively, which included candidate genes of restenosis after coronary angioplasty (see FIGS. 1, 2 and 5). In this Example, a large scale association study on the association of these single nucleotide polymorphisms with restenosis after balloon dilatation or in-stent restenosis was carried out in total 2391 coronary lesions.

FIGS. 6 and 7 show background data of all of the examined 2391 coronary lesions (1620 for men, 771 for women). For men, the prevalence of hypertension and diabetes mellitus was significantly greater, and age was significantly smaller, in coronary lesions with restenosis after balloon angioplasty than in those without restenosis; and the prevalence of smoking, diabetes mellitus and hyperuricamia was significantly greater, and age was significantly smaller, in coronary lesions with restenosis after stent implantation than in those without restenosis (FIG. 6). For women, age and the prevalence of smoking and diabetes mellitus were significantly greater in coronary lesions with restenosis after balloon angioplasty than in those without restenosis; and age and the prevalence of diabetes mellitus were significantly greater, and the prevalence of smoking, hypertension and hyperuricemia was significantly smaller in coronary lesions with restenosis after stent implantation than in those without restenosis (FIG. 7). Also, for women, a prevalence of right coronary artery was significantly higher, and that of left circumflex artery was significantly lower, among coronary lesions with restenosis after balloon angioplasty than among those without restenosis; and the prevalence of left anterior descendent artery was significantly higher among coronary lesions with restenosis after stent implantation than among those without restenosis (FIG. 7).

In the association study of restenosis after coronary angioplasty with 19 polymorphisms for men and 18 polymorphisms for women, multivariate logistic regression analysis with adjustment for age, BMI, and the prevalence of smoking, hypertension, diabetes mellitus, hypercholesterolemia and hyperuricemia revealed that six and five polymorphisms were associated significantly with restenosis after balloon dilatation and stent implantation, respectively ($P<0.05$ in either a dominant or recessive genetic model) (FIG. 8 shows the data for men and FIG. 9 shows the data for women).

The present inventors performed the stepwise forward selection method of multivariate logistic regression analysis (FIGS. 10 and 11). In this method, either a dominant or recessive model was used based on the P values (lower P values) for association of each polymorphism with restenosis after coronary angioplasty shown in FIGS. 8 and 9. The chromosomal loci of these genes are also shown in FIGS. 10 and 11. Although the loci of the tumor necrosis factor-α gene and the platelet-activating factor acetylhydrolase gene are located near each other, no association in distribution between the both polymorphisms was observed. Similarly, in spite of the proximity of the plasminogen activator inhibitor-1 gene and the paraoxonase gene, no association in distribution between the both polymorphisms was observed. Odds ratios restenosis after balloon dilatation or stent implantation based on combined genotypes with the stepwise forward selection method is shown in FIGS. 12, 13 and 16A for men and in FIGS. 14, 15 and 16B for women. For men, combined genotype analysis of five polymorphisms (ApoE (3932T→C) polymorphism, GPIa (1648A→G) polymorphism, TNFα (−863C→A) polymorphism, G-protein β3 (825C→T) polymorphism and ApoC-III (−482C→T) polymorphism) revealed that the maximal odds ratio for restenosis after balloon dilatation was 10.55 (FIGS. 12 and 16A). Further combination with the remaining polymorphism (AGT (−6G→A) polymorphism) for a total of six polymorphisms, revealed that the maximal odds ratio for restenosis after balloon dilatation was 15.09 (FIG. 16A). Also, among men, combined genotype analysis of five polymorphisms (TSP4 (1186G→C) polymorphism, TNFα (−863C→A) polymorphism, TM (2136C→T) polymorphism, TPO (5713A→G) polymorphism and PAF-AH (994G→T) polymorphism) revealed that the maximal odds ratio for in-stent restenosis was 6.64 (FIGS. 13 and 16A). For women, combined genotype analysis of five polymorphisms (E selectin (561A→C) polymorphism, FABP2 (2445G→A) polymorphism, GPIbα (1018C→T) polymorphism, PAI1 (−668/4G→5G) polymorphism and PON (584G→A) polymorphism) revealed that the maximal odds ratio for restenosis after balloon dilatation was 37.43 (FIGS. 14 and 16B). Further combination with the remaining polymorphism (ApoE (3932T→C) polymorphism) for a total of six polymorphisms, revealed that the maximal odds ratio for restenosis after balloon dilatation was 44.54 (FIG. 16B). Also, among women, combined genotype analysis of five polymorphisms (PAI1 (−668/4G→5G) polymorphism, ApoC-III (−482C→T) polymorphism, PON (584G→A) polymorphism, GPIbα (1018C→T) polymorphism and ApoE (3932T→C) polymorphism), revealed that the maximal odds ratio for in-stent restenosis was 117.83 (FIGS. 15 and 16B).

As mentioned above, according to the multivariate logistic regression analysis, for men and women, six single nucleotide polymorphisms are associated with restenosis after balloon dilatation and five single nucleotide polymorphisms are associated with in-stent restenosis. That is to say, the present inventors have examined the association of restenosis after coronary angioplasty with 19 single nucleotide polymorphisms for men and 18 single nucleotide polymorphisms for women, and shown that six and five single nucleotide polymorphisms were associated with restenosis after balloon dilatation and in-stent stent restenosis, respectively, in men and women, by a large-scale association study with 2391 coronary lesions. Furthermore, the present inventors developed a genetic risk diagnosis system for restenosis that yielded maximal odds ratios of 15.09 and 44.54 for restenosis after balloon dilatation, and of 6.64 and 117.83 for in-stent restenosis in men and women, respectively, on the basis of the stepwise forward selection method of multivariate logistic regression analysis.

The major cause of restenosis after balloon dilatation is chronic remodeling of coronary arteries and that of in-stent restenosis is neointimal hyperplasia (Mintz G S, Popma J J, Pichard A D, et al. Arterial remodeling after coronary angioplasty: a serial intravascular ultrasound study. Circulation 1996;94:35-43.; Hoffmann R, Mintz G S, Dussaillant G R, et al. Patterns and mechanisms of in-stent restenosis. A serial intravascular ultrasound study. Circulation 1996;94:1247-54). The present inventors thus examined the association between 19 single nucleotide polymorphisms for men and 18 single nucleotide polymorphisms for women and restenosis after coronary angioplasty on the basis of a comprehensive overview of vascular biology, platelet and leukocyte biology, fibrinolysis system, as well as lipid and glucose metabolism and other metabolic factors. Indeed, genes associated with restenosis played roles in diverse aspects of the etiology of this condition. The genes associated with restenosis after balloon dilatation played roles in vascular biology (G-protein β3 subunit and E-selectin) and inflammation (tumor necrosis factor-α), hypertension (angiotensinogen), lipid metabolism (apolipoproteins E and C-III, fatty acid-binding protein 2 and paraoxonase), platelet function (glycoprotein Ia and glycoprotein Ibα), and fibrinolysis (plasminogen activator inhibitor-1), etc. Also, genes associated with in-stent restenosis played roles in vascular biology (thrombospondin 4) and inflammation (tumor necrosis factor-α and platelet-activating factor acetylhydrolase), lipid metabolism (apolipoproteins E and C-III and paraoxonase), platelet function (thrombomodulin, thrombopoietin and glycoprotein Ibα), and fibrinolysis (plasminogen activator inhibitor-1), etc. One polymorphism (tumor necrosis factor-α gene) was associated with both restenosis after balloon dilatation and in-stent restenosis in men, and four polymorphisms (plasminogen activator inhibitor-1 gene, paraoxonase, glycoprotein Ibα and apolipoproteins E genes) in women. The maximal odds ratios of restenosis after coronary angioplasty (in restenosis after balloon dilatation, 15.09 for men and 44.54 for women; and in in-stent restenosis, 6.64 for men and 117.83 for women) obtained with our genetic risk diagnosis system were the highest among such values previously reported by association studies of restenosis.

Among 15 polymorphisms associated with restenosis after coronary angioplasty, the polymorphisms of apolipoprotein E (van Bockxmeer F M, Mamotte C D S, Gibbons F R, Taylor R R. Apolipoprotein e4 homozygosity-a determinant of restenosis after coronary angioplasty. Atherosclerosis 1994; 110:195-202.), angiotensinogen (Volzke H, Hertwig S, Rettig R, Motz W. The angiotensinogen gene 235T variant is associated with an increased risk of restenosis after percutaneous transluminal coronary angioplasty. Clin Sci 2000;99:19-25), plasminogen activator inhibitor-1 (Ortlepp J R, Hoffmann R, Killian A, Lauscher J, Merkelbach-Brese S, Hanrath P. The 4G/5G promoter polymorphism of the plasminogen activator inhibitor-1 gene and late luminal loss after coronary stent placement in smoking and nonsmoking patients. Clin Cardiol 2001; 24: 585-591), and E-selectin (Rauchhaus M, Gross M, Schulz S, et al. The E-selectin SER123ARG gene polymorphism and restenosis after successful coronary angioplasty. Int J Cardiol 2002;83:249-257) were previously shown to be associated with restenosis. In contrast to our results, restenosis was not associated with the polymorphisms of the glycoprotein Ia gene (von Beckerath N, Koch W, Mehilli J, et al. Glycoprotein Ia C807T polymorphism and risk of restenosis following coronary stenting. Atherosclerosis 2001;156:463-468) or G-protein β3 subunit gene (von Beckerath N, Kastrati A, Koch W, et al. G protein β3 subunit polymorphism and risk of thrombosis and restenosis following coronary stent placement. Atherosclerosis 2000; 149: 151-155), although these genes may be important in the etiology of restenosis (Matsuno H, Kozawa O, Niwa M, Uematsu T. Inhibition of von Willebrand factor binding to platelet GP Ib by a fractionated aurintricarboxylic acid prevents restenosis after vascular injury in hamster carotid artery. Circulation 1997;96:1299-304.; Iaccarino G. Smithwick L A, Lefkowitz R J, Koch W J. Targeting Gβγsignaling in arterial vascular smooth muscle proliferation: a novel atrategy to limit restenosis. Proc Natl Acad Sci USA 1999;96:3945-50.). Other nine polymorphisms have not been examined on association with restenosis after coronary angioplasty. Among them, tumor necrosis factor-α (Clausell N, de Lima V C, Molossi S, et al. Expression of tumor necrosis factor α and accumulation of fibronectin in coronary artery restenotic lesions retrieved by atherectomy. Br Heart J 1995, 73:534-9) and glycoprotein Ibα (Gawaz M, Neumann F J, Ott I, May A, Rudiger S, Schomig A. Changes in membrane glycoproteins of circulating platelets after coronary stent implantation. Heart 1996; 76: 166-72.) are thought to have roles in the development of this condition.

It is possible that some of the polymorphisms examined in the Example are in linkage disequilibrium with polymorphisms of other nearby genes that are actually responsible for the development of restenosis after coronary angioplasty. The results by the present inventors indicate, however, that ten and seven genes are susceptibility loci for restenosis after coronary angioplasty in Japanese men and women, respectively, and that the corresponding combined genotypes may be useful for the diagnosis of genetic risk for restenosis after balloon dilatation or in-stent restenosis. It is thought that the genetic risk diagnosis system of the present invention will contribute to the prediction of restenosis after coronary angioplasty and provide information on the selection of the most appropriate treatment, and thereby quality of life for individuals with coronary artery disease is improved as well as medical expenses is reduced.

The present invention is not limited to the description of the above embodiments. A variety of modifications, which are within the scopes of the following claims and which are achieved easily by a person skilled in the art, are included in the present invention.

INDUSTRIAL APPLICABILITY

According to the present invention, gene polymorphism associated with restenosis after coronary angioplasty is analyzed and the genotype of nucleic acid sample is detected. By using the information about polymorphism obtained by the detection of the genotype, diagnosis of the risk of restenosis after coronary angioplasty with high accuracy and high predictability can be carried out. That is to say, the present invention provides an effective means for understanding in advance the risk of development of restenosis after a certain coronary angioplasty. Therefore, the present invention provides information useful for selecting an appropriate treatment method and enables an appropriate treatment method to be selected. Thus, high effect of treatment can be realized and the quality of life of patients with coronary artery disease can be improved. In addition, it is possible to solve the problem such as an increase in medical expenses because of the repetition of inappropriate treatments, thus contributing much to the medical economy. On the other hand, the present invention provides information useful in clarifying the development mechanism of restenosis, so that it provides an extremely important means for establishing prevention method of restenosis.

The invention claimed is:

1. A method for determining an increased risk of restenosis after coronary angioplasty in a human male subject, said method comprising:

(i) obtaining a biological sample from said human male subject, said biological sample comprising nucleic acids from said human male subject;

(ii) detecting in said nucleic acids: a C at position 3932 of SEQ ID NO: 1 in at least one allele of the apolipoprotein E gene; an A at position 197 of SEQ ID NO: 3 in at least one allele of the tumor necrosis factor-α gene; and a T at position 831 of SEQ ID NO: 4 in both alleles of the G-protein β3 subunit gene; and (iii) correlating a C at position 3932 of SEQ ID NO: 1 in at least one allele of the apolipoprotein E gene, an A at position 197 of SEQ ID NO: 3 in at least one allele of the tumor necrosis factor-α gene, and a T at position 831 of SEQ ID NO: 4 in both alleles of the G-protein β3 subunit gene in said nucleic acids with an increased risk of restenosis after coronary angioplasty in said human male subject.

* * * * *

```
                        SEQUENCE LISTING

<160> NUMBER OF SEQ ID NOS: 67

<210> SEQ ID NO 1
<211> LENGTH: 5515
<212> TYPE: DNA
<213> ORGANISM: Homo sapiens

<400> SEQUENCE: 1

ggaacttgat gctcagagag gacaagtcat ttgcccaagg tcacacagct ggcaactggc     60

agacgagatt cacgccctgg caatttgact ccagaatcct aaccttaacc cagaagcacg    120

gcttcaagcc ctggaaacca caatacctgt ggcagccagg gggaggtgct ggaatctcat    180

ttcacatgtg gggagggggc tcctgtgctc aaggtcacaa ccaaagagga agctgtgatt    240

aaaacccagg tcccatttgc aaagcctcga cttttagcag gtgcatcata ctgttcccac    300

ccctcccatc ccacttctgt ccagccgcct agccccactt tctttttttt ctttttttga    360

gacagtctcc ctcttgctga ggctggagtg cagtggcgag atctcggctc actgtaacct    420

ccgcctcccg ggttcaagcg attctcctgc ctcagcctcc caagtagcta ggattacagg    480

cgcccgccac cacgcctggc taacttttgt atttttagta gagatggggt ttcaccatgt    540
```

-continued

```
tggccaggct ggtctcaaac tcctgacctt aagtgattcg cccactgtgg cctcccaaag    600
tgctgggatt acaggcgtga gctaccgccc ccagcccctc ccatcccact tctgtccagc    660
cccctagccc tactttcttt ctgggatcca ggagtccaga tccccagccc cctctccaga    720
ttacattcat ccaggcacag gaaaggacag ggtcaggaaa ggaggactct gggcggcagc    780
ctccacattc cccttccacg cttggccccc agaatggagg agggtgtctg tattactggg    840
cgaggtgtcc tcccttcctg gggactgtgg ggggtggtca aaagacctct atgccccacc    900
tccttcctcc ctctgccctg ctgtgcctgg ggcaggggga gaacagccca cctcgtgact    960
gggctgccca gcccgcccta tccctggggg agggggcggg acagggggag ccctataatt   1020
ggacaagtct gggatccttg agtcctactc agccccagcg gaggtgaagg acgtccttcc   1080
ccaggagccg gtgagaagcg cagtcggggg cacggggatg agctcagggg cctctagaaa   1140
gagctgggac cctgggaagc cctggcctcc aggtagtctc aggagagcta ctcggggtcg   1200
ggcttgggga gaggaggagc gggggtgagg caagcagcag gggactggac ctgggaaggg   1260
ctgggcagca gagacgaccc gacccgctag aaggtggggt ggggagagca gctggactgg   1320
gatgtaagcc atagcaggac tccacgagtt gtcactatca ttatcgagca cctactgggt   1380
gtccccagtg tcctcagatc tccataactg gggagccagg ggcagcgaca cggtagctag   1440
ccgtcgattg gagaacttta aaatgaggac tgaattagct cataaatgga acacggcgct   1500
taactgtgag gttggagctt agaatgtgaa gggagaatga ggaatgcgag actgggactg   1560
agatggaacc ggcggtgggg agggggtggg gggatggaat ttgaaccccg ggagaggaag   1620
atggaatttt ctatggaggc cgacctgggg atggggagat aagagaagac caggagggag   1680
ttaaataggg aatgggttgg gggcggcttg gtaaatgtgc tgggattagg ctgttgcaga   1740
taatgcaaca aggcttggaa ggctaacctg gggtgaggcc gggttggggg cgctgggggt   1800
gggaggagtc ctcactggcg gttgattgac agtttctcct tccccagact ggccaatcac   1860
aggcaggaag atgaaggttc tgtgggctgc gttgctggtc acattcctgg caggtatggg   1920
ggcggggctt gctcggttcc ccccgctcct ccccctctca tcctcacctc aacctcctgg   1980
ccccattcag acagaccctg ggccccctct tctgaggctt ctgtgctgct tcctggctct   2040
gaacagcgat ttgacgctct ctgggcctcg gtttccccca tccttgagat aggagttaga   2100
agttgttttg ttgttgttgt ttgttgttgt tgttttgttt ttttgagatg aagtctcgct   2160
ctgtcgccca ggctggagtg cagtggcggg atctcggctc actgcaagct ccgcctccca   2220
ggtccacgcc attctcctgc ctcagcctcc caagtagctg ggactacagg cacatgccac   2280
cacacccgac taactttttt gtattttcag tagagacggg gtttcaccat gttggccagg   2340
ctggtctgga actcctgacc tcaggtgatc tgcccgtttc gatctcccaa agtgctggga   2400
ttacaggcgt gagccaccgc acctggctgg gagttagagg tttctaatgc attgcaggca   2460
gatagtgaat accagacacg ggcagctgt gatctttatt ctccatcacc cccacacagc   2520
cctgcctggg gcacacaagg acactcaata catgcttttc cgctgggccg gtggctcacc   2580
cctgtaatcc cagcactttg ggaggccaag gtgggaggat cacttgagcc caggagttca   2640
acaccagcct gggcaacata gtgagaccct gtctctacta aaaatacaaa aattagccag   2700
gcatggtgcc acacacctgt gctctcagct actcaggagg ctgaggcagg aggatcgctt   2760
gagcccagaa ggtcaaggtt gcagtgaacc atgttcaggc cgctgcactc cagcctgggt   2820
gacagagcaa gaccctgttt ataaatacat aatgctttcc aagtgattaa accgactccc   2880
ccctcaccct gcccaccatg gctccaaaga agcatttgtg gagcaccttc tgtgtgcccc   2940
```

-continued

```
taggtagcta gatgcctgga cggggtcaga aggaccctga cccgaccttg aacttgttcc   3000
acacaggatg ccaggccaag gtggagcaag cggtggagac agagccggag cccgagctgc   3060
gccagcagac cgagtggcag agcggccagc gctgggaact ggcactgggt cgcttttggg   3120
attacctgcg ctgggtgcag acactgtctg agcaggtgca ggaggagctg ctcagctccc   3180
aggtcaccca ggaactgagg tgagtgtccc catcctggcc cttgaccctc ctggtgggcg   3240
gctatacctc cccaggtcca ggtttcattc tgcccctgtc gctaagtctt ggggggcctg   3300
ggtctctgct ggttctagct tcctcttccc atttctgact cctggcttta gctctctgga   3360
attctctctc tcagctttgt ctctctctct tcccttctga ctcagtctct cacactcgtc   3420
ctggctctgt ctctgtcctt ccctagctct tttatataga gacagagaga tggggtctca   3480
ctgtgttgcc caggctggtc ttgaacttct gggctcaagc gatcctcccg cctcggcctc   3540
ccaaagtgct gggattagag gcatgagcac cttgcccggc ctcctagctc cttcttcgtc   3600
tctgcctctg ccctctgcat ctgctctctg catctgtctc tgtctccttc tctcggcctc   3660
tgccccgttc cttctctccc tcttgggtct ctctggctca tccccatctc gcccgcccca   3720
tcccagccct tctcccccgc ctccccactg tgcgacaccc tcccgccctc tcggccgcag   3780
ggcgctgatg gacgagacca tgaaggagtt gaaggcctac aaatcggaac tggaggaaca   3840
actgaccccg gtggcggagg agacgcgggc acggctgtcc aaggagctgc aggcggcgca   3900
ggcccggctg ggcgcggaca tggaggacgt gcgcggccgc ctggtgcagt accgcggcga   3960
ggtgcaggcc atgctcggcc agagcaccga ggagctgcgg gtgcgcctcg cctcccacct   4020
gcgcaagctg cgtaagcggc tcctccgcga tgccgatgac ctgcagaagc gcctggcagt   4080
gtaccaggcc ggggcccgcg agggcgccga gcgcggcctc agcgccatcc gcgagcgcct   4140
ggggcccctg gtggaacagg gccgcgtgcg ggccgccact gtgggctccc tggccggcca   4200
gccgctacag gagcgggccc aggcctgggg cgagcggctg cgcgcgcgga tggaggagat   4260
gggcagccgg acccgcgacc gcctggacga ggtgaaggag caggtggcgg aggtgcgcgc   4320
caagctggag gagcaggccc agcagatacg cctgcaggcc gaggccttcc aggcccgcct   4380
caagagctgg ttcgagcccc tggtggaaga catgcagcgc cagtgggccg ggctggtgga   4440
gaaggtgcag gctgccgtgg gcaccagcgc cgcccctgtg cccagcgaca atcactgaac   4500
gccgaagcct gcagccatgc gaccccacgc caccccgtgc ctcctgcctc cgcgcagcct   4560
gcagcgggag accctgtccc cgccccagcc gtcctcctgg ggtggaccct agtttaataa   4620
agattcacca agtttcacgc atctgctggc ctccccctgt gatttcctct aagccccagc   4680
ctcagtttct ctttctgccc acatactgcc acacaattct cagccccctc ctctccatct   4740
gtgtctgtgt gtatctttct ctctgccctt tttttttttt tagacggagt ctggctctgt   4800
cacccaggct agagtgcagt ggcacgatct tggctcactg caacctctgc ctcttgggtt   4860
caagcgattc tgctgcctca gtagctggga ttacaggctc acaccaccac acccggctaa   4920
tttttgtatt tttagtagag acgagctttc accatgttgg ccaggcaggt ctcaaactcc   4980
tgaccaagtg atccacccgc cggcctccca aagtgctgag attacaggcc tgagccacca   5040
tgcccggcct ctgcccctct ttcttttttta gggggcaggg aaaggtctca ccctgtcacc   5100
cgccatcaca gctcactgca gcctccacct cctggactca agtgataagt gatcctcccg   5160
cctcagcctt tccagtagct gagactacag gcgcatacca ctaggattaa tttggggggg   5220
ggtggtgtgt gtggagatgg ggtctggctt tgttggccag gctgatgtgg aattcctggg   5280
ctcaagcgat actcccacct tggcctcctg agtagctgag actactggct agcaccacca   5340
```

-continued

```
cacccagctt tttattatta tttgtagaga caaggtctca atatgttgcc caggctagtc   5400

tcaaacccct ggctcaagag atcctccgcc atcggcctcc caaagtgctg ggattccagg   5460

catgggctcc gagcggcctg cccaacttaa taatattgtt cctagagttg cactc        5515


<210> SEQ ID NO 2
<211> LENGTH: 5373
<212> TYPE: DNA
<213> ORGANISM: Homo sapiens

<400> SEQUENCE: 2

gaattcctgc aaacccagcg caactacggt cccccggtca gacccaggat ggggccagaa     60

cggacagggg ccgcgccgct gccgctgctg ctggtgttag cgctcagtca aggcatttta    120

aattgttgtt tggcctacaa tgttggtctc ccagaagcaa aaatattttc cggtccttca    180

agtgaacagt ttgggtatgc agtgcagcag tttataaatc caaaaggcaa ctggttactg    240

gttggttcac cctggagtgg ctttcctgag aaccgaatgg gagatgtgta taaatgtcct    300

gttgacctat ccactgccac atgtgaaaaa ctaaatttgc aaacttcaac aagcattcca    360

aatgttactg agatgaaaac caacatgagc ctcggcttga tcctcaccag gaacatggga    420

actggaggtt ttctcacatg tggtcctctg tgggcacagc aatgtgggaa tcagtattac    480

acaacgggtg tgtgttctga catcagtcct gattttcagc tctcagccag cttctcacct    540

gcaactcagc cctgcccttc cctcatagat gttgtggttg tgtgtgatga atcaaatagt    600

atttatcctt gggatgcagt aaagaatttt ttggaaaaat ttgtacaagg ccttgatata    660

ggccccacaa agacacaggt ggggttaatt cagtatgcca ataatccaag agttgtgttt    720

aacttgaaca catataaaac caaagaagaa atgattgtag caacatccca gacatcccaa    780

tatggtgggg acctcacaaa cacattcgga gcaattcaat atgcaagaaa atatgcctat    840

tcagcagctt ctggtgggcg acgaagtgct acgaaagtaa tggtagttgt aactgacggt    900

gaatcacatg atggttcaat gttgaaagct gtgattgatc aatgcaacca tgacaatata    960

ctgaggtttg gcatagcagt tcttgggtac ttaaacagaa acgcccttga tactaaaaat   1020

ttaataaaag aaataaaagc gatcgctagt attccaacag aaagatactt tttcaatgtg   1080

tctgatgaag cagctctact agaaaaggct gggacattag gagaacaaat tttcagcatt   1140

gaaggtactg ttcaaggagg agacaacttt cagatggaaa tgtcacaagt gggattcagt   1200

gcagattact cttctcaaaa tgatattctg atgctgggtg cagtgggagc ttttggctgg   1260

agtgggacca ttgtccagaa gacatctcat ggccatttga tctttcctaa acaagccttt   1320

gaccaaattc tgcaggacag aaatcacagt tcatatttag gttactctgt ggctgcaatt   1380

tctactggag aaagcactca ctttgttgct ggtgctcctc gggcaaatta taccggccag   1440

atagtgctat atagtgtgaa tgagaatggc aatatcacgg ttattcaggc tcaccgaggt   1500

gaccagattg gctcctattt tggtagtgtg ctgtgttcag ttgatgtgga taaagacacc   1560

attacagacg tgctcttggt aggtgcacca atgtacatga gtgacctaaa gaaagaggaa   1620

ggaagagtct acctgtttac tatcaaaaag ggcattttgg gtcagcacca atttcttgaa   1680

ggccccgagg gcattgaaaa cactcgattt ggttcagcaa ttgcagctct ttcagacatc   1740

aacatggatg gctttaatga tgtgattgtt ggttcaccac tagaaaatca gaattctgga   1800

gctgtataca tttacaatgg tcatcagggc actatccgca caaagtattc ccagaaaatc   1860

ttgggatccg atggagcctt taggagccat ctccagtact ttgggaggtc cttggatggc   1920

tatggagatt taaatgggga ttccatcacc gatgtgtcta ttggtgcctt tggacaagtg   1980
```

-continued

```
gttcaactct ggtcacaaag tattgctgat gtagctatag aagcttcatt cacaccagaa   2040
aaaatcactt tggtcaacaa gaatgctcag ataattctca aactctgctt cagtgcaaag   2100
ttcagaccta ctaagcaaaa caatcaagtg gccattgtat ataacatcac acttgatgca   2160
gatggatttt catccagagt aacctccagg gggttattta aagaaaacaa tgaaaggtgc   2220
ctgcagaaga atatggtagt aaatcaagca cagagttgcc ccgagcacat catttatata   2280
caggagccct ctgatgttgt caactctttg gatttgcgtg tggacatcag tctggaaaac   2340
cctggcacta gccctgccct tgaagcctat tctgagactg ccaaggtctt cagtattcct   2400
ttccacaaag actgtggtga ggatggactt tgcatttctg atctagtcct agatgtccga   2460
caaataccag ctgctcaaga acaacccttt attgtcagca accaaaacaa aaggttaaca   2520
ttttcagtaa cactgaaaaa taaaagggaa agtgcataca acactggaat tgttgttgat   2580
ttttcagaaa acttgttttt tgcatcattc tccctaccgg ttgatgggac agaagtaaca   2640
tgccaggtgg ctgcatctca gaagtctgtt gcctgcgatg taggctaccc tgctttaaag   2700
agagaacaac aggtgacttt tactattaac tttgacttca atcttcaaaa ccttcagaat   2760
caggcgtctc tcagtttcca agccttaagt gaaagccaag aagaaaacaa ggctgataat   2820
ttggtcaacc tcaaaattcc tctcctgtat gatgctgaaa ttcacttaac aagatctacc   2880
aacataaatt tttatgaaat ctcttcggat gggaatgttc cttcaatcgt gcacagtttt   2940
gaagatgttg gtccaaaatt catcttctcc ctgaaggtaa caacaggaag tgttccagta   3000
agcatggcaa ctgtaatcat ccacatccct cagtatacca aagaaaagaa cccactgatg   3060
tacctaactg gggtgcaaac agacaaggct ggtgacatca gttgtaatgc agatatcaat   3120
ccactgaaaa taggacaaac atcttcttct gtatctttca aaagtgaaaa tttcaggcac   3180
accaaagaat tgaactgcag aactgcttcc tgtagtaatg ttacctgctg gttgaaagac   3240
gttcacatga aaggagaata ctttgttaat gtgactacca gaatttggaa cgggactttc   3300
gcatcatcaa cgttccagac agtacagcta acggcagctg cagaaatcaa cacctataac   3360
cctgagatat atgtgattga agataacact gttacgattc ccctgatgat aatgaaacct   3420
gatgagaaag ccgaagtacc aacaggagtt ataataggaa gtataattgc tggaatcctt   3480
ttgctgttag ctctggttgc aattttatgg aagctcggct tcttcaaaag aaaatatgaa   3540
aagatgacca aaaatccaga tgagattgat gagaccacag agctcagtag ctgaaccagc   3600
agacctacct gcagtgggaa ccggcagcat cccagccagg gtttgctgtt tgcgtgcatg   3660
gatttctttt taaatcccat attttttta tcatgtcgta ggtaaactaa cctggtattt   3720
taagagaaaa ctgcaggtca gtttggatga agaaattgtg gggggtgggg gaggtgcggg   3780
gggcaggtag ggaaataata gggaaaatac ctattttata tgatgggga aaaaaagtaa   3840
tctttaaact ggctggccca gagtttacat tctaatttgc attgtgtcag aaacatgaaa   3900
tgcttccaag catgacaact tttaaagaaa aatatgatac tctcagattt taaggggga   3960
aactgttctc tttaaaatat ttgtctttaa acagcaacta cagaagtgga agtgcttgat   4020
atgtaagtac ttccacttgt gtatatttta atgaatattg atgttaacaa gaggggaaaa   4080
caaaacacag gtttttcaa tttatgctgc tcatccaaag ttgccacaga tgatacttcc   4140
aagtgataat tttatttata aactaggtaa aatttgttgt tggttccttt tataccacgg   4200
ctgcccttc cacaccccat cttgctctaa tgatcaaaac atgcttgaat aactgagctt   4260
agagtatacc tcctatatgt ccatttaagt taggagaggg ggcgatatag agactaaggc   4320
acaaaatttt gtttaaaact cagaatataa catttatgta aaatcccatc tgctagaagc   4380
```

-continued

```
ccatcctgtg ccagaggaag gaaaaggagg aaatttcctt tctcttttag gaggcacaac   4440

agttctcttc taggatttgt ttggctgact ggcagtaacc tagtgaattt ttgaaagatg   4500

agtaatttct ttggcaacct tcctcctccc ttactgaacc actctcccac ctcctggtgg   4560

taccattatt atagaagccc tctacagcct gactttctct ccagcggtcc aaagttatcc   4620

cctcctttac ccctcatcca aagttcccac tccttcagga cagctgctgt gcattagata   4680

ttagggggga aagtcatctg tttaatttac acacttgcat gaattactgt atataaactc   4740

cttaacttca gggagctatt ttcatttagt gctaaacaag taagaaaaat aagctagagt   4800

gaatttctaa atgttggaat gttatgggat gtaaacaatg taaagtaaaa cactctcagg   4860

atttcaccag aagttacaga tgaggcactg gaaaccacca ccaaattagc aggtgcacct   4920

tctgtggctg tcttgtttct gaagtacttt ttcttccaca agagtgaatt tgacctaggc   4980

aagtttgttc aaaaggtaga tcctgagatg atttggtcag attgggataa ggcccagcaa   5040

tctgcatttt aacaagcacc ccagtcacta ggatgcagat ggaccacact ttgagaaaca   5100

ccacccattt ctacttttg caccttattt tctctgttcc tgagccccca cattctctag   5160

gagaaactta gattaaaatt cacagacact acatatctaa agctttgaca agtccttgac   5220

ctctataaac ttcagagtcc tcattataaa atgggaagac tgagctggag ttcagcagtg   5280

atgcttttta gttttaaaag tctatgatct gatctggact tcctataata caaatacaca   5340

atcctccaag aatttgactt ggaaaaggaa ttc                                5373
```

```
<210> SEQ ID NO 3
<211> LENGTH: 1178
<212> TYPE: DNA
<213> ORGANISM: Homo sapiens
<220> FEATURE:
<221> NAME/KEY: misc_feature
<222> LOCATION: (881)..(881)
<223> OTHER INFORMATION: n stands for any base

<400> SEQUENCE: 3

ggggaagcaa aggagaagct gagaagatga aggaaaagtc agggtctgga ggggcggggg     60

tcagggagct cctgggagat atggccacat gtagcggctc tgaggaatgg gttacaggag    120

acctctgggg agatgtgacc acagcaatgg gtaggagaat gtccagggct atggaagtcg    180

agtatcgggg acccccccctt aacgaagaca gggccatgta gagggcccca gggagtgaaa    240

gagcctccag gacctccagg tatggaatac aggggacgtt taagaagata tggccacaca    300

ctggggccct gagaagtgag agcttcatga aaaaaatcag ggaccccaga gttccttgga    360

agccaagact gaaaccagca ttatgagtct ccgggtcaga atgaaagaag aaggcctgcc    420

ccagtggtct gtgaattccc gggggtgatt tcactccccg ggctgtccca ggcttgtccc    480

tgctaccccc acccagcctt tcctgaggcc tcaagctgcc accaagcccc cagctccttc    540

tccccgcaga cccaaacaca ggcctcagga ctcaacacag cttttccctc caaccccgtt    600

ttctctccct caaggactca gctttctgaa gcccctccca gttctagttc tatctttttc    660

ctgcatcctg tctggaagtt agaaggaaac agaccacaga cctggtcccc aaaagaaatg    720

gaggcaatag gttttgaggg gcatggggac ggggttcagc ctccagggtc ctacacacaa    780

atcagtcagt ggcccagaag acccccctcg gaatcggagc agggaggatg gggagtgtga    840

ggggtatcct tgatgcttgt gtgtccccaa ctttccaaat ncccgccccc gcgatggaga    900

agaaaccgag acagaaggtg cagggcccac taccgcttcc tccagatgag cttatgggtt    960

tctccaccaa ggaagttttc cgctggttga atgattcttt ccccgccctc ctctcgcccc   1020
```

-continued

```
agggacatat aaaggcagtt gttggcacac ccagccagca gacgctccct cagcaaggac   1080

agcagaggac cagctaagag ggagagaagc aactgcagac ccccctgaa aacaaccctc   1140

agacgccaca tcccctgaca agctgccagg caggttct                           1178
```

<210> SEQ ID NO 4
<211> LENGTH: 1523
<212> TYPE: DNA
<213> ORGANISM: Homo sapiens

<400> SEQUENCE: 4

```
gggtcgatgg gggagatgga gcaactgcgt caggaagcgg agcagctcaa gaagcagatt     60

gcagatgcca ggaaagcctg tgctgacgtt actctggcag agctggtgtc tggcctagag    120

gtggtgggac gagtccagat gcggacgcgg cggacgttaa ggggacacct ggccaagatt    180

tacgccatgc actgggccac tgattctaag ctgctggtaa gtgcctcgca agatgggaag    240

ctgatcgtgt gggacagcta caccaccaac aaggtgcacg ccatcccact gcgctcctcc    300

tgggtcatga cctgtgccta tgccccatca gggaactttg tggcatgtgg ggggctggac    360

aacatgtgtt ccatctacaa cctcaaatcc cgtgagggca atgtcaaggt cagccgggag    420

ctttctgctc acacaggtta tctctcctgc tgccgcttcc tggatgacaa caatattgtg    480

accagctcgg gggacaccac gtgtgccttg tgggacattg agactgggca gcagaagact    540

gtatttgtgg gacacacggg tgactgcatg agcctggctg tgtctcctga cttcaatctc    600

ttcatttcgg gggcctgtga tgccagtgcc aagctctggg atgtgcgaga ggggacctgc    660

cgtcagactt tcactggcca cgagtcggac atcaacgcca tctgtttctt ccccaatgga    720

gaggccatct gcacgggctc ggatgacgct tcctgccgct tgtttgacct gcgggcagac    780

caggagctga tctgcttctc ccacgagagc atcatctgcg gcatcacgtc cgtggccttc    840

tccctcagtg gccgcctact attcgctggc tacgacgact tcaactgcaa tgtctgggac    900

tccatgaagt ctgagcgtgt gggcatcctc tctggccacg ataacagggt gagctgcctg    960

ggagtcacag ctgacgggat ggctgtggcc acaggttcct gggacagctt cctcaaaatc   1020

tggaactgag gaggctggag aaagggaagt ggaaggcagt gaacacactc agcagccccc   1080

tgcccgaccc catctcattc aggtgttctc ttctatattc cgggtgccat tcccactaag   1140

ctttctcctt tgagggcagt ggggagcatg ggactgtgcc tttgggaggc agcatcaggg   1200

acacaggggc aaagaactgc cccatctcct cccatggcct tccctcccca cagtcctcac   1260

agcctctccc ttaatgagca aggacaacct gcccctcccc agccctttgc aggcccagca   1320

gacttgagtc tgaggcccca ggccctagga ttcctccccc agagccacta cctttgtcca   1380

ggcctgggtg gtatagggcg tttggccctg tgactatggc tctggcacca ctagggtcct   1440

ggccctcttc ttattcatgc tttctccttt ttctaccttt ttttctctcc taagacacct   1500

gcaataaagt gtagcaccct ggt                                            1523
```

<210> SEQ ID NO 5
<211> LENGTH: 1419
<212> TYPE: DNA
<213> ORGANISM: Homo sapiens

<400> SEQUENCE: 5

```
gaattctgag ggcagagcgg gccactttct aggcctctga tttcatactg tggtgttagt     60

tacttctgag aggacagctt gctgccagag ctctattttt tatgttagag gctccttctg    120

cctgcagact ctgctgtctg ggaagggcac agcgttagga gggagaggga ggtgtgagtc    180
```

-continued

```
cctccgtgga cccgctgctt tgtacttctc tatctcattt ccttttcagc accactctgg    240
gaaatcagta ttccagcccc attttatcct cagaaaattg aggctctgag atgttatctc    300
tgtgacctgg gtcctattac gtgccaaagg catcatttaa gcctaagatg tcctggctcc    360
aaggtgtcag catctggaag acaggcgcct catcctgcca tccctgctgc ggcttcactg    420
tggcccaggg gacatctcag cccgagaagg tcagcggccc cctcctggac caccgactcc    480
ccgcagaact cctctgtgcc ctctcctcac cagaccttgt tcctcccagt tgctcccaca    540
gccaggggc agtgagggct gctcttcccc cagccccact gaggaaccca ggaaggtgaa    600
cgagagaatc agtcctggtg ggggctgggg agggccccag acatgagacc agctcctccc    660
ccaggggatg ttatcagtgg gtccagaggg caaaataggg agcctggtgg agggaggggc    720
aaaggcctcg ggctctgagc ggccttggcc ttctccacca acccctccct acactcaggg    780
ggaggcggcg gtggggcaca cagggtgggg ggcgggtggc gggctgctgg gtgagcagca    840
ctcgcctgcc tggattgaaa cccagagatg gaggtgctgg gaggggctgt gagagctcag    900
ccctgtaacc aggccttgcc ggagccactg atgcccggtc ttctgtgcct ttactccaaa    960
catcccccag cccaagccac ccacttgttc tcaagtctga agaagaagtc cctcacccct   1020
ctactccagg ctgtgttcag ggcttggggc tggtggaggg aggggcctga aattccagtg   1080
tgaaaggctg agatgcccga gcccctggcc tatgtccaag ccatttcccc tctctcacca   1140
gcctctccct ggggagccag tcagctagga aggaatgagg gctccccagg cccaccccca   1200
gttcctgagc tcatctgggc tgcagggctg gcgggacagc agcgtggact cagtctccta   1260
gggatttccc aactctcccg cccgcttgct gcatctggac accctgcctc aggccctcat   1320
ctccactggt cagcaggtga cctttgccca gcgccctggg tcctcagtgc ctgctgccct   1380
ggagatgata taaaacaggt cagaaccctc ctgcctgtc                          1419
```

```
<210> SEQ ID NO 6
<211> LENGTH: 1278
<212> TYPE: DNA
<213> ORGANISM: Homo sapiens

<400> SEQUENCE: 6

ccagacaagt gatttttgag gagtccctat ctataggaac aaagtaatta aaaaaatgta     60
tttcagaatt tacaggccca tgtgagatat gattttttta aatgaagatt tagagtaatg    120
ggtaaaaaag aggtatttgt gtgtttgttg attgttcagt cagtgaatgt acagcttctg    180
cctcatatcc aggcaccatc tcttcctgct ctttgttgtt aaatgttcca ttcctgggta    240
atttcatgtc tgccatcgtg gatatgccgt ggctccttga acctgcttgt gttgaagcag    300
gatcttcctt cctgtccctt cagtgcccta ataccatgta tttaaggctg gacacatcac    360
cactcccaac ctgcctcacc cactgcgtca cttgtgatca ctggcttctg gcgactctca    420
ccaaggtctc tgtcatgccc tgttataacg actacaaaag caagtcttac ctataggaaa    480
ataagaatta taacccttttt actggtcatg tgaaacttac catttgcaat ttgtacagca    540
taaacacaga acagcacatc tttcaatgcc tgcatcctga aggcattttg tttgtgtctt    600
tcaatctggc tgtgctattg ttggtgttta acagtctccc cagctacact ggaaacttcc    660
agaaggcact tttcacttgc ttgtgtgttt tccccagtgt ctattagagg cctttgcaca    720
gggtaggctc tttggagcag ctgaaggtca cacatcccat gagcgggcag cagggtcaga    780
agtggccccc gtgttgccta agcaagactc tcccctgccc tctgccctct gcacctccgg    840
cctgcatgtc cctgtggcct cttgggggta catctcccgg ggctgggtca gaaggcctgg    900
```

-continued

```
gtggttggcc tcaggctgtc acacacctag ggagatgctc ccgtttctgg gaaccttggc    960

cccgactcct gcaaacttcg gtaaatgtgt aactcgaccc tgcaccggct cactctgttc   1020

agcagtgaaa ctctgcatcg atcactaaga cttcctggaa gaggtcccag cgtgagtgtc   1080

gcttctggca tctgtccttc tggccagcct gtggtctggc caagtgatgt aaccctcctc   1140

tccagcctgt gcacaggcag cctgggaaca gctccatccc caccccctcag ctataaatag   1200

ggcctcgtga cccggccagg ggaagaagct gccgttgttc tgggtactac agcagaaggt   1260

aagccggggg ccccctca                                                 1278
```

<210> SEQ ID NO 7
<211> LENGTH: 3074
<212> TYPE: DNA
<213> ORGANISM: Homo sapiens

<400> SEQUENCE: 7

```
gaattccggg gagcaggaag agccaacatg ctggccccgc gcggagccgc cgtcctcctg     60

ctgcacctgg tcctgcagcg gtggctagcg gcaggcgccc aggccacccc ccaggtcttt    120

gaccttctcc catcttccag tcagaggcta aacccaggcg ctctgctgcc agtcctgaca    180

gaccccgccc tgaatgatct ctatgtgatt tccaccttca agctgcagac taaaagttca    240

gccaccatct tcggtcttta ctcttcaact gacaacagta aatattttga atttactgtg    300

atgggacgct taagcaaagc catcctccgt tacctgaaga acgatgggaa ggtgcatttg    360

gtggttttca acaacctgca gctggcagac ggaaggcggc acaggatcct cctgaggctg    420

agcaatttgc agcgaggggc cggctcccta gagctctacc tggactgcat ccaggtggat    480

tccgttcaca atctccccag ggcctttgct ggcccctccc agaaacctga gaccattgaa    540

ttgaggactt tccagaggaa gccacaggac ttcttggaag agctgaagct ggtggtgaga    600

ggctcactgt tccaggtggc cagcctgcaa gactgcttcc tgcagcagag tgagccactg    660

gctgccacag gcacagggga ctttaaccgg cagttcttgg gtcaaatgac acaattaaac    720

caactcctgg gagaggtgaa ggaccttctg agacagcagg ttaaggaaac atcatttttg    780

cgaaacacca tagctgaatg ccaggcttgc ggtcctctca agtttcagtc tccgacccca    840

agcacggtgg tcgccccggc tccccctgca ccgccaacac gcccacctcg tcggtgtgac    900

tccaacccat gtttccgagg tgtccaatgt accgacagta gagatggctt ccagtgtggg    960

ccctgccccg agggctacac aggaaacggg atcacctgta ttgatgttga tgagtgcaaa   1020

taccatccct gctacccggg cgtgcactgc ataaatttgt ctcctggctt cagatgtgac   1080

gcctgcccag tgggcttcac agggcccatg gtgcagggtg ttgggatcag ttttgccaag   1140

tcaaacaagc aggtctgcac tgacattgat gagtgtcgaa atggagcgtg cgttcccaac   1200

tcgatctgcg ttaatacttt gggatcttac cgctgtgggc cttgtaagcc ggggtatact   1260

ggtgatcaga taaggggatg caaagtggaa agaaactgca gaaacccaga gctgaaccct   1320

tgcagtgtga atgcccagtg cattgaagag aggcaggggg atgtgacatg tgtgtgtgga   1380

gtcggttggg ctggagatgg ctatatctgt ggaaaggatg tggacatcga cagttacccc   1440

gacgaagaac tgccatgctc tgccaggaac tgtaaaaagg acaactgcaa atatgtgcca   1500

aattctggcc aagaagatgc agacagagat ggcattggcg acgcttgtga cgaggatgct   1560

gacggagatg ggatcctgaa tgagcaggat aactgtgtcc tgattcataa tgtggaccaa   1620

aggaacagcg ataaagatat ctttggggat gcctgtgata actgcctgag tgtcttaaat   1680

aacgaccaga aagacaccga tggggatgga agaggagatg cctgtgatga tgacatggat   1740
```

-continued

```
ggagatggaa taaaaaacat tctggacaac tgcccaaaat ttcccaatcg tgaccaacgg   1800

gacaaggatg gtgatggtgt gggggatgcc tgtgacagtt gtcctgatgt cagcaacccct  1860

aaccagtctg atgtggataa tgatctggtt ggggactcct gtgacaccaa tcaggacagt   1920

gatggagatg ggcaccagga cagcacagac aactgcccca ccgtcattaa cagtgcccag   1980

ctggacaccg ataaggatgg aattggtgac gagtgtgatg atgatgatga caatgatggt   2040

atcccagacc tggtgccccc tggaccagac aactgccggc tggtccccaa cccagcccag   2100

gaggatagca acagcgacgg agtgggagac atctgtgagt ctgactttga ccaggaccag   2160

gtcatcgatc ggatcgacgt ctgcccagag aacgcagagg tcaccctgac cgacttcagg   2220

gcttaccaga ccgtgggcct ggatcctgaa ggggatgccc agatcgatcc caactgggtg   2280

gtcctgaacc agggcatgga gattgtacag accatgaaca gtgatcctgg cctggcagtg   2340

gggtacacag cttttaatgg agttgacttc gaagggacct tccatgtgaa tacccagaca   2400

gatgatgact atgcaggctt tatctttggc taccaagata gctccagctt ctacgtggtc   2460

atgtggaagc agacggagca gacatattgg caagccaccc cattccgagc agttgcagaa   2520

cctggcattc agctcaaggc tgtgaagtct aagacaggtc caggggagca tctccggaac   2580

tccctgtggc acacgggga caccagtgac caggtcaggc tgctgtggaa ggactccagg   2640

aatgtgggct ggaaggacaa ggtgtcctac cgctggttcc tacagcacag gccccaggtg   2700

ggctacatca gggtacgatt ttatgaaggc tctgagttgg tggctgactc tggcgtcacc   2760

atagacacca caatgcgtgg aggccgactt ggcgttttct gcttctctca agaaaacatc   2820

atctggtcca acctcaagta tcgctgcaat gacaccatcc ctgaggactt ccaagagttt   2880

caaacccaga atttcgaccg cttcgataat taaaccaagg aagcaatctg taactgcttt   2940

tcggaacact aaaaccatat atattttaac ttcaattttc tttagctttt accaacccaa   3000

atatatcaaa acgttttatg tgaatgtggc aataaaggag aagagatcat ttttaaaaaa   3060

aaaaaaaaaa aaaa                                                     3074


<210> SEQ ID NO 8
<211> LENGTH: 4593
<212> TYPE: DNA
<213> ORGANISM: Homo sapiens

<400> SEQUENCE: 8

ggatccagct gtctctcctt gcgatcctgt cttcggggaa gtccacgtcc taggcaggtc     60

ctcccaaagt gcccttggtg ccgatcaccc ctcccagcgt cttgcaggtc ctgtgcacca    120

cctcccccac tccccattca aagccctctt ctctgaagtc tccggttccc agagctcttg    180

caatccaggc tttccttgga agtggctgta acatgtatga aaagaaagaa aggaggacca    240

agagatgaaa gagggctgca cgcgtggggg cccgagtggt gggcggggac agtcgtcttg    300

ttacaggggt gctggccttc cctggcgcct gcccctgtcg gccccgcccg agaacctccc    360

tgcgccaggg cagggtttac tcatcccggc gaggtgatcc catgcgcgag ggcgggcgca    420

agggcggcca gagaacccag caatccgagt atgcggcatc agcccttccc accaggcact    480

tccttccttt tcccgaacgt ccagggaggg agggccgggc acttataaac tcgagccctg    540

gccgatccgc atgtcagagg ctgcctcgca ggggctgcgc gcagcggcaa gaagtgtctg    600

ggctgggacg gacaggagag gctgtcgcca tcggcgtcct gtgcccctct gctccggcac    660

ggccctgtcg cagtgcccgc gctttccccg gcgcctgcac gcggcgcgcc tgggtaacat    720

gcttggggtc ctggtccttg gcgcgctggc cctggccggc ctggggttcc ccgcacccgc    780
```

-continued

```
agagccgcag ccgggtggca gccagtgcgt cgagcacgac tgcttcgcgc tctacccggg    840
ccccgcgacc ttcctcaatg ccagtcagat ctgcgacgga ctgcggggcc acctaatgac    900
agtgcgctcc tcggtggctg ccgatgtcat ttccttgcta ctgaacggcg acggcggcgt    960
tggccgccgg cgcctctgga tcggcctgca gctgccaccc ggctgcggcg accccaagcg   1020
cctcgggccc ctgcgcggct tccagtgggt tacgggagac aacaacacca gctatagcag   1080
gtgggcacgg ctcgacctca atggggctcc cctctgcggc ccgttgtgcg tcgctgtctc   1140
cgctgctgag gccactgtgc ccagcgagcc gatctgggag gagcagcagt gcgaagtgaa   1200
ggccgatggc ttcctctgcg agttccactt cccagccacc tgcaggccac tggctgtgga   1260
gcccggcgcc gcggctgccg ccgtctcgat cacctacggc accccgttcg cggcccgcgg   1320
agcggacttc caggcgctgc cggtgggcag ctccgccgcg gtggctcccc tcggcttaca   1380
gctaatgtgc accgcgccgc ccggagcggt ccaggggcac tgggccaggg aggcgccggg   1440
cgcttgggac tgcagcgtgg agaacggcgg ctgcgagcac gcgtgcaatg cgatccctgg   1500
ggctccccgc tgccagtgcc cagccggcgc cgccctgcag gcagacgggc gctcctgcac   1560
cgcatccgcg acgcagtcct gcaacgacct ctgcgagcac ttctgcgttc ccaaccccga   1620
ccagccgggc tcctactcgt gcatgtgcga gaccggctac cggctggcgg ccgaccaaca   1680
ccggtgcgag gacgtggatg actgcatact ggagcccagt ccgtgtccgc agcgctgtgt   1740
caacacacag ggtggcttcg agtgccactg ctaccctaac tacgacctgg tggacggcga   1800
gtgtgtggag cccgtggacc cgtgcttcag agccaactgc gagtaccagt gccagcccct   1860
gaaccaaact agctacctct gcgtctgcgc cgagggcttc gcgcccattc cccacgagcc   1920
gcacaggtgc cagatgtttt gcaaccagac tgcctgtcca gccgactgcg accccaacac   1980
ccaggctagc tgtgagtgcc ctgaaggcta catcctggac gacggtttca tctgcacgga   2040
catcgacgag tgcgaaaacg gcggcttctg ctccggggtg tgccacaacc tccccggtac   2100
cttcgagtgc atctgcgggc ccgactcggc ccttgtccgc cacattggca ccgactgtga   2160
ctccggcaag gtggacggtg gcgacagcgg ctctggcgag cccccgccca gcccgacgcc   2220
cggctccacc ttgactcctc cggccgtggg gctcgtgcat tcgggcttgc tcataggcat   2280
ctccatcgcg agcctgtgcc tggtggtggc gcttttggcg ctcctctgcc acctgcgcaa   2340
gaagcagggc gccgccaggg ccaagatgga gtacaagtgc gcggcccctt ccaaggaggt   2400
agtgctgcag cacgtgcgga ccgagcggac gccgcagaga ctctgagcgg cctccgtcca   2460
ggagcctggc tccgtccagg agcctgtgcc tcctcacccc cagctttgct accaaagcac   2520
cttagctggc attacagctg gagaagaccc tccccgcacc ccccaagctg ttttcttcta   2580
ttccatggct aactggcgag gggtgatta gagggaggag aatgagcctc ggcctcttcc   2640
gtgacgtcac tggaccactg ggcaatgatg gcaattttgt aacgaagaca cagactgcga   2700
tttgtcccag gtcctcacta ccgggcgcag gagggtgagc gttattggtc ggcagccttc   2760
tgggcagacc ttgacctcgt gggctaggga tgactaaaat atttattttt tttaagtatt   2820
taggtttttg tttgtttcct ttgttcttac ctgtatgtct ccagtatcca ctttgcacag   2880
ctctccggtc tctctctctc tacaaactcc cacttgtcat gtgacaggta aactatcttg   2940
gtgaattttt ttttcctagc cctctcacat ttatgaagca agccccactt attccccatt   3000
cttcctagtt ttctcctccc aggaactggg ccaactcacc tgagtcaccc tacctgtgcc   3060
tgaccctact tcttttgctc ttagctgtct gctcagacag aacccctaca tgaaacagaa   3120
acaaaaacac taaaaataaa aatggccatt tgctttttca ccagatttgc taatttatcc   3180
```

-continued

```
tgaaatttca gattcccaga gcaaaataat tttaaacaaa ggttgagatg taaaaggtat   3240
taaattgatg ttgctggact gtcatagaaa ttacacccaa agaggtattt atctttactt   3300
ttaaacagtg agcctgaatt ttgttgctgt tttgatttgt actgaaaaat ggtaattgtt   3360
gctaatcttc ttatgcaatt tcctttttttg ttattattac ttatttttga cagtgttgaa   3420
aatgttcaga aggttgctct agattgcgag aagagacaaa cacctcccag gagacagttc   3480
aagaaagctt caaactgcat gattcatgcc aattagcaat tgactgtcac tgttccttgt   3540
cactggtaga ccaaaataaa accagctcta ctggtcttgt ggaattggga gcttgggaat   3600
ggatcctgga ggatgcccaa ttagggccta gccttaatca ggtcctcaga gaatttctac   3660
catttcagag aggccttttg gaatgtggcc cctgaacaag aattggaagc tgccctgccc   3720
atgggagctg gttagaaatg cagaatccta ggctccaccc catccagttc atgagaatct   3780
atatttaaca agatctgcag gggtgtgtc tgctcagtaa tttgaggaca accattccag   3840
actgcttcca attttctgga atacatgaaa tatagatcag ttataagtag caggccaagt   3900
caggccctta ttttcaagaa actgaggaat tttctttgtg tagctttgct ctttggtaga   3960
aaaggctagg tacacagctc tagacactgc cacacagggt ctgcaaggtc tttggttcag   4020
ctaagctagg aatgaaatcc tgcttcagtg tatggaaata aatgtatcat agaaatgtaa   4080
cttttgtaag acaaaggttt tcctcttcta ttttgtaaac tcaaaatatt tgtacatagt   4140
tatttattta ttggagataa tctagaacac aggcaaaatc cttgcttatg acatcacttg   4200
tacaaaataa acaaataaca atgtgctctc gggttgtgtg tctgttcatt ttcctccctc   4260
agtgccctca ttttatgtca ttaaatgggg ctcacaaacc atgcaaatgc tatgagatgc   4320
atggagggct gccctgtacc ccagcacttg tgttgtctgg tgatggcacc atctctgatt   4380
ttcaaagctt tttccagagg ctattatttt cactgtagaa tgatttcatg ctatctctgt   4440
gtgcacaaat atttattttc tttctgtaac cataacaact tcatatatga ggacttgtgt   4500
ctctgtgctt ttaaatgcat aaatgcatta taggatcatt tgttggaatg aattaaataa   4560
acccttcctg ggcatctgg cgaatcccag ctg                              4593
```

<210> SEQ ID NO 9
<211> LENGTH: 6163
<212> TYPE: DNA
<213> ORGANISM: Homo sapiens

<400> SEQUENCE: 9

```
tggggtctcc cccctctgtg tggggagaag tgtgccagag agacgcatgt cctcctcctg     60
tggaggggct gttctccacc accacatgtc ttcctaccaa tctgctcccc agagggctgc    120
ctgctgtgca cttgggtcct ggagcccttc tccacccggt gagtggccag cagggtgtgg    180
ggttatgtga gggtagaaag gacagcaaag agaaatggcc tcccagctgg gggaggggca    240
ggcaaactgg aacctacagg cactgacctt tgtcgagaag agtgtagcct tcccagaatg    300
ggaggagcag ggcagagcag gggtaggggg tggggtgctg ttttctgagg gactgatcac    360
ttacttggtg gaatacagca cagccctggc tggccctaag gaaaggggac atgagcccag    420
ggagaaaata agagagggag ctgcacttag ggcttagcaa acacagtagt aagatggaca    480
cagccccaat ccccattctt agctggtcat tcctcgttag cttaaggttc tgaatctggt    540
gctggggaag ctgggccagg caagccaggg cgcaaggaga gggtaatggg aggaggccca    600
ctcatgttga cagacctaca ggaaatccca atattgaatc aggtgcaagc ctctttgcac    660
aacttgtgaa aggaggagga agccatgtgg ggggtcctgt gaaggaaccg gaaggggttc    720
```

-continued

```
tgccaagggg gcagggaggc aggtgtgatc tatgagacag atatgttagt gggcgcctaa    780
gacaaggtaa gcccctaagg tgggcatcac ccagcaggtg cccgttcctg ggcagctggt    840
ctcaggaagg aagtcccaga actgttagcc catctcttgg cctcagataa tggagtattt    900
caggacttgg agtccagaga aaagctccag tggctttatg tgtgggggta gatagggaaa    960
gatagaggtt aatttctccc ataccgcctt ttaatcctga cctctagtgg tcccagttac   1020
agctttgtgc agttcccctc cccagcccca ctccccaccg cagaagttac ccctcaacat   1080
attgcgcccg tttgccagtt cctcacccag gccctgcatc ccattttcca ctctcttctc   1140
caggctgaag ccacaatact ttccttctct atccccatcc cagattttct ctgacctaac   1200
aaccaaggtt gctcagaatt taaggctaat taagatatgt gtgtatacat atcatgtcct   1260
gctgctctca gcaggggtag gtggcaccaa atccatgtcc gattcactga ggagtcctga   1320
caaaaaggag acaccatatg ctttcttgct ttctttcttt ctttctttct ttcttttttt   1380
tttttgagac ggagtttcac tcttattgcc caggctggag tgcaatggtg cgatctcggc   1440
tcaccacaac ctccgcctcc caggtacaag cgattctcct gtctcagcct cccaagtagc   1500
ttggattaca ggcatgaacc accacaccct gctagttttt ttgtatttcg tagagccggg   1560
gtttcaccat gttagtgagg ctggtggcga actcctgacc tcaggtgatc cacccgcctt   1620
ggactcccaa agtgctggga ttacaggcat gagccactgc acccggcaca ccatatgctt   1680
tcatcacaag aaaatgtgag agaattcagg gctttggcag ttccaggctg gtcagcatct   1740
caagccctcc ccagcatctg ttcaccctgc caggcagtct cttcctagaa acttggttaa   1800
atgttcactc ttcttgctac tttcaggata gattcttcac ccttggtccg cctttgcccc   1860
accctactct gcccagaagt gcaagagcct aagccgcctc catggcccca ggaaggattc   1920
aggggagagg ccccaaacag ggagccacgc cagccagaca ccccggccag aatggagctg   1980
actggtgaga acacacctga ggggctaggg ccatatggaa acatgacaga aggggagaga   2040
gaaaggagac acgctgcagg gggcaggaag ctgggggaac ccattctccc aaaaataagg   2100
ggtctgaggg gtggattccc tgggtttcag gtctgggtcc tgaatgggaa ttcctggaat   2160
accagctgac aatgatttcc tcctcatctt tcaacctcac ctctcctcat ctaagaattg   2220
ctcctcgtgg tcatgcttct cctaactgca aggctaacgc tgtccagccc ggctcctcct   2280
gcttgtgacc tccgagtcct cagtaaactg cttcgtgact cccatgtcct tcacagcaga   2340
ctggtgagaa ctcccaacat tatccccttt atccgcgtaa ctggtaagac acccatactc   2400
ccaggaagac accatcactt cctctaactc cttgacccaa tgactattct tcccatattg   2460
tccccaccta ctgatcacac tctctgacaa ggattattct tcacaataca gcccgcattt   2520
aaaagctctc gtctagagat agtactcatg gaggactagc ctgcttatta ggctaccata   2580
gctctctcta tttcagctcc cttctccccc caccaatctt tttcaacaga gccagtgccc   2640
agaggttcac cctttgccta cacctgtcct gctgcctgct gtggacttta gcttgggaga   2700
atggaaaacc cagatggtaa gaaagccatc cctaaccttg gcttccctaa gtcctgtctt   2760
cagtttccca ctgcttccca tggattctcc aacattcttg agctttttaa aaatatctca   2820
ccttcagctt ggccacccta acccaatcta cattcaccta tgatgatagc ctgtggataa   2880
gatgatggct tgcaggtcca atatgtgaat agatttgaag ctgaacacca tgaaaagctg   2940
gagagaaatc gctcatggcc atgcctttga cctattcccg ttcagtcttc ttaaattggc   3000
atgaagaagc aagactcata tgtcatccac agatgacaca aagctgggaa gtaccactaa   3060
aataacaaaa gactgaatca agattcaaat cactgaaaga ctaggtcaaa aacaaggtga   3120
```

-continued

```
aacaacagag atataaactt ctacatgtgg gccgggggct cacgcctgta atcccagcac   3180
tttgggaggc cgaggcaggc agatcacctg agggcaggag tttgagagca gcctggccaa   3240
catggcgaaa ccccgtctct actaagaata cagaattagc cgggcatggt agtgcatgcc   3300
tgtaatccca gctacttgga aggctgaagc aggagaatcc cttgaaccca ggaggtggag   3360
gttgtagtga gctgagatca tgccaatgca ctccagcctg ggtgacaaga gcaaaactcc   3420
gtctcaaaaa gaaaaaaaaa ttctacatgt gtaaattaat gagtaaagtc ctattccagc   3480
tttcaggcca caatgccctg cttccatcat ttaagcctct ggccctagca cttcctacga   3540
aaaggatctg agagaattaa attgccccca aacttaccat gtaacattac tgaagctgct   3600
attcttaaag ctagtaattc ttgtctgttt gatgtttagc atccccattg tggaaatgct   3660
cgtacagaac tctattccga gtggactaca cttaaatata ctggcctgaa caccggacat   3720
cccccctgaag acatatgcta atttattaag agggaccata ttaaactaac atgtgtctag   3780
aaagcagcag cctgaacaga aagagactag aagcatgttt tatgggcaat agtttaaaaa   3840
actaaaatct atcctcaaga accctagcgt cccttcttcc ttcaggactg agtcagggaa   3900
gaagggcagt tcctatgggt cccttctagt cctttctttt catccttatg atcattatgg   3960
tagagtctca tacctacatt tagtttattt attattatta tttgagacgg agtctcactc   4020
tatcccccag gctggagtgc agtggcatga tctcaactca ctgcaacctc agcctcccgg   4080
attcaagcga ttctcctgtc tcagtctccc aagtagctgg gattacaggt gcccaccacc   4140
atgcccagct aatttgtgta tttgtggtag agatggggtt tcaccatgtt gggcaggctg   4200
atcttgaact cctgacctca ggtgatccac ctgcctcagc ctcccaaagt gctgggatta   4260
caggcgtgag ccactgcacc cagccttcat tcagtttaaa aatcaaatga tcctaaggtt   4320
ttgcagcaga aagagtaaat ttgcagcact agaaccaaga ggtaaaagct gtaacagggc   4380
agatttcagc aacgtaagaa aaaaggagct cttctcactg aaaccaagtg taagaccagg   4440
ctggactaga ggacacggga gtttttgaag cagaggctga tgaccagctg tcgggagact   4500
gtgaaggaat tcctgccctg ggtgggacct tggtcctgtc cagttctcag cctgtatgat   4560
tcactctgct ggctactcct aaggctcccc acccgctttt agtgtgccct ttgaggcagt   4620
gcgcttctct cttccatctc tttctcagga ggagaccaag gcacaggaca ttctgggagc   4680
agtgaccctt ctgctggagg gagtgatggc agcacgggga caactgggac ccacttgcct   4740
ctcatccctc ctggggcagc tttctggaca ggtccgtctc ctccttgggg ccctgcagag   4800
cctccttgga acccaggtaa gtccccagtc aagggatctg tagaaactgt tcttttctga   4860
ctcagtcccc ctagaagacc tgagggaaga agggctcttc cagggagctc aagggcagaa   4920
gagctgatct actaagagtg ctccctgcca gccacaatgc ctgggtactg gcatcctgtc   4980
tttcctactt agacaaggga ggcctgagat ctggccctgg tgtttggcct caggaccatc   5040
ctctgccctc agcttcctcc acagggcagg accacagctc acaaggatcc caatgccatc   5100
ttcctgagct tccaacacct gctccgagga aaggtgcgtt tcctgatgct tgtaggaggg   5160
tccaccctct gcgtcaggcg ggccccaccc accacagctg tccccagcag aacctctcta   5220
gtcctcacac tgaacgagct cccaaacagg acttctggat tgttggagac aaacttcact   5280
gcctcagcca gaactactgg ctctgggctt ctgaagtggc agcagggatt cagagccaag   5340
attcctggtc tgctgaacca aacctccagg tccctggacc aaatccccgg atacctgaac   5400
aggatacacg aactcttgaa tggaactcgt ggactctttc ctggaccctc acgcaggacc   5460
ctaggagccc cggacatttc ctcaggaaca tcagacacag gctccctgcc acccaacctc   5520
```

-continued

```
cagcctggat attctccttc cccaacccat cctcctactg gacagtatac gctcttccct   5580
cttccaccca ccttgcccac ccctgtggtc cagctccacc ccctgcttcc tgacccttct   5640
gctccaacgc ccacccctac cagccctctt ctaaacacat cctacaccca ctcccagaat   5700
ctgtctcagg aagggtaagg ttctcagaca ctgccgacat cagcattgtc tcgtgtacag   5760
ctcccttccc tgcagggcgc ccctgggaga caactggaca agatttccta ctttctcctg   5820
aaacccaaag ccctggtaaa agggatacac aggactgaaa agggaatcat tttcactgt    5880
acattataaa ccttcagaag ctattttttt aagctatcag caatactcat cagagcagct   5940
agctctttgg tctattttct gcagaaattt gcaactcact gattctcaac atgctctttt   6000
tctgtgataa ctctgcaaag acctgggctg gcctggcagt tgaacagagg gagagactaa   6060
ccttgagtca gaaaacagag gaagggtaat ttcctttgct tcaaattcaa ggccttccaa   6120
cgccccccatc ccctttacta tcattctcag tgggactctg atc                    6163
```

<210> SEQ ID NO 10
<211> LENGTH: 1505
<212> TYPE: DNA
<213> ORGANISM: Homo sapiens

<400> SEQUENCE: 10

```
gctggtcgga ggctcgcagt gctgtcggcg agaagcagtc gggtttggag cgcttgggtc     60
gcgttggtgc gcggtggaac gcgcccaggg accccagttc ccgcgagcag ctccgcgccg    120
cgcctgagag actaagctga aactgctgct cagctcccaa gatggtgcca cccaaattgc    180
atgtgctttt ctgcctctgc ggctgcctgg ctgtggttta tcctttttgac tggcaataca   240
taaatcctgt tgcccatatg aaatcatcag catgggtcaa caaaatacaa gtactgatgg    300
ctgctgcaag ctttggccaa actaaaatcc cccggggaaa tgggccttat tccgttggtt    360
gtacagactt aatgtttgat cacactaata agggcacctt cttgcgttta tattatccat    420
cccaagataa tgatcgcctt gacacccttt ggatcccaaa taaagaatat ttttggggtc    480
ttagcaaatt tcttggaaca cactggctta tgggcaacat tttgaggtta ctctttggtt    540
caatgacaac tcctgcaaac tggaattccc ctctgaggcc tggtgaaaaa tatccacttg    600
ttgttttttc tcatggtctt ggggcattca ggacacttta ttctgctatt ggcattgacc    660
tggcatctca tgggtttata gttgctgctg tagaacacag agatagatct gcatctgcaa    720
cttactattt caaggaccaa tctgctgcag aaatagggga caagtcttgg ctctacctta    780
gaaccctgaa acaagaggag gagacacata tacgaaatga gcaggtacgg caaagagcaa    840
aagaatgttc ccaagctctc agtctgattc ttgacattga tcatggaaag ccagtgaaga    900
atgcattaga tttaaagttt gatatggaac aactgaagga ctctattgat agggaaaaaa    960
tagcagtaat tggacattct tttggtggag caacggttat tcagactctt agtgaagatc   1020
agagattcag atgtggtatt gccctggatg catggatgtt tccactgggt gatgaagtat   1080
attccagaat tcctcagccc ctctttttta tcaactctga atatttccaa tatcctgcta   1140
atatcataaa aatgaaaaaa tgctactcac ctgataaaga aagaaagatg attacaatca   1200
ggggttcagt ccaccagaat tttgctgact tcacttttgc aactggcaaa ataattggac   1260
acatgctcaa attaaaggga gacatagatt caaatgtagc tattgatctt agcaacaaag   1320
cttcattagc attcttacaa aagcatttag gacttcataa agattttgat cagtgggact   1380
gcttgattga aggagatgat gagaatctta ttccagggac caacattaac acaaccaatc   1440
```

aacacatcat gttacagaac tcttcaggaa tagagaaata caattaggat taaaataggt 1500
ttttt 1505

<210> SEQ ID NO 11
<211> LENGTH: 3834
<212> TYPE: DNA
<213> ORGANISM: Homo sapiens

<400> SEQUENCE: 11
cctgagacag aggcagcagt gatacccacc tgagagatcc tgtgtttgaa caactgcttc 60
ccaaaacgga aagtatttca agcctaaacc tttgggtgaa aagaactctt gaagtcatga 120
ttgcttcaca gtttctctca gctctcactt tggtgcttct cattaaagag agtggagcct 180
ggtcttacaa cacctccacg gaagctatga cttatgatga ggccagtgct tattgtcagc 240
aaaggtacac acacctggtt gcaattcaaa acaaagaaga gattgagtac ctaaactcca 300
tattgagcta ttcaccaagt tattactgga ttggaatcag aaaagtcaac aatgtgtggg 360
tctgggtagg aacccagaaa cctctgacag aagaagccaa gaactgggct ccaggtgaac 420
ccaacaatag gcaaaaagat gaggactgcg tggagatcta catcaagaga gaaaaagatg 480
tgggcatgtg gaatgatgag aggtgcagca agaagaagct tgccctatgc tacacagctg 540
cctgtaccaa tacatcctgc agtggccacg gtgaatgtgt agagaccatc aataattaca 600
cttgcaagtg tgaccctggc ttcagtggac tcaagtgtga gcaaattgtg aactgtacag 660
ccctggaatc ccctgagcat ggaagcctgg tttgcagtca cccactggga aacttcagct 720
acaattcttc ctgctctatc agctgtgata ggggttacct gccaagcagc atggagacca 780
tgcagtgtat gtcctctgga gaatggagtg ctcctattcc agcctgcaat gtggttgagt 840
gtgatgctgt gacaaatcca gccaatgggt tcgtggaatg tttccaaaac cctggaagct 900
tcccatggaa cacaacctgt acatttgact gtgaagaagg atttgaacta atgggagccc 960
agagccttca gtgtacctca tctgggaatt gggacaacga gaagccaacg tgtaaagctg 1020
tgacatgcag ggccgtccgc cagcctcaga atggctctgt gaggtgcagc cattcccctg 1080
ctggagagtt caccttcaaa tcatcctgca acttcacctg tgaggaaggc ttcatgttgc 1140
agggaccagc ccaggttgaa tgcaccactc aagggcagtg gacacagcaa atcccagttt 1200
gtgaagcttt ccagtgcaca gccttgtcca accccgagcg aggctacatg aattgtcttc 1260
ctagtgcttc tggcagtttc cgttatgggt ccagctgtga gttctcctgt gagcagggtt 1320
ttgtgttgaa gggatccaaa aggctccaat gtggccccac aggggagtgg gacaacgaga 1380
agcccacatg tgaagctgtg agatgcgatg ctgtccacca gcccccgaag ggtttggtga 1440
ggtgtgctca ttcccctatt ggagaattca cctacaagtc ctcttgtgcc ttcagctgtg 1500
aggagggatt tgaattatat ggatcaactc aacttgagtg cacatctcag ggacaatgga 1560
cagaagaggt tccttcctgc caagtggtaa aatgttcaag cctggcagtt ccgggaaaga 1620
tcaacatgag ctgcagtggg gagcccgtgt ttggcactgt gtgcaagttc gcctgtcctg 1680
aaggatggac gctcaatggc tctgcagctc ggacatgtgg agccacagga cactggtctg 1740
gcctgctacc tacctgtgaa gctcccactg agtccaacat tcccttggta gctggacttt 1800
ctgctgctgg actctccctc ctgacattag caccatttct cctctggctt cggaaatgct 1860
tacggaaagc aaagaaattt gttcctgcca gcagctgcca aagccttgaa tcagacggaa 1920
gctaccaaaa gccttcttac atcctttaag ttcaaaagaa tcagaaacag gtgcatctgg 1980
ggaactagag ggatacactg aagttaacag agacagataa ctctcctcgg gtctctggcc 2040

-continued

```
cttcttgcct actatgccag atgcctttat ggctgaaacc gcaacaccca tcaccacttc   2100

aatagatcaa agtccagcag gcaaggacgg ccttcaactg aaaagactca gtgttccctt   2160

tcctactctc aggatcaaga aagtgttggc taatgaaggg aaaggatatt ttcttccaag   2220

caaaggtgaa gagaccaaga ctctgaaatc tcagaattcc ttttctaact ctcccttgct   2280

cgctgtaaaa tcttggcaca gaaacacaat attttgtggc tttctttctt ttgcccttca   2340

cagtgtttcg acagctgatt acacagttgc tgtcataaga atgaataata attatccaga   2400

gtttagagga aaaaaatgac taaaaatatt ataacttaaa aaaatgacag atgttgaatg   2460

cccacaggca aatgcatgga gggttgttaa tggtgcaaat cctactgaat gctctgtgcg   2520

agggttacta tgcacaattt aatcactttc atccctatgg gattcagtgc ttcttaaaga   2580

gttcttaagg attgtgatat ttttacttgc attgaatata ttataatctt ccatacttct   2640

tcattcaata caagtgtggt agggacttaa aaaacttgta aatgctgtca actatgatat   2700

ggtaaaagtt acttattcta gattaccccc tcattgttta ttaacaaatt atgttacatc   2760

tgttttaaat ttatttcaaa aagggaaact attgtcccct agcaaggcat gatgttaacc   2820

agaataaagt tctgagtgtt tttactacag ttgtttttg aaaacatggt agaattggag   2880

agtaaaaact gaatggaagg tttgtatatt gtcagatatt ttttcagaaa tatgtggttt   2940

ccacgatgaa aaacttccat gaggccaaac gttttgaact aataaaagca taaatgcaaa   3000

cacacaaagg tataatttta tgaatgtctt tgttggaaaa gaatacagaa agatggatgt   3060

gctttgcatt cctacaaaga tgtttgtcag atgtgatatg taaacataat tcttgtatat   3120

tatggaagat tttaaattca caatagaaac tcaccatgta aaagagtcat ctggtagatt   3180

tttaacgaat gaagatgtct aatagttatt ccctatttgt tttcttctgt atgttagggt   3240

gctctggaag agaggaatgc ctgtgtgagc aagcatttat gtttatttat aagcagattt   3300

aacaattcca aaggaatctc cagttttcag ttgatcactg gcaatgaaaa attctcagtc   3360

agtaattgcc aaagctgctc tagccttgag gagtgtgaga atcaaaactc tcctacactt   3420

ccattaactt agcatgtgtt gaaaaaaaaa gtttcagaga agttctggct gaacactggc   3480

aacgacaaag ccaacagtca aaacagagat gtgataagga tcagaacagc agaggttctt   3540

ttaaaggggc agaaaaactc tgggaaataa gagagaacaa ctactgtgat caggctatgt   3600

atggaataca gtgttatttt ctttgaaatt gtttaagtgt tgtaaatatt tatgtaaact   3660

gcattagaaa ttagctgtgt gaaataccag tgtggtttgt gtttgagttt tattgagaat   3720

tttaaattat aacttaaaat attttataat ttttaaagta tatatttatt taagcttatg   3780

tcagacctat ttgacataac actataaagg ttgacaataa atgtgcttat gttt         3834
```

<210> SEQ ID NO 12
<211> LENGTH: 5204
<212> TYPE: DNA
<213> ORGANISM: Homo sapiens

<400> SEQUENCE: 12

```
gtaatatctt gggcaagccc tagagcttct ttcctgaccc ttagttaata agatgttatc     60

tggtcacatt cagtcacaat aatagactca ttttagtaat aaacatctta agactagtaa    120

ttaaaactct ttacttcaca ccaagtttcc tccccaagct tggcctgttc ctggctggca    180

gcctgaagta gggaaaggag agatatggtg accttttctt tgtacctttc tagctaccct    240

ctataccctg accccacata cataattgag ctgtggcttc tgactctact gggtttgggg    300

atgagaggca gtgagagtaa aatgaaggag tggttttaat taatggcaca gctaaaactg    360
```

-continued

```
gattttgttc tctctgcaca tggcagatgt ttaaagctca ttctttcttt tatgcaagtt    420
tttacaccat ccagcctcat ttgtacctct tgaatttttg ctcagtggcc tatcaccatt    480
caggatcaag acaaaaatca atgagcactt attgtgtgtc atgcacccta caaagtgcca    540
ggatatttat ccaaactcct ggcaatgcta aacacaatgc aaaaagacat attagaaaac    600
gaatcttatt aactttagct tttcaactgt atttcatcat aaagtcttac tttacaagat    660
aattgctgtt gtgaaaaagg gaaaggtcat ggtctcattt cccagatgtt atttgatata    720
tgctataaat tatattacct ccaacatagt ctgcactttg aacttagaaa aacaatcttc    780
agacggcatg cattctaatt cttgaaataa gtatgcccac aaactgtagt ttaagacaga    840
ataggtatgc ttctcatgtt ttaattcagt tgaatttcag aagatctcag gaatgtacag    900
aacgagaatt aagaattaat aagaataaga attaattaat tgcttgacat agagtagtta    960
ggtgatttcc tgaactttaa gcttccacat cacagtatga agttggttca agataagaaa   1020
tataataaat tctcgcccaa ggacagacct gaatctctag ctgcctagag gctgactcaa   1080
ctgaaatcat ggcgtttgac agcacttgga aggtagaccg gagtgaaaac tatgacaagt   1140
tcatggaaaa aatgggtaaa gactttattt ctttgtggct cattctttgc tttcttacaa   1200
acatttttct ttctaactcc taaatctcta ggagattaca gatagcttac agatagctcc   1260
tgatgtggta gagagggatc cagaagatgt tcagaggagg gaaaccatat tttcccttct   1320
tacattagga agaatccact atctcactaa tggaagaaaa gattctttga gtgctgttct   1380
ctgaaacaca ccaaaaagat ccagaaatgt ttccttcact ctttaactga aaaatgactt   1440
tttttgttgt ttacagtaag aaaatggcag cgtgtaatga taacttccag atctgaaaat   1500
gttaaattct aggagatgga aaaacaaaga ccatataaga aagtaatgga aaaagttctc   1560
ttaaaattta tagctctgaa taagttagat ttaattctga tttcttctaa cttaaaaaag   1620
ttttggaata atcttgagaa gctgtgtagt tttctccagg gcgtttaatt taactgattt   1680
ataatttgat accaatactc tggcagccca tatactatac aagataggca aacaaatttg   1740
tgtcattccc ctaaaagaaa aatctgcatc aattatagct tacagtttag gaactctaag   1800
tttaaattta taaaagttgt agattcttat agtgattttg gcttaatatt tgctaatttt   1860
ctcatttttg tgtcagaaag aaatgccaca agaagcaaat agaactataa agttcaaaat   1920
gttaaagcca ctaagaaaaa caaaggggca tttaagaaaa aagaatactg tatatgtgga   1980
attaaagatg tgcttcctta taaatatatg aatatacatt ttaatccttc atttaatatt   2040
tctagaattt gatttactta acactgaaat gaacagtttg ttaatcttat taaggttgct   2100
cagctctaag attctataat tctgtactct acttaatttt tctcaagtta tggaaaaaca   2160
actttaatca gttctcttga tcggattgaa cctgaacttc tatagaagca atctgaatgt   2220
tcttgtgcaa aggcaatgct accgagtttt cttcccaccc tcaaaataaa caaacaaaac   2280
ataacttgga aaaataaaca cttcctatgg gatttgactt tattttctcc attgtcttac   2340
cttttacagg tgttaatata gtgaaaagga agcttgcagc tcatgacaat ttgaagctga   2400
caattacaca agaaggaaat aaattcacag tcaaagaatc aagcgctttt cgaaacattg   2460
aagttgtttt tgaacttggt gtcaccttta attacaacct agcagacgga actgaactca   2520
gggtaagaat ttttttttt atgagcaatg cattcttgat ttttctaccc aatattaaaa   2580
tgatttctgc tctatttcat tggatggttt aattaatgca ggtctccttc actaactgaa   2640
gaagccaatg aagtttgtct acattatata ttacacaaat tggcagggta tttaaatatg   2700
cttttatttt tatacgcatc tgtgaagaat ctgaattgaa cagtaagaat tagaaaacta   2760
```

-continued

```
tcttttgaat gactgaatat agacctattc ataaagaaat ttaaaactgt gtttttaaac   2820
agtacagcaa aagaagcctt tagagttaat atgtaactta actgtaacat gttgaaataa   2880
taaaagaaat gaatagatga acaaatgagt gagttaccaa atggaaagat ttgatgtatt   2940
gtaggtcatt gggagtgtac cttttcatgt ttaagataac acattttagg aagtcatcat   3000
tttcaacaaa ttttttaaaa actttttttta gcctcaacat ttttctattt aaattacatg   3060
tttgtaatga caatttaact actgaatgtt ttatcgtaag ttatgtcttt ccttaattag   3120
taccacaatc acacaaatta aaacaagcac aggttattaa catctccgtg aaactaattt   3180
taaccatgac tatatttctg gacacgtaac atgaaagatt cagaaagaag tgctgctcat   3240
ctgccttaaa attcagcgta tggaaattat tgaagagaac aagcataatg gttatcaaca   3300
catactctgt agcccaatgg cctaggttca atcctcactc tgtgacttta ggtgaatcac   3360
tgtgccattt tacagtctcc tcttctgcaa agtagagata gtagtatcag tttcataggg   3420
tcaccatgaa gattaaatga aaaagtgtgt ctacagaact cagaacagtg cctgacatgt   3480
gtaagaccct aataaatgcc attattatta ttattattat tattattatt attattatta   3540
tgtaggggac ctggagcctt gagggaaata aacttattgg aaaattcaaa cggacagaca   3600
atggaaacga actgaatact gtccgagaaa ttataggtga tgaactagtc caggtgagtt   3660
gtcaaattta tagctatttt caaaaggcaa aaattactac aaaacaataa tttttgtcac   3720
tgctgagcca gatcttcagt aaactgacta cttcttttct cataaatctt actgatttta   3780
aaaatattgt atagctattt tctgatgcct atttactaaa gacaacttat atatgtcaaa   3840
taatcaatgc ctattttaac tgaaaatata aatgactaca aaccaacatg tgttttaaaa   3900
tggctgtatc ccatatctgt ataaatcttg ctatcaagta caagaaaaaa ttgtataaac   3960
tcatactcat ataatatata tgaatatata atataaaaat agtataaact catatagtat   4020
aaaactataa tactactttt tcttaactta gatgtaaacc ttaaagataa attcttctgt   4080
ttgttaacac ctttcagact tatgtgtatg aaggagtaga agccaaaagg atctttaaaa   4140
aggattgagc attattcttg gcgcacagtc caaaatacaa attggacaga agatctatat   4200
tgtaccagaa ctgtttattt caccccatca agtataaggt tactgattga ttggtccttt   4260
tataaacatt ggtatatttc cattcatgcc aaagcaaaag aagtaaaagc taattaggat   4320
ttaatttgtt ttatattctc taagatatat atttactaaa agaatttgtg acattttaaa   4380
aaacaaaaat aaatattgca tccatgttgc tttatatgta gccttgcctt ttaaaagaaa   4440
aagtatgtga atatgaattg acagattgtt ttcgtagaga gagggtctta ctctttcact   4500
caggctggaa tgcagtggag agatcatagc tcactgtaac ctcaaactcc tggactcatg   4560
caatcttcct gcctcaggct tctgagtagc taggactatg ggtacattcc acagtgccca   4620
gctaattttt gttttgtttt ctttttattt tttttagaga tggggtcttg ctatattgcc   4680
caggctggtc ttgaacccct ggcctcaagc aatcctcctg cctcagcctc tcaagttgtt   4740
tttttcttta catttgataa actaaaagca taggctgcat atgagtcttt aacatcttga   4800
actggttgtg aataattttc tggcactggt tgtaagtaat atctattatt ataaaaataa   4860
tatatgctca accagaaaac ttagaaataa gaaacacaaa tgtaaaataa gtatttccat   4920
aactcataat ccagagataa ttgccattct gattttgata gatatcctct cagctctctt   4980
ccctgggggc agatatttcc caatacatac cactttgaat aggatgatag gaaataaatg   5040
atgtactaca ttaaattaaa ttattgtatt acatttttgt acacatcagt cattcccagg   5100
```

-continued

```
cttggctgaa aatcaggatc atctgagaaa cttaaacaat ttctgcattc ttaatctcca   5160

ctgttattct attatatcag aatcgctaat agaaccaaga attc                     5204


<210> SEQ ID NO 13
<211> LENGTH: 2480
<212> TYPE: DNA
<213> ORGANISM: Homo sapiens

<400> SEQUENCE: 13

gacgctctgt gccttcggag gtctttctgc ctgcctgtcc tcatgcctct cctcctcttg     60

ctgctcctgc tgccaagccc cttacacccc caccccatct gtgaggtctc caaagtggcc    120

agccacctag aagtgaactg tgacaagagg aatctgacag cgctgcctcc agacctgccg    180

aaagacacaa ccatcctcca cctgagtgag aacctcctgt acaccttctc cctggcaacc    240

ctgatgcctt acactcgcct cactcagctg aacctagata ggtgcgagct caccaagctc    300

caggtcgatg ggacgctgcc agtgctgggg accctggatc tatcccacaa tcagctgcaa    360

agcctgccct tgctagggca gacactgcct gctctcaccg tcctggacgt ctccttcaac    420

cggctgacct cgctgcctct tggtgccctg cgtggtcttg gcgaactcca agagctctac    480

ctgaaaggca atgagctgaa gaccctgccc ccagggctcc tgacgcccac acccaagctg    540

gagaagctca gtctggctaa caacaacttg actgagctcc ccgctgggct cctgaatggg    600

ctggagaatc tcgacaccct tctcctccaa gagaactcgc tgtatacaat accaaagggc    660

ttttttgggt cccacctcct gccttttgct ttctccacgg ggaacccctg gttatgcaac    720

tgtgagatcc tctattttcg tcgctggctg caggacaatg ctgaaaatgt ctacgtatgg    780

aagcaaggtg tggacgtcaa ggccatgacc tctaacgtgg ccagtgtgca gtgtgacaat    840

tcagacaagt ttcccgtcta caaataccca ggaaaggggt gccccaccct tggtgatgaa    900

ggtgacacag acctatatga ttactaccca gaagaggaca ctgagggcga taaggtgcgt    960

gccacaagga ctgtggtcaa gttccccacc aaagcccata caacccccctg gggtctattc   1020

tactcatggt ccactgcttc tctagacagc caaatgccct cctccttgca tccaacacaa   1080

gaatccacta aggagcagac cacattccca cctagatgga ccccaaattt cacacttcac   1140

atggaatcca tcacattctc caaaactcca aaatccacta ctgaaccaac cccaagcccg   1200

accacctcag agcccgtccc ggagcccgcc ccaaacatga ccaccctgga gcccactcca   1260

agcccgacca ccccagagcc cacctcagag cccgccccca gcccgaccac cccggagccc   1320

accccaatcc cgaccatcgc cacaagcccg accatcctgg tgtctgccac aagcctgatc   1380

actccaaaaa gcacattttt aactaccaca aaacccgtat cactcttaga atccaccaaa   1440

aaaaccatcc ctgaacttga tcagccacca aagctccgtg gggtgctcca agggcatttg   1500

gagagctcca gaaatgaccc ttttctccac cccgactttt gctgcctcct ccccctgggc   1560

ttctatgtct tgggtctctt ctggctgctc tttgcctctg tggtcctcat cctgctgctg   1620

agctgggttg ggcatgtgaa accacaggcc ctggactctg gccaaggtgc tgctctgacc   1680

acagccacac aaaccacaca cctggagctg cagaggggac ggcaagtgac agtgccccgg   1740

gcctggctgc tcttccttcg aggttcgctt cccactttcc gctccagcct cttcctgtgg   1800

gtacggccta atggccgtgt ggggcctcta gtggcaggaa ggaggccctc agctctgagt   1860

cagggtcgtg gtcaggacct gctgagcaca gtgagcatta ggtactctgg ccacagcctc   1920

tgagggtggg aggtttgggg accttgagag aagagcctgt gggctctcct attggaatct   1980

agttgggggt tggaggggta aggaacacag ggtgataggg gaggggtctt agttcctttt   2040
```

-continued

```
tctgtatcag aagccctgtc ttcacaacac aggcacacaa tttcagtccc agccaaagca   2100

gaaggggtaa tgacatggac ttggcggggg gacaagacaa agctcccgat gctgcatggg   2160

gcgctgccag atctcacggt gaaccatttt ggcagaatac agcatggttc ccacatgcat   2220

ttatgcacag aagaaaatct ggaaagtgat ttatcaggat gtgagcactc gttgtgtctg   2280

gatgttacaa atatgggtgg ttttattttc tttttccctg tttagcattt tctagttttc   2340

ttatcaggat gtgagcactc gttgtgtctg gatgttacaa atatgggtgg ttttattttc   2400

tttttccctg tttagcattt tctagttttc cactattatt gtatattatc tgtataataa   2460

aaaataattt tagggttggg                                               2480
```

<210> SEQ ID NO 14
<211> LENGTH: 959
<212> TYPE: DNA
<213> ORGANISM: Homo sapiens

<400> SEQUENCE: 14

```
aagcttttac catggtaacc cctggtcccg ttcagccacc accaccccac ccagcacacc     60

tccaacctca gccagacaag gttgttgaca caagagagcc ctcaggggca cagagagagt    120

ctggacacgt gggggagtca gccgtgtatc atcggaggcg gccgggcaca tggcagggat    180

gagggaaaga ccaagagtcc tctgttgggc ccaagtccta gacagacaaa acctagacaa    240

tcacgtggct ggctgcatgc cctgtggctg ttgggctggg cccaggagga gggaggggcg    300

ctctttcctg gaggtggtcc agagcaccgg gtggacagcc ctgggggaaa acttccacgt    360

tttgatggag gttatctttg ataactccac agtgacctgg ttcgccaaag gaaaagcagg    420

caaacgtgag ctgttttttt tttctccaag ctgaacacta ggggtcctag gctttttggg    480

tcacccggca tggcagacag tcaacctggc aggacatccg ggagagacag acacaggcag    540

agggcagaaa ggtcaaggga ggttctcagg ccaaggctat tggggtttgc tcaattgttc    600

ctgaatgctc ttacacacgt acacacacag agcagcacac acacacacac acacatgcct    660

cagcaagtcc cagagaggga ggtgtcgagg gggacccgct ggctgttcag acggactccc    720

agagccagtg agtgggtggg gctggaacat gagttcatct atttcctgcc cacatctggt    780

ataaaaggag gcagtggccc acagaggagc acagctgtgt ttggctgcag ggccaagagc    840

gctgtcaaga agacccacac gccccccctcc agcagctgaa ttcctgcagc tcagcagccg    900

ccgccagagc aggacgaacc gccaatcgca aggcacctct gagaacttca ggtaggaga     959
```

<210> SEQ ID NO 15
<211> LENGTH: 1337
<212> TYPE: DNA
<213> ORGANISM: Homo sapiens

<400> SEQUENCE: 15

```
cccccgacca tggcgaagct gattgcgctc accctcttgg ggatgggact ggcactcttc     60

aggaaccacc agtcttctta ccaaacacga cttaatgctc tccgagaggt acaacccgta    120

gaacttccta actgtaattt agttaaagga atcgaaactg gctctgaaga catggagata    180

ctgcctaatg gactggcttt cattagctct ggattaaagt atcctggaat aaagagcttc    240

aaccccaaca gtcctggaaa aatacttctg atggacctga atgaagaaga tccaacagtg    300

ttggaattgg ggatcactgg aagtaaattt gatgtatctt catttaaccc tcatgggatt    360

agcacattca cagatgaaga taatgccatg tacctcctgg tggtgaacca tccagatgcc    420

aagtccacag tggagttgtt taaatttcaa gaagaagaaa aatcgctttt gcatctaaaa    480
```

-continued

```
accatcagac ataaacttct gcctaatttg aatgatattg ttgctgtggg acctgagcac    540

ttttatggca caaatgatca ctattttctt gacccctact tacaatcctg ggagatgtat    600

ttgggtttag cgtggtcgta tgttgtctac tatagtccaa gtgaagttcg agtggtggca    660

gaaggatttg attttgctaa tggaatcaac atttcacccg atggcaagta tgtctatata    720

gctgagttgc tggctcataa gattcatgtg tatgaaaagc atgctaattg gactttaact    780

ccattgaagt cccttgactt taataccctc gtggataaca tatctgtgga tcctgagaca    840

ggagaccttt gggttggatg ccatcccaat ggcatgaaaa tcttcttcta tgactcagag    900

aatcctcctg catcagaggt gcttcgaatc cagaacattc taacagaaga acctaaagtg    960

acacaggttt atgcagaaaa tggcacagtg ttgcaaggca gtacagttgc ctctgtgtac   1020

aaagggaaac tgctgattgg cacagtgttt cacaaagctc tttactgtga gctctaacag   1080

accgatttgc acccatgcca tagaaactga ggccattatt tcaaccgctt gccatattcc   1140

gaggacccag tgttcttagc tgaacaatga atgctgaccc taaatgtgga catcatgaag   1200

catcaaagca ctgtttaact gggagtgata tgatgtgtag ggcttttttt tgagaataca   1260

ctatcaaatc agtcttggaa tacttgaaaa cctcatttac cataaaaatc cttctcacta   1320

aaatggataa atcagtt                                                  1337
```

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 16

```
ggacatggag gacgtncg                                                   18
```

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 17

```
cggacatgga ggacgtntg                                                  19
```

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 18

```
cgcggtactg caccaggc                                                   18
```

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (23)..(23)
<223> OTHER INFORMATION: n stands for any base

<400> SEQUENCE: 19
gagtctacct gtttactatc aanaa 25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (23)..(23)
<223> OTHER INFORMATION: n stands for any base

<400> SEQUENCE: 20
gagtctacct gtttactatc aanga 25

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 21
accagtacta aagcaaatta aact 24

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (18)..(18)
<223> OTHER INFORMATION: n stands for any base

<400> SEQUENCE: 22
ggccctgtct tcgttaangg 20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (20)..(20)
<223> OTHER INFORMATION: n stands for any base

<400> SEQUENCE: 23
atggccctgt cttcgttaan tg 22

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 24
ccagggctat ggaagtcgag tatc 24

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 25
tctgcggcat cacgtncg 18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 26
tctgcggcat cacgtntg 18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 27
gaatagtagg cggccactga 20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 28
cggagccact gatgcncg 18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 29
cggagccact gatgcntg 18

-continued

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 30
tgtttggagt aaaggcacag aa 22

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 31
cggcagcttc ttcccncg 18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 32
cggcagcttc ttcccntg 18

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 33
ccacccctca gctataaata gg 22

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 34
cgagttggga acgcacnct 19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 35
cgagttggga acgcacngt 19

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 36
ggtctgcact gacattgatg ag 22

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 37
cccgactcgg cccttncc 18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 38
cccgactcgg cccttntc 18

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 39
gtcacagtcg gtgccaatgt 20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (19)..(19)
<223> OTHER INFORMATION: n stands for any base

<400> SEQUENCE: 40
ccgacatcag cattgtctna t 21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (19)..(19)
<223> OTHER INFORMATION: n stands for any base

<400> SEQUENCE: 41
ccgacatcag cattgtctng t 21

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 42
ctgcagggaa gggagctgt 19

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (19)..(19)
<223> OTHER INFORMATION: n stands for any base

<400> SEQUENCE: 43
ttcttttggt ggagcaacng t 21

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (20)..(20)
<223> OTHER INFORMATION: n stands for any base

<400> SEQUENCE: 44
attcttttgg tggagcaacn tt 22

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 45
tcttacctga atctctgatc ttca 24

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 46
acattcaccg tggccantg 19

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 47
cattcaccgt ggccangg 18

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 48
agctgcctgt accaatacat cc 22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (20)..(20)
<223> OTHER INFORMATION: n stands for any base

<400> SEQUENCE: 49
tcacagtcaa agaatcaagn gc 22

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (22)..(22)
<223> OTHER INFORMATION: n stands for any base

<400> SEQUENCE: 50
attcacagtc aaagaatcaa gnac 24

-continued

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 51
caaaaacaac ttcaatgttt cga 23

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (14)..(14)
<223> OTHER INFORMATION: n stands for any base

<400> SEQUENCE: 52
cccagggctc ctgncg 16

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (15)..(15)
<223> OTHER INFORMATION: n stands for any base

<400> SEQUENCE: 53
ccccagggct cctgntg 17

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 54
tgagcttctc cagcttgggt g 21

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 55
ggcacagaga gagtctggac acg 23

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 56
ggccgcctcc gatgataca 19

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (22)..(22)
<223> OTHER INFORMATION: n stands for any base

<400> SEQUENCE: 57
acccaaatac atctcccagg ancg 24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (22)..(22)
<223> OTHER INFORMATION: n stands for any base

<400> SEQUENCE: 58
aacccaaata catctcccag gnct 24

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 59
gaatgatatt gttgctgtgg gac 23

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (13)..(13)
<223> OTHER INFORMATION: n stands for any base

<400> SEQUENCE: 60
agccactgat gcncggtct 19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (13)..(13)
<223> OTHER INFORMATION: n stands for any base

<400> SEQUENCE: 61
agccactgat gcntggtct 19

-continued

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (12)..(12)
<223> OTHER INFORMATION: n stands for any base

<400> SEQUENCE: 62
caccgtggcc antgcaggat 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (12)..(12)
<223> OTHER INFORMATION: n stands for any base

<400> SEQUENCE: 63
caccgtggcc anggcaggat 20

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (9)..(9)
<223> OTHER INFORMATION: n stands for any base

<400> SEQUENCE: 64
gaatcaagng cttttcgaaa catt 24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (9)..(9)
<223> OTHER INFORMATION: n stands for any base

<400> SEQUENCE: 65
gaatcaagna cttttcgaaa catt 24

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:Probe

<400> SEQUENCE: 66
tggacacgtg ggggagtcag 20

-continued

```
<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence:Probe

<400> SEQUENCE: 67

tggacacgtg gggagtcagc                                              20
```